United States Patent
Wang et al.

(10) Patent No.: US 10,533,965 B2
(45) Date of Patent: Jan. 14, 2020

(54) COMBUSTIBLE GAS SENSING ELEMENT WITH CANTILEVER SUPPORT

(71) Applicant: Industrial Scientific Corporation, Pittsburgh, PA (US)

(72) Inventors: Chuan-Bao Wang, Franklin Park, PA (US); Kathryn Salvetti, Pittsburgh, PA (US); Yong Wang, Mars, PA (US)

(73) Assignee: Industrial Scientific Corporation, Pittsburgh, PA (US)

( * ) Notice: Subject to any disclaimer, the term of this patent is extended or adjusted under 35 U.S.C. 154(b) by 227 days.

(21) Appl. No.: 15/665,034

(22) Filed: Jul. 31, 2017

(65) Prior Publication Data

US 2018/0024091 A1    Jan. 25, 2018

Related U.S. Application Data

(63) Continuation-in-part of application No. 15/491,311, filed on Apr. 19, 2017.

(60) Provisional application No. 62/384,798, filed on Sep. 8, 2016, provisional application No. 62/409,706, filed on Oct. 18, 2016, provisional application No. (Continued)

(51) Int. Cl.
*G01N 27/40* (2006.01)
*G01N 27/407* (2006.01)
*G08B 21/16* (2006.01)

(52) U.S. Cl.
CPC ......... *G01N 27/4075* (2013.01); *G08B 21/16* (2013.01)

(58) Field of Classification Search
CPC ..... G01N 27/4075; H04B 1/713; H04W 4/80; H04W 56/0015; H04W 52/0235; H04W 84/18; H04W 48/10; Y02D 70/40; Y02D 70/162; Y02D 70/26; Y02D 70/22; Y02D 70/144; Y02D 70/142; Y02D 70/166; Y02D 70/164; G08B 21/16
See application file for complete search history.

(56) References Cited

U.S. PATENT DOCUMENTS 4,416,911 A * 11/1983 Wilkinson-Tough ....... G01N 27/16 427/101
4,457,954 A * 7/1984 Dabill ............... G01N 27/16 422/97

(Continued)

FOREIGN PATENT DOCUMENTS

AU 2017219135 B2 11/2018
CA 2803246 A1 12/2011
(Continued)

OTHER PUBLICATIONS

"Personal Wireless Monitor for Toxic Gases and Oxygen", JM Test Systems, 2016, 2 Pages.
(Continued)

*Primary Examiner* — Francis C Gray
(74) *Attorney, Agent, or Firm* — GTC Law Group PC & Affiliates

(57) ABSTRACT

A catalytically activated combustible gas sensing element includes a filament of resistance wire forming a coil, wherein a first end of the resistance wire is attached to a first support post and a second end of the resistance wire is attached to a second support post, a cantilever support supporting the coil, wherein the cantilever support is attached to a third support post, and a catalytic bead substantially surrounding the coil and cantilever.

28 Claims, 49 Drawing Sheets

Related U.S. Application Data

62/397,587, filed on Sep. 21, 2016, provisional application No. 62/384,803, filed on Sep. 8, 2016, provisional application No. 62/463,230, filed on Feb. 24, 2017, provisional application No. 62/324,573, filed on Apr. 19, 2016, provisional application No. 62/364,935, filed on Jul. 21, 2016, provisional application No. 62/385,688, filed on Sep. 9, 2016.

(56) References Cited

U.S. PATENT DOCUMENTS

| | | | |
|---|---|---|---|
| 4,472,353 A | 9/1984 | Moore et al. | |
| 4,473,797 A | 9/1984 | Shiota | |
| 4,525,872 A | 6/1985 | Zochowski et al. | |
| 4,572,878 A | 2/1986 | Daugherty | |
| 4,574,042 A | 3/1986 | Shiraishi | |
| 4,775,083 A | 10/1988 | Burger et al. | |
| 4,931,780 A | 5/1990 | LaMont et al. | |
| 5,005,419 A | 4/1991 | O'Donnell et al. | |
| 5,101,271 A | 3/1992 | Andrews et al. | |
| 5,138,559 A | 8/1992 | Kuehl et al. | |
| 5,493,273 A | 2/1996 | Smurlo et al. | |
| 5,568,121 A | 10/1996 | Lamensdorf | |
| 5,916,180 A | 6/1999 | Cundari et al. | |
| 5,932,176 A * | 8/1999 | Yannopoulos | G01N 33/0052 422/98 |
| 6,182,497 B1 | 2/2001 | Krajci | |
| 6,466,608 B1 | 10/2002 | Hong et al. | |
| 6,629,152 B2 | 9/2003 | Kingsbury et al. | |
| 6,644,098 B2 * | 11/2003 | Cardinale | G01N 27/12 324/443 |
| 6,649,876 B2 * | 11/2003 | Cardinale | G01N 27/12 204/431 |
| 6,666,963 B1 | 12/2003 | Peng et al. | |
| 6,703,840 B2 * | 3/2004 | Cardinale | G01N 27/122 204/425 |
| 6,816,460 B1 | 11/2004 | Ahmed et al. | |
| 6,822,573 B2 | 11/2004 | Basir et al. | |
| 7,007,542 B2 | 3/2006 | Wang et al. | |
| 7,020,508 B2 | 3/2006 | Stivoric et al. | |
| 7,220,387 B2 | 5/2007 | Flaherty et al. | |
| 7,463,142 B2 | 12/2008 | Lindsay et al. | |
| 7,471,200 B2 | 12/2008 | Otranen | |
| 7,587,619 B2 | 9/2009 | Ryan | |
| 7,608,177 B2 | 10/2009 | Nauber et al. | |
| 7,613,156 B2 | 11/2009 | Rittle et al. | |
| 7,649,872 B2 | 1/2010 | Naghian et al. | |
| 7,688,802 B2 | 3/2010 | Gonia et al. | |
| 7,697,893 B2 | 4/2010 | Kossi et al. | |
| 7,880,607 B2 | 2/2011 | Olson et al. | |
| 7,885,291 B2 | 2/2011 | Delaney | |
| 7,888,825 B2 | 2/2011 | Koshi et al. | |
| 7,895,309 B2 | 2/2011 | Belali et al. | |
| 7,917,673 B2 | 3/2011 | Suh | |
| 7,970,871 B2 | 6/2011 | Ewing et al. | |
| 7,978,717 B2 | 7/2011 | Banks et al. | |
| 8,009,437 B2 | 8/2011 | Shelton et al. | |
| 8,035,491 B2 | 10/2011 | Banks | |
| 8,081,590 B2 | 12/2011 | Patterson et al. | |
| 8,085,144 B2 | 12/2011 | Appelt et al. | |
| 8,204,971 B2 | 6/2012 | Ewing et al. | |
| 8,224,246 B2 | 7/2012 | Suumaki et al. | |
| 8,294,568 B2 | 10/2012 | Barrett et al. | |
| 8,358,214 B2 | 1/2013 | Gingrave et al. | |
| 8,385,322 B2 | 2/2013 | Colling et al. | |
| 8,400,317 B2 | 3/2013 | Johnson et al. | |
| 8,416,120 B2 | 4/2013 | Kim et al. | |
| 8,418,064 B2 | 4/2013 | Guagenti et al. | |
| 8,438,250 B2 | 5/2013 | Ewing et al. | |
| 8,442,801 B2 | 5/2013 | Gonla et al. | |
| 8,462,707 B2 | 6/2013 | Husney | |
| 8,494,502 B2 | 7/2013 | Abel et al. | |
| 8,514,087 B2 | 8/2013 | Little et al. | |
| 8,547,888 B2 | 10/2013 | Filoso et al. | |
| 8,585,606 B2 | 11/2013 | McDonald et al. | |
| 8,587,414 B2 | 11/2013 | Bandyopadhyay et al. | |
| 8,638,228 B2 | 1/2014 | Amigo et al. | |
| 8,665,097 B2 | 3/2014 | Stinson et al. | |
| 8,792,401 B2 | 7/2014 | Banks et al. | |
| 8,805,430 B2 | 8/2014 | Olsen et al. | |
| 8,818,397 B2 | 8/2014 | Shikowitz et al. | |
| 8,868,703 B2 | 10/2014 | Ewing et al. | |
| 8,885,513 B2 | 11/2014 | Ewing | |
| 9,000,910 B2 | 4/2015 | Arunachalam | |
| 9,195,866 B1 | 11/2015 | Mehranfar et al. | |
| 9,536,418 B2 | 1/2017 | Mao et al. | |
| 9,575,043 B2 | 2/2017 | Arunachalam | |
| 9,743,221 B2 | 2/2017 | Javer et al. | |
| 9,619,986 B2 | 4/2017 | Seol | |
| 9,721,456 B2 | 8/2017 | Thurlow et al. | |
| 9,792,808 B2 | 10/2017 | Gnanasekaran et al. | |
| 9,847,008 B2 | 12/2017 | Hunter et al. | |
| 10,055,971 B2 | 8/2018 | M R et al. | |
| 10,062,260 B2 | 8/2018 | Hunter et al. | |
| 2001/0050612 A1 | 12/2001 | Shaffer | |
| 2002/0126002 A1 | 9/2002 | Patchell et al. | |
| 2002/0146352 A1 * | 10/2002 | Wang | G01N 27/16 422/96 |
| 2002/0155622 A1 | 10/2002 | Slater et al. | |
| 2003/0067393 A1 | 4/2003 | Albro et al. | |
| 2003/0150252 A1 | 8/2003 | Wang et al. | |
| 2003/0159497 A1 | 8/2003 | Warburton et al. | |
| 2003/0180445 A1 * | 9/2003 | Wang | C23C 4/02 427/58 |
| 2004/0119591 A1 | 6/2004 | Peeters | |
| 2005/0083194 A1 | 4/2005 | Shen et al. | |
| 2005/0202582 A1 | 9/2005 | Eversmann et al. | |
| 2005/0243794 A1 | 11/2005 | Yoon et al. | |
| 2005/0252980 A1 | 11/2005 | Kim et al. | |
| 2006/0019402 A1 * | 1/2006 | Wang | G01N 27/16 436/151 |
| 2006/0224357 A1 | 10/2006 | Taware et al. | |
| 2006/0257289 A1 | 11/2006 | Martens et al. | |
| 2007/0000310 A1 | 1/2007 | Yamartino et al. | |
| 2007/0078608 A1 | 4/2007 | Broy et al. | |
| 2007/0171042 A1 | 7/2007 | Metes et al. | |
| 2007/0241261 A1 | 10/2007 | Wendt | |
| 2007/0257806 A1 | 11/2007 | Madden et al. | |
| 2008/0015794 A1 | 1/2008 | Eiler et al. | |
| 2008/0038590 A1 | 2/2008 | Nakakubo et al. | |
| 2008/0058614 A1 | 3/2008 | Banet et al. | |
| 2008/0122641 A1 | 5/2008 | Amidi et al. | |
| 2008/0146895 A1 | 6/2008 | Olson et al. | |
| 2008/0240463 A1 | 10/2008 | Florencio et al. | |
| 2009/0089108 A1 | 4/2009 | Angell et al. | |
| 2009/0115654 A1 | 5/2009 | Lo et al. | |
| 2009/0210257 A1 | 8/2009 | Chalfant et al. | |
| 2009/0312976 A1 | 12/2009 | Bingham et al. | |
| 2010/0072334 A1 | 3/2010 | Le Gette et al. | |
| 2010/0267407 A1 | 10/2010 | Liao et al. | |
| 2011/0022421 A1 | 1/2011 | Brown et al. | |
| 2011/0115623 A1 | 5/2011 | Gnanasekaran et al. | |
| 2011/0161885 A1 | 6/2011 | Gonia et al. | |
| 2012/0150755 A1 | 6/2012 | Kumar et al. | |
| 2012/0176237 A1 | 7/2012 | Tabe et al. | |
| 2013/0006064 A1 | 1/2013 | Reiner et al. | |
| 2013/0057391 A1 | 3/2013 | Salvador et al. | |
| 2013/0253809 A1 | 9/2013 | Jones et al. | |
| 2013/0278412 A1 | 10/2013 | Kelly et al. | |
| 2014/0082185 A1 | 3/2014 | Abraham et al. | |
| 2014/0122537 A1 | 5/2014 | Stivoric et al. | |
| 2014/0233458 A1 | 8/2014 | Georgescu et al. | |
| 2014/0274155 A1 | 9/2014 | Langberg | |
| 2014/0310349 A1 | 10/2014 | Rainisto | |
| 2014/0362836 A1 | 12/2014 | Williams, II et al. | |
| 2014/0368354 A1 | 12/2014 | Skourlis | |
| 2015/0006633 A1 | 1/2015 | Vandwalle et al. | |
| 2015/0025917 A1 | 1/2015 | Stempora | |
| 2015/0063202 A1 | 3/2015 | Mazzarella et al. | |
| 2015/0127733 A1 | 5/2015 | Ding et al. | |
| 2015/0145649 A1 | 5/2015 | Michaud et al. | |
| 2015/0145685 A1 | 5/2015 | Albinger et al. | |
| 2015/0161876 A1 | 6/2015 | Castillo | |
| 2015/0163652 A1 | 6/2015 | Michaud et al. | |

(56) References Cited

U.S. PATENT DOCUMENTS

| | | |
|---|---|---|
| 2015/0212037 A1 | 7/2015 | Okazaki et al. |
| 2015/0245385 A1 | 8/2015 | Nambord et al. |
| 2016/0209386 A1 | 7/2016 | Belski et al. |
| 2016/0334378 A1 | 11/2016 | Maddila et al. |
| 2016/0358444 A1 | 12/2016 | Lundy |
| 2016/0363516 A1 | 12/2016 | Chou et al. |
| 2017/0004700 A1 | 1/2017 | Kim |
| 2017/0102369 A1 | 4/2017 | Arunachalam |
| 2017/0132884 A1 | 5/2017 | Kumar et al. |
| 2017/0303187 A1 | 10/2017 | Crouthamel et al. |
| 2018/0082565 A1 | 3/2018 | Braiman |

FOREIGN PATENT DOCUMENTS

| | | |
|---|---|---|
| CN | 2135808 Y | 6/1993 |
| CN | 104903953 A | 9/2015 |
| CN | 105092796 B | 12/2018 |
| CN | 109565516 A | 4/2019 |
| EP | 2586018 A1 | 5/2013 |
| EP | 3227808 A1 | 10/2017 |
| EP | 3228068 A1 | 10/2017 |
| EP | 2287789 B1 | 11/2017 |
| GB | 2423400 A | 8/2006 |
| JP | 2002344602 A | 11/2002 |
| JP | 2007193773 A | 8/2007 |
| WO | 1995026492 A1 | 10/1995 |
| WO | 2008111755 A1 | 9/2008 |
| WO | 2011163604 A1 | 12/2011 |
| WO | 2014184638 A1 | 11/2014 |
| WO | 2016005805 A1 | 1/2016 |
| WO | 2017142847 A1 | 8/2017 |
| WO | 2017184702 A1 | 10/2017 |
| WO | 2018048517 A1 | 3/2018 |
| WO | 2018165883 A1 | 9/2018 |

OTHER PUBLICATIONS

"RECON/4 Manual", ENMET Corporation, Jun. 22, 2009, p. 1-10.
"Sensit P100", Personal Single Gas Monitor, 2010, 4 Pages.
"Single Gas Detector, Oxygen", BW Technologies, 2016, 3 Pages.
"Solaris Multigas Detector, "Solaris Multigas Detector, Solaris MUL Tigas Manual, MSA Instrument Division, Jan. 1, 2005 (Jan. 1, 2005), pp. 1-162,, Jan. 1, 2005, p. 1-162.
"Solaris Multigas Detector", ID #08-1650/Jun. 2003, MSA Solaris, Jun. 2003, p. 1-4.
"ToxiRAE 3", JM Test Systems, 2016, 3 Pages.
"Wearable Sensors in Transportation-Exploratory Advanced Research Program Initial Stage Investigation", The Exploratory Advanced Research Program, Mar. 2016, 52 pages.
Azhari, et al., "On the Performance of Off-Body Links for a Wireless Body Area Network in an Underground Mining Environment", International Journal of Computer Science and Innovation, vol. 2015, No. 2,, 2015, pp. 53-67.
Ding, et al., "Redundant Sensor Calibration Monitoring Using Independent Component Analysis and Pricipal Component Analysis", Real Time Systems, Kluwer Academic Publishers, Dordrecht, NL, val. 27, Jan. 1, 2004 (Jan. 1, 2004), pp. 27-47, XP007919437, ISSN: 0922-6443, May 2004, p. 27-47.
Dorsavi, "ViPerform-Provides Objective Data to Accurately Assess Risk of Injury, Guide Training Programs, and Help Determine When It's Safe to Return to Play", Available online at <http://us.dorsavi.com/viperform/>, Dorsavi Revolutionary Wearable Sensor Technology, retrieved on Jul. 10, 2016, 12 pages.
Eikon, "Eikon Intrinisically Safe Personal Gas Alarm", http://www.breathepureair.com/crowcon-eikon.html, Jan. 2016, 1-3.
Giang, Vivian, "Companies Are Putting Sensors on Employees to Track Their Every Move", Tracking Employees With Productivity Sensors—Business Insider, Available online at <http://www.businessinsider.com/tracking-employees-with-productivity-sensors-2013-3>, Mar. 14, 2013, pp. 1-4.
Mayton, et al., "TRUSS: Tracking Risk with Ubiquitous Smart Sensing", In 2012 IEEE Sensors, Institute of Electrical and Electronics Engineers (IEEE),, 2012, pp. 1-4.
PCT/US2017/028320, "Application Serial No. PCT/US2017/028320 , International Search Report and the Written Opinion dated Aug. 14, 2017", 14 pages.
PCT/US2017/028320, "International Application Serial No. PCT/US2017/028320, International Preliminary Report on Patentability and Written Opinion dated Nov. 1, 2018", Industrial Scientific Corporation, 11 Pages.
PCT/US2017/044735, "International Application Serial No. PCT/US2017/044735, International Search Report and Written Opinion dated Jan. 18, 2018", Industrial Scientific Corporation, 14 Pages.
PCT/US2017/044735, "International Application Serial No. PCT/US2017/044735, Invitation to Pay Additional Fees and, Where Applicable, Protest Fee dated Nov. 7, 2017", Industrial Scientific Corporation, 2 Pages.
Peaksoft Technologies, "Big Idea Seeing Crime Before It Happens", Available online at <http://www.pstpl.com/news184.html>, Dec. 3, 2011, pp. 1-2.
Texas Instruments, "CC2541 SensorTag Quick Start Guide", www.ti.com/lprf, Opening the Box and Using the SensorTag, Apr. 2013, 1-7.
PCT/US2017/044735, "International Application Serial No. PCT/US2017/044735, International Preliminary Report on Patentability and Written Opinion dated Mar. 21, 2019", Industrial Scientific Corporation, 6 pages.

* cited by examiner

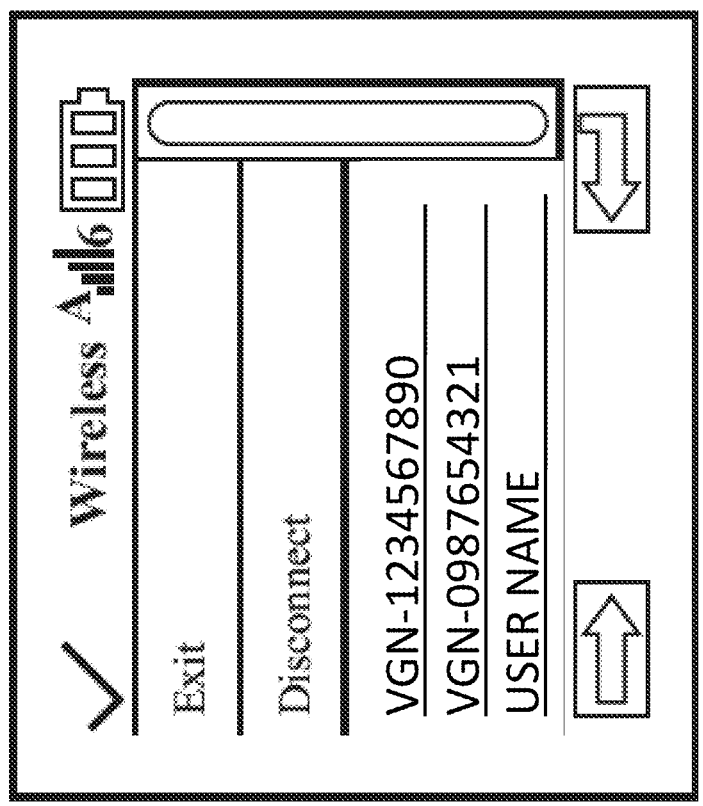
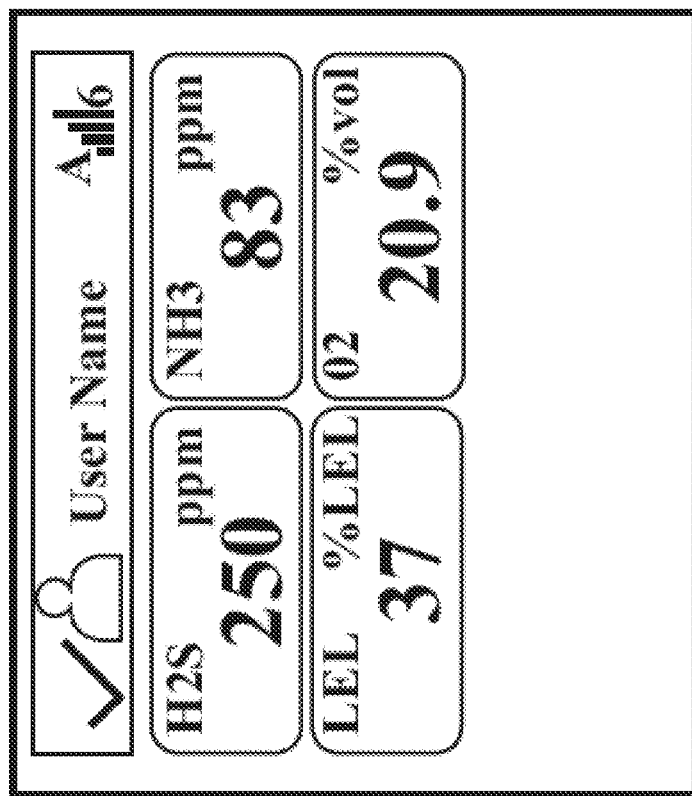
FIG. 6A
FIG. 6B

| Function | OSI Model | 802.15.4 | Mesh Network | Peer-to-peer Network | Devices |
|---|---|---|---|---|---|
| Identifying Partners | 7. Application | | User's Host System C/C++, JAVA, etc.) | Gas Detection, Location, Panic, Man Down, Vital | Instrument MCU |
| Sending/Receiving Info | | | | | |
| Symantics | 6. Presentation | Undefined | User-defined Scripts | Wireless Protocol | |
| Syntax | | | | | |
| Device Profiles | | | | | |
| Connections | 5. Session | | VM, RPC Framework, Data, Mesh Networking | Network Operating System | Radio MCU |
| Ack/Nak | 4. Transport | | | | |
| Retransmission | | | | | |
| Network Routing | 3. Network | | | | |
| Fragmentation/Reassembly | | | | | |
| Flow Control | 2. Data Link Layer | 802.15.4 MAC | 802.15.4 Packet interface | | |
| Error Control | | | | | |
| Access Control | | | | | |
| Framing | | | Module Hardware Abstraction I/O, modem, etc. | Radio Module/ IC; other hardware | |
| Physical Addressing | | | | | |
| Media Access Control (MAC) | | | | | |
| Media | 1. Physical Layer | 2.4GHz DSSS Radio (250kbps) | | | Radio Modem |
| Channels and Modulation | | | | | |

FIG. 13

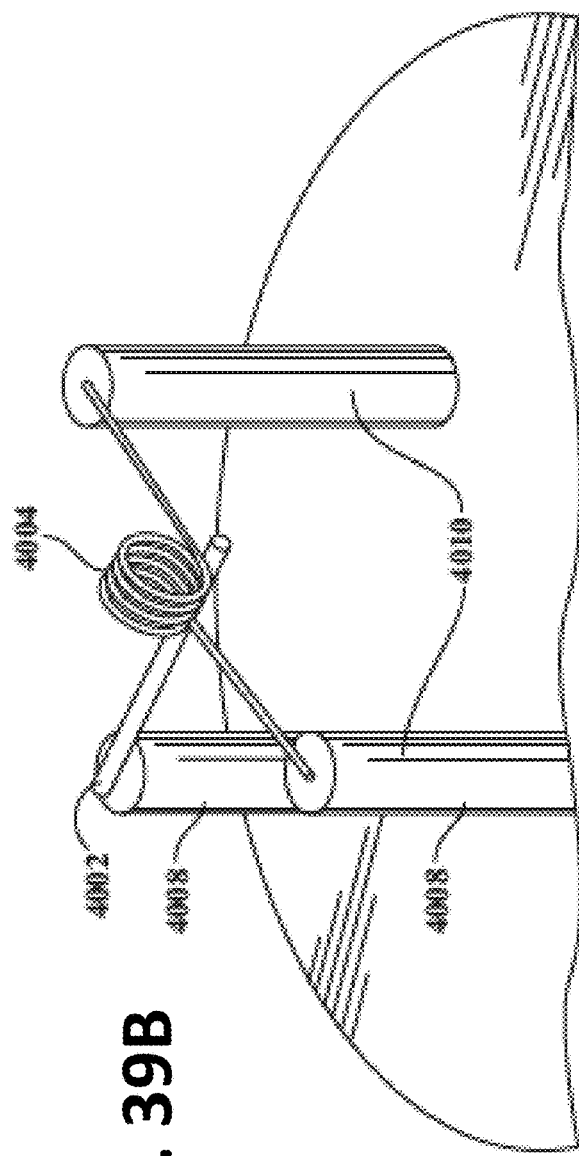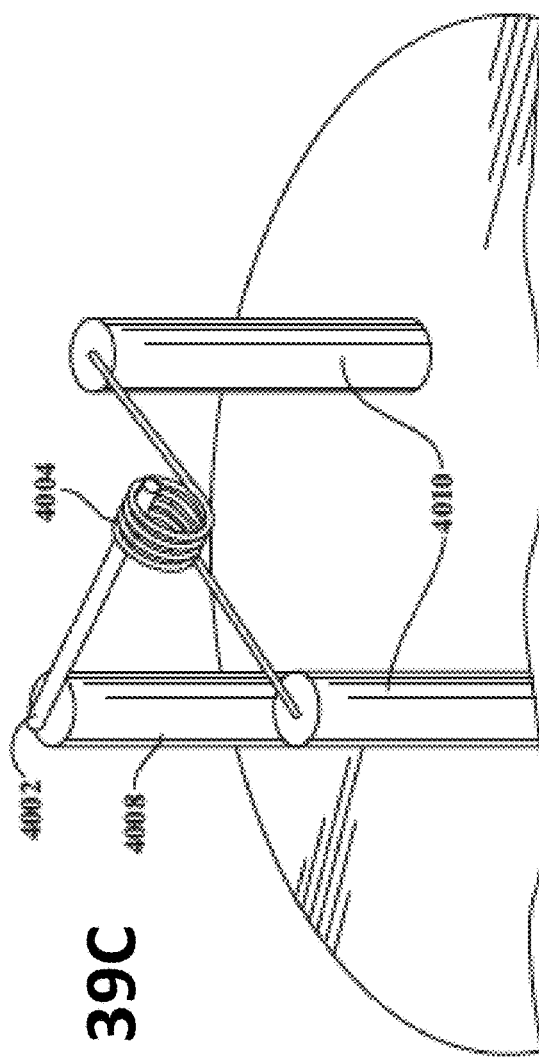

COMBUSTIBLE GAS SENSING ELEMENT WITH CANTILEVER SUPPORT

CLAIM TO PRIORITY

This application claims the benefit of the following provisional applications, each of which is hereby incorporated by reference in its entirety: U.S. Ser. No. 62/384,798, filed Sep. 8, 2016 (ISCI-0025-P01); U.S. Ser. No. 62/409,706, filed Oct. 18, 2016 (ISCI-0034-P01); U.S. Ser. No. 62/397,587, filed Sep. 21, 2016 (ISCI-0035-P01); U.S. Ser. No. 62/384,803, filed Sep. 8, 2016 (ISCI-0036-P01); and U.S. Ser. No. 62/463,230, filed Feb. 24, 2017 (ISCI-0038-P01).

This application is a continuation-in-part of U.S. Ser. No. 15/491,311, filed Apr. 19, 2017 (ISCI-0039-U01). U.S. Ser. No. 15/491,311 claims the benefit of the following provisional applications, each of which is hereby incorporated by reference in its entirety: U.S. Ser. No. 62/324,573, filed Apr. 19, 2016 (ISCI-0026-P01); U.S. Ser. No. 62/364,935, filed Jul. 21, 2016 (ISCI-0027-P01); and U.S. Ser. No. 62/385,688, filed Sep. 9, 2016 (ISCI-0037-P01).

This application is also related to the following U.S. patents and patent applications each of which is incorporated by reference herein in its entirety: U.S. Pat. No. 9,000,910 filed on Jun. 24, 2011 (ISCI-0020-U01), U.S. Pat. No. 9,575,043 filed Apr. 1, 2015 (ISCI-0020-U01-001), U.S. patent application Ser. No. 15/376,823, filed Dec. 13, 2016 (ISCI-0020-U01-001-001), U.S. Pat. No. 6,338,266 filed Apr. 5, 2000 (ISCI-0005-U01), U.S. Pat. No. 6,435,003 filed Nov. 8, 2001 (ISCI-0005-U01-V01), U.S. Pat. No. 6,888,467 filed Dec. 10, 2002 (ISCI-0014-U01), U.S. Pat. No. 6,742,382 filed Dec. 24, 2002 (ISCI-0015-U01), U.S. Pat. No. 6,442,639 filed Apr. 19, 2000 (ISCI-0006-U01), U.S. Pat. No. 7,007,542 filed Jun. 16, 2003 (ISCI-0009-U01-V01), and U.S. Patent Application Serial No. 2016/0209386, entitled MODULAR GAS MONITORING SYSTEM and filed on Jan. 15, 2016 (ISCI-0023-U01).

BACKGROUND

Field

The invention relates to combustible gas sensors, and more particularly to a combustible gas sensor with improved mechanical stability.

SUMMARY

In an aspect, a tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to multi-gas detection instrument operators; receiving temporary assignment information at the safety device when an NFC radio of the safety device is brought in proximity to at least one of the plurality of NFC tags; and tagging safety device data with the temporary assignment information. In this aspect and others disclosed herein, the programming of the plurality of NFC tags is not required. In fact, pre-programmed NFC tags may be purchased for use in the systems and methods disclosed herein. The operations further include storing the tagged safety device data in a safety device data log. The operations further include wirelessly transmitting the tagged safety device data to at least one of a cloud-based or other remote log and a second device. The operations further include removing the temporary assignment by bringing the safety device into proximity to the at least one NFC tag again. The safety device is a multi-gas detection instrument, a gas detection instrument, or at least one of a respirator, a harness, a lighting device, a fall arrest device, a thermal detector, a flame detector, and a chemical, biological, radiological, nuclear, and explosives (CBRNE) detector.

In an aspect, a tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to safety device operators; receiving assignment information at the safety device when an NFC radio of the safety device is brought in proximity to at least one of the plurality of NFC tags; and triggering one or more of an alarm and a message upon detection of a safety event, wherein the trigger is filtered by the temporary assignment information. The assignment tags for identifying individuals are programmed with information including one or more of a name, a size, a weight, a typical work location, a job function, a typical instrument used, a pre-existing concern, a language known, a prior alarm, a prior gas event, a prior safety event, and a prior message. The assignment tags for identifying locations are programmed with information including one or more of a location within a space, a GPS location, an equipment at the location, a fuel source at the location, a known hazard at the location, a typical gas concentration for the location, an environmental condition for the location, a recent gas event, a recent man down alarm, a recent alarm, and a recent message. Triggering further comprises applying a filter based on the assignment tag's programmed information. The safety device is at least one of a multi-gas detection instrument, a gas detection instrument, a respirator, a harness, a lighting device, a fall arrest device, a thermal detector, a flame detector, and a chemical, biological, radiological, nuclear, and explosives (CBRNE) detector. The safety event is a gas event.

In an aspect, an industrial safety monitoring system includes a personal NFC tag assigned to a worker, wherein the tag assigned to the worker comprises information of the identity of the worker; a plurality of location NFC tags assigned to locations, each location tag placed in a location comprising information of the location in which the location tag is placed; at least one portable environmental sensing device detecting data of an environmental parameter, the at least one portable environmental sensing device configured to (i) read the personal NFC tag and to transmit the information of the identity of the worker using the sensing device, and (ii) read at least one of the plurality of location NFC tags and to transmit the information of the location of a location tag read by the at least one portable environmental sensing device; and at least one processor in communication with the at least one portable environmental sensing device and receiving from the at least one portable environmental sensing device (i) detected data of an environmental parameter, (ii) the information of the identity of the worker using the at least one portable environmental sensing device, and (iii) information of the location of a location tag read by the at least one portable environmental sensing device, wherein the at least one processor is programmed to determine an environmental parameter of the worker using the sensing device and the location of the determined environmental parameter. The system further includes a memory in communication with the at least one portable environmental sensing device that stores the detected data and the information in a portable environmental sensing device data log. The system further includes a wireless transmitter that transmits the detected data and the information to at least one of a cloud-based or other remote log and a second portable environmental sensing device. The assignment tags for identifying workers are programmed with information including one or more of a name, a size, a weight, a typical work location, a job function, a typical instrument used, a pre-existing concern, a language known, a prior alarm, a prior gas event, a prior safety event, and a prior message. The assignment tags for identifying locations are programmed with information including one or more of a location within a space, a GPS location, an equipment at the location, a fuel source at the location, a known hazard at the location, a typical gas concentration for the location, an environmental condition for the location, a recent gas event, a recent man down alarm, a recent alarm, and a recent message. The at least one portable environmental sensing device is at least one of a multi-gas detection instrument, a gas detection instrument, a respirator, a harness, a lighting device, a fall arrest device, a thermal detector, a flame detector, and a chemical, biological, radiological, nuclear, and explosives (CBRNE) detector.

In an aspect, a tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to safety device operators; receiving assignment information at the safety device when an NFC radio of the safety device is brought in proximity to at least one of the plurality of NFC tags; and triggering an activation of a function of the safety device based on the temporary assignment information.

In an aspect, A tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to safety device operators; receiving assignment information at the safety device when an NFC radio of the safety device is brought in proximity to at least one of the plurality of NFC tags; and triggering a modification of a setting of the safety device based on the temporary assignment information.

In an aspect, a tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to safety device operators; receiving assignment information at the safety device when an NFC radio of the safety device is brought in proximity to at least one of the plurality of NFC tags; triggering one or more of an alarm and a message upon detection of a safety event, wherein the triggered alarm or message is filtered by the temporary assignment information; and communicating the triggered alarm or message to at least one other safety device in a mesh network with features as described herein for presentation on the second safety device. The assignment tags for identifying individuals are programmed with information including one or more of a name, a size, a weight, a typical work location, a job function, a typical instrument used, a pre-existing concern, a language known, a prior alarm, a prior gas event, a prior safety event, and a prior message. The assignment tags for identifying locations are programmed with information including one or more of a location within a space, a GPS location, an equipment at the location, a fuel source at the location, a known hazard at the location, a typical gas concentration for the location, an environmental condition for the location, a recent gas event, a recent man down alarm, a recent alarm, and a recent message. Triggering further comprises applying a filter based on the assignment tag's programmed information. The safety device is at least one of a multi-gas detection instrument and a gas detection instrument. The safety device is at least one of a respirator, a harness, a lighting device, a fall arrest device, a thermal detector, a flame detector, and a chemical, biological, radiological, nuclear, and explosives (CBRNE) detector. The safety event is a gas event.

In an aspect, a tangible article of manufacture having instructions stored thereon that, when executed, causes a machine to perform operations for tracking an operator and operator status using a safety device, the operations comprising: programming a plurality of NFC tags with assignment information, wherein the assignment information is at least one of a location assignment for NFC tags being placed at particular locations and an instrument operator assignment for tags distributed to safety device operators; receiving assignment information at the safety device when an NFC radio of the safety device is brought in proximity to at least one of the plurality of NFC tags; triggering a modification of a setting of the safety device based on the temporary assignment information; and communicating the modified setting to at least one other safety device in a mesh network with features as described herein for modification of a setting of the second safety device.

In an aspect, an alerting system includes a safety device comprising a GPS system; and an interface configured to: transmit the location of the safety device based on data from the GPS system to a remote server; receive alert information from the remote server in response to the remote server determining the location of the safety device corresponds to a hazardous location, wherein the remote server determines the hazardous location based on a condition detected from one or more of the safety device, a second safety device in an area within a pre-defined distance from the safety device, an area monitor, and third party data; and communicate the alert information to one or more devices in a mesh network with features as described herein joined by the safety device. The interface is a component of the safety device, a network gateway, or a smart phone.

In an aspect, an alerting system includes a safety device configured to read at least one of a plurality of location NFC tags comprising information regarding the location in which it is placed; and an interface configured to: transmit the location of the safety device based on the information from the location NFC tag to a remote server; and receive alert information from the remote server in response to the remote server determining the location of the safety device corresponds to a hazardous location, wherein the remote server determines the hazardous location based on a condition detected from one or more of the safety device, a second safety device in the location, an area monitor in the location, and third party data related to the location. The interface is a component of the safety device, a network gateway, or a smart phone. The interface is further configured to communicate the alert information to one or more devices in a mesh network joined by the safety device.

In an aspect, a computer-implemented method for providing real time locating and gas exposure monitoring includes receiving, by a computer processor, a first gas reading and a first location from a first device; receiving, by the computer processor, a second location from a second device; and transmitting one or more of an alert and the gas reading to the second device when the second location is within a predetermined distance from the first location and the gas reading exceeds a threshold, wherein the second device relays the alert and/or the gas reading to at least one peer device in a mesh network with features as described herein joined by the second device.

In an aspect, a computer-implemented method for providing real time locating and gas exposure monitoring includes receiving, by a computer processor, a first gas reading and a first location from a first device, wherein the first location is read from a location NFC tag in the location by the first device; receiving, by the computer processor, a second location from a second device; and transmitting one or more of an alert and the gas reading to the second device when the second location is within a predetermined distance from the first location and the gas reading exceeds a threshold. The second device relays the alert and/or the gas reading to at least one peer device in a mesh network with features as described herein joined by the second device.

In an aspect, a computer-implemented method for providing real time locating and gas exposure monitoring includes receiving, by a computer processor, a first safety event and a first location from a first device; receiving, by the computer processor, a second location from a second device; and transmitting an alert and the safety event to the second device when the second location is within a predetermined distance from the first location, wherein the second device relays the alert and/or the gas reading to at least one peer device in a mesh network with features as described herein joined by the second device.

In an aspect, a computer-implemented method for providing real time locating and gas exposure monitoring includes receiving, by a computer processor, a first safety event and a first location from a first device, wherein the first location is read from a location NFC tag in the location by the first device; receiving, by the computer processor, a second location from a second device; and transmitting an alert and the safety event to the second device when the second location is within a predetermined distance from the first location. The second device relays the alert and/or the gas reading to at least one peer device in a mesh network with features as described herein joined by the second device.

In an aspect, a system includes a plurality of portable environmental sensing devices in a work area adapted to communicate with one another in a mesh network with features as described herein; and a communications facility to transmit data from at least one of the plurality of portable environmental sensing devices to a remote computer, the remote computer configured to monitor at least one of a hazardous condition and an activation of a panic button in the work area based on data from the at least one of the plurality of portable environmental sensing devices, wherein the remote computer is configured to: receive, from the at least one portable environmental sensing device, an alarm related to the hazardous condition or activation of panic button, and transmit to any of the portable environmental sensing devices an instruction to be propagated throughout the mesh network. The instruction is a request to check the safety of a user of the at least one portable environmental sensing device, an evacuation instruction, a risk mitigation instruction, or the like. The remote computer is further configured to display the location of the portable environmental sensing devices in a map of the work area, wherein the remote computer transmits the map for display on the any of the portable environmental sensing devices. The data is sensed gas data, wherein the hazardous condition is based on the sensed gas data exceeding a threshold and the remote computer is further configured to display the sensed gas data in a map of the work area. A size of the representation of the gas data is proportional to the gas level. The remote computer is further configured to request an emergency response at the location of the at least one portable environmental sensing device.

In an aspect, a system for providing an ad-hoc mesh network with features as described herein for an eyewash station includes a sensor disposed within the eyewash station to monitor a condition, the sensor adapted to communicate with nodes in a mesh network; and a digital sign, wherein the digital sign is adapted to receive data related to the condition from the sensor through the mesh network for presentation.

In an aspect, a system for providing an ad-hoc mesh network with features as described herein for an eyewash station includes a sensor disposed within the eyewash station to monitor a condition, the sensor adapted to communicate with nodes in a mesh network; and a device in the mesh network configured to receive the communication from the sensor related to the condition and generate an alarm based on the condition meeting a threshold or criteria. The system further includes a digital sign in the mesh network, wherein the digital sign is adapted to receive the alarm from the device through the mesh network for presentation. The device in the mesh network is further configured to obtain one or more of a worker biometric datum and an area environmental datum. The device in the mesh network is further configured to transmit the alarm to a remote computer. The device in the mesh network is further configured to obtain an inventory of potential hazards from an NFC tag in the area near the eyewash station when an NFC radio of the device is brought in proximity to the NFC tag. A secondary alarm is generated based on at least one item in the inventory.

In an aspect, a method of sensing a root cause or symptom of death or injury of a worker on a worksite includes obtaining sensor data from one or more body worn sensors attached to the body of the worker, wherein the sensor data relates to one or more physiological and behavioral effects of the root cause of worker death or injury; analyzing the sensor data to identify a safety issue; and modifying an authorization level of the worker when the analyzed sensor data identifies a presence of the safety issue, wherein the authorization level is stored on a device of the worker.

In an aspect, a method of sensing a root cause or symptom of death or injury of a worker on a worksite includes obtaining sensor data from one or more body worn sensors attached to the body of the worker, wherein the sensor data relates to one or more physiological and behavioral effects of the root cause of worker death or injury; analyzing the sensor data to identify a safety issue; and when the analyzed sensor data identifies a presence of the safety issue, communicating the safety issue to a safety device of the worker for presentation on the safety device. The method further includes communicating the safety issue to a second safety device of a second worker for presentation, wherein the safety device and the second safety device are peers in a mesh network.

In an aspect, a method of sensing a root cause or symptom of death or injury of a worker on a worksite includes obtaining sensor data from one or more body worn sensors attached to the body of the worker, wherein the sensor data relates to one or more physiological and behavioral effects of the root cause of worker death or injury; analyzing the sensor data to identify a safety issue; and when the analyzed sensor data identifies a presence of the safety issue, communicating a request to check-in with the worker to a safety device of a second worker.

In an aspect, a system for providing a low-power ad-hoc mesh network with features as described herein for a remote jobsite includes a plurality of network devices comprising one or more worker monitoring devices and one or more area monitoring devices, wherein the network devices monitor at least one of a peer alarm, a worker biometric datum or an area environmental datum; and the network devices adapted to communicate with one another in a mesh network without a central network controller; wherein a first network device of the plurality of network devices transmits the peer alarm, the worker biometric datum or the area environmental datum to a second network device of the plurality of network devices for presentation on the second network device.

In an aspect, a system includes a plurality of network devices comprising one or more worker monitoring devices and one or more area monitoring devices, wherein the network devices monitor at least one of a peer alarm, a worker biometric datum or an area environmental datum, the network devices adapted to communicate with one another in a mesh network with features as described herein; and a network gateway, wherein the plurality of network devices transmits the peer alarm, the worker biometric datum or the area environmental datum to a remote computer through the gateway.

In an aspect, a system includes a plurality of network devices comprising one or more worker monitoring devices and one or more area monitoring devices, wherein the network devices monitor at least one of a peer alarm, a worker biometric datum or an area environmental datum, the network devices adapted to communicate with one another in a mesh network with features as described herein; and a device interface for a remote-networked device, wherein the plurality of network devices transmits the peer alarm, the worker biometric datum or the area environmental datum to the remote-networked device, wherein the remote-networked device is configured to further transmit the peer alarm, the worker biometric datum or the area environmental datum to a remote computer.

In an aspect, a method of sensing a root cause or symptom of death or injury of a worker on a worksite includes obtaining sensor data from one or more body worn sensors attached to the body of the worker, wherein the sensor data relates to one or more physiological and behavioral effects of the root cause of worker death or injury; analyzing the sensor data to identify a safety issue; and providing an alert to the worker or a third party when the analyzed sensor data identifies a presence of the safety issue. The alert is transmitted from the one or more body-worn sensors to a remote location via a network connection. The alert is transmitted directly from the one or more body-worn sensors to one or more workers located on the worksite. The step of analyzing the sensor data occurs within the body worn sensor. The sensor data is transmitted via a wireless network from the body-worn sensor to a remote location for analysis of the sensor data. The remote location communicates with the body-worn sensor to alert the worker wearing the body-worn sensor when the analyzed sensor data identifies the presence of the safety issue. The remote location communicates with the third party on the worksite to alert the third party that the analyzed sensor data indicates the presence of the safety issue related to the worker wearing the body-worn sensor. The physiological effects include an effect on at least one of ECG, heart rate, blood pressure, breathing rate, skin temperature, posture, activity, accelerometry, blood pressure, pulse, body odors, blood alcohol level, glucose levels, and oxygen saturation. The behavioral effects include an effect on at least one of gait, walking patterns, posture, eye movements, pupil size, motion patterns, noises, and removal of the sensor from the person before a prescribed time. The body-worn sensors comprise one or more of a heart rate sensor, blood pressure sensor, gait detection sensor, olfactory sensor, galvanic skin response sensor, proximity sensor, accelerometer, eye tracking sensor, image sensor, microphone, infrared sensor, gas sensor, capacitive sensor, fingerprint sensor, networking signal detector, and location detector. The method further includes the step of storing the sensor data and comparing current sensor data to stored sensor data to determine a variance indicating a safety issue. The method further includes the step of storing typical sensor data from a plurality of workers and comparing current sensor data for the worker to stored sensor data for the plurality of workers to determine a variance indicating a safety issue. The method further includes the step of preventing the worker from accessing a system after identifying a safety issue. The method further includes the step of suggesting a behavior change to the worker to avoid a safety issue.

In an aspect, a system for providing a low-power ad-hoc mesh network for a remote jobsite includes a plurality of network devices comprising one or more sensing devices and one or more area monitoring devices, wherein the network devices monitor at least one of a peer alarm, a worker biometric datum or an area environmental datum; the network devices adapted to communicate with one another in a mesh network with features as described herein; wherein a first network device of the plurality of network devices transmits the peer alarm, the worker biometric datum or the area environmental datum to a second network device of the plurality of network devices for presentation on the second network device.

In an aspect, a network for connecting a plurality of network nodes with features as described herein includes a leader node; and a plurality of follower nodes, wherein the leader node transmits a sync message to the plurality of follower nodes indicating a beginning of a network interval, wherein the leader node and the plurality of follower nodes transmit information during a transmission period of the network interval and do not transmit information during a sleep period of the network interval, the leader node and plurality of follower nodes using less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When any of the plurality of follower nodes receive a sync message, the follower node transmits a message advertising one or more properties of the leader node during a predetermined period of the network interval. The one or more properties of the leader node includes at least one of a channel hopping sequence and a total number of the network nodes on the network. When any one of the plurality of follower nodes fails to receive a receive a sync message from the leader node, the follower node refrains from transmitting a message advertising a property of the leader node during the network interval. Follower nodes each comprise a counter for tracking the receipt of sync message from the leader. The counter is incremented when a sync message is received and decremented when a sync message is not received. When the counter of any one of the follower nodes reaches a predetermined value, the follower node initiates a procedure for finding a new leader node. When the timer is further adapted to time an expected receipt of future sync messages of future network intervals and when an actual receipt of the future sync message deviates from an expected receipt of the future sync message by a predetermined amount of time for a predetermined number of network intervals, the follower node adjusts the timer to more closely correspond with the actual receipt of the future sync message. The sync message includes data indicating the number of network nodes in the network. The length of the transmission period is determined by the number of network nodes in the network. The network nodes are environmental sensing devices. The information is assigned by reading an NFC tag. The information relates to a concentration of gas or an environmental attribute. The network nodes are environmental sensing devices, and the one or more properties is assigned by reading an NFC tag.

In an aspect, a network for connecting a plurality of network nodes with features as described herein includes a leader node; and a plurality of follower nodes, wherein the leader node transmits a sync message to the plurality of follower nodes indicating a beginning of a network interval, wherein the leader node and the plurality of follower nodes transmit information during a transmission period and do not transmit information during a sleep period of the network interval, and wherein during a predetermined time of the transmission period of the network interval each of the follower nodes that received the sync message transmit a message advertising one or more properties of the leader node. The one or more properties of the leader node includes at least one of a channel hopping sequence and a total number of the network nodes on the network. When any of the plurality of follower nodes fails to receive a receive a sync message from the leader node, the follower node refrains from transmitting a message advertising a property of the leader node during the network interval. The message advertising a property of the leader node is broadcast on a predetermined subset of channels. A new follower node attempting to join the network listens on the predetermined subset of channels to receive the message advertising at least one property of the leader node to learn the at least one property of the leader node to facilitate the new follower node to join the network. At least one property comprises the total number of network nodes already on the network and the new follower node will refrain from attempting to join the network when the total number of network nodes exceeds a predetermined value. After a predetermined interval, the leader node refrains from sending the sync message and entering the sleep period for at least one network interval and listens for messages advertising at least one property of a different leader node. The leader node is a gas sensor. If the leader node receives a message advertising at least one property of the different leader node, the leader node starts a process to cease performing as the leader node and begin performing as a follower node of the different leader node. If the leader node does not receive a message advertising at least one property of another leader node, the leader node continues to perform as the leader node. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When the follower nodes transmit the message advertising the one or more properties of the leader node, the message is transmitted with a single hop such that a node receiving the message does not retransmit the message.

In an aspect, a method of operating a wireless mesh network with features as described herein includes the steps of: providing a plurality of nodes wherein each node is operable to perform as a leader node or a follower node, wherein one node performs to identify itself as the leader node and one or more other nodes operate as follower nodes; wherein the leader node transmits a sync message to follower nodes indicating a beginning of a network interval, wherein the leader node and the follower nodes transmit information during a transmission period and do not transmit information during a sleep period of the network interval, and wherein during a predetermined time of the transmission period of the network interval follower nodes that received the sync message transmit a message advertising one or more properties of the leader node. The one or more properties of the leader node includes at least one of a channel hopping sequence and a total number of the network nodes on the network. When any of the plurality of follower nodes fails to receive a receive a sync message from the leader node, the follower node refrains from transmitting a message advertising a property of the leader node during the network interval. The message advertising a property of the leader node is broadcast on a predetermined subset of channels. A new follower node attempting to join the network listens on the predetermined subset of channels to receive the message advertising at least one property of the leader node to learn the at least one property of the leader node to facilitate the new follower node to join the network. The at least one property comprises the total number of network nodes already on the network and the new follower node will refrain from attempting to join the network when the total number of network nodes exceeds a predetermined value. After a predetermined interval, the leader node refrains from sending the sync message and entering the sleep period for at least one network interval and listens for messages advertising at least one property of a different leader node. The leader node is a gas sensor. If the leader node receives a message advertising at least one property of the different leader node, the leader node starts a process to cease performing as the leader node and begin performing as a follower node of the different leader node. If the leader node does not receive a message advertising at least one property of another leader node, the leader node continues to perform as the leader node. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When the follower nodes transmit the message advertising the one or more properties of the leader node, the message is transmitted with a single hop such that a node receiving the message does not retransmit the message.

In an aspect, a network with features as described herein for connecting a plurality of network nodes comprising: a first leader node; and a plurality of follower nodes, wherein the first leader node transmits a sync message to the plurality of follower nodes indicating a beginning of a network interval, wherein the plurality of follower nodes transmit information during a transmission period and do not transmit information during a sleep period of the network interval, and wherein during a predetermined time of the transmission period of the network interval each of the follower nodes that received the sync message transmit a message advertising one or more properties of the first leader node; and wherein transmission period, the first leader nodes listens for information advertising one or more properties of a second leader node. The message advertising a property of the second leader node is transmitted on a predetermined channel. The first leader node listens on the predetermined channel. The message advertising a property of the second leader node is also transmitted on a second predetermined channel. The first leader node also listens on the second predetermined channel. The first leader node listens for a period of time greater than the length of the network interval. When the first leader node receives for information advertising one or more properties of a second leader node, the first leader node ceases performing as a leader node and is adapted to begin a sequence to join the second leader node as a follower node. The plurality of follower nodes are adapted to detect an absence of the first leader node and begin a sequence to join a new leader node. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. The network nodes are environmental sensing devices. The information is assigned by reading an NFC tag. The information relates to a concentration of gas. The information relates to an environmental attribute. The one or more properties is assigned by reading an NFC tag.

In an aspect, a network with features as described herein for connecting a plurality of network nodes comprising: a leader node; and a plurality of follower nodes, wherein the leader node transmits a sync message to the plurality of follower nodes indicating a beginning of a network interval, wherein the plurality follower nodes each comprise a counter for tracking the receipt of sync messages received from the leader node and the counter is incremented when a sync message is received and decremented when a sync message is not received, wherein any of the plurality of follower nodes will begin a process of electing new leader node when the counter decreases to a predetermined value. The leader node and the plurality of follower nodes transmit information during a transmission period and do not transmit information during a sleep period of the network interval. The follower node whose counter has decremented to the predetermined value transmits a first nominate message to begin the process of electing a new leader node. The first nominate message is transmitted on a predetermined channel. The first nominate message is also transmitted on a second predetermined channel. The first nominate message includes data related to the suitability of the follower node sending the first nominate message to act as a leader node. The data is calculated from a strength and reliability of signals received from other network nodes on the network. The data is calculated by utilizing at least one of an instrument type of the follower node, a battery state of charge, and past signal quality. The first nominate message and data are received by other network nodes and the data compared by the receiving network nodes to data related to a suitability of the receiving network nodes to act as a leader node, wherein the receiving network nodes reply with either a reply nominate message with data indicating a higher suitability to act as a leader node or a concede message if the receiving network node does not have a higher suitability to act as a leader node. When the follower node sending the first nominate message receives only concede messages, that follower node assumes the role of leader node and advertises at least one property of itself as a leader node for other network nodes to become follower nodes. When the follower node sending the first nominate message receives a nominate message with data indicating a higher suitability to act as a leader node, that follower node sends a concede message. The concede messages are transmitted on the predetermined channel. The concede messages are also transmitted on the second predetermined channel.

In an aspect, a network with features as described herein for connecting a plurality of network nodes comprising: a leader node; and a plurality of follower nodes, wherein the leader node transmits sync message to the plurality of follower nodes indicating a beginning of successive network intervals, wherein upon nonreceipt of a predetermined number of sync messages by a follower node that follower node initiates a process of electing a new leader node by a sending a first nominate message that includes data related to the suitability of the follower node to act as a leader node. The plurality of follower nodes each comprise a counter for tracking the receipt of sync messages received from the leader node and the counter is incremented when a sync message is received and decremented when a sync message is not received, wherein any of the plurality of follower nodes will begin a process of electing new leader node when the counter decreases to the predetermined value. The first nominate message is transmitted on a predetermined channel. The first nominate message is also transmitted on a second predetermined channel. The data is calculated from a strength and reliability of signals received from other network nodes on the network. The data is calculated by utilizing at least one of an instrument type of the follower node, a battery state of charge, and past signal quality. The first nominate message and data are received by other network nodes and the data compared by the receiving network nodes to data related to a suitability of the receiving network nodes to act as a leader node, wherein the receiving network nodes reply with either a reply nominate message with data indicating a higher suitability to act as a leader node or a concede message if the receiving network node does not have a higher suitability to act as a leader node. When the follower node sending the first nominate message receives only concede messages, that follower node assumes the role of leader node and advertises at least one property of itself as a leader node for other network nodes to become follower nodes. When the follower node sending the first nominate message receives a nominate message with data indicating a higher suitability to act as a leader node, that follower node sends a concede message. The concede messages are transmitted on the predetermined channel. The concede messages are also transmitted on the second predetermined channel. The network nodes are environmental sensing devices. The information is assigned to the node by reading an NFC tag. The information relates to a concentration of gas. The information relates to an environmental attribute. The network nodes are environmental sensing devices.

In an aspect, a method of providing information about a leader node to a plurality of follower nodes in a wireless mesh communication network with features as described herein comprising: designating the leader node; designating the plurality of follower nodes; designating one or more predetermined frequency ranges as a public channel; from the leader node and during a plurality of network intervals having a predetermined length of time, transmitting a sync message at a beginning of each network interval to the plurality of follower nodes; and during each network interval in which a sync message is received by any one of the follower nodes, transmitting from any of the plurality of follower node receiving a sync message, upon the least one public channel, a message advertising at least one property of the leader node after receipt of the sync message. The leader node also sends a message advertising at least one property of the leader node in any network interval in which a sync message is transmitted. The method may further include providing a new follower node not yet configured to receive the sync message; with the new follower node, listening to the public channel until the at least one property of the leader node is broadcast; and from the at least one property, causing the new follower node to configure itself to communicate with the leader node on the next network cycle to join the network. The at least one property of the leader node comprises at least one of frequency hop parameters and the total number of leader and follower nodes on the network. The at least one property of the leader node comprises frequency hop parameters comprising a multiplier, an intercept and a seed for linear congruent generator. The frequency hop parameters further comprise channel mask parameters defining predetermined channels as either one of used and unused. The frequency hop parameters further comprise a length of time for the network interval. The at least one property of the leader node comprises the total number of leader and follower nodes on the network and wherein the new follower node will not attempt to join the network if the total exceeds a predetermined value. The leader node and follower nodes are environmental sensing devices.

In an aspect, a method of joining a new device to a mesh wireless network with features as described herein comprising: providing a mesh wireless network comprising a leader node and a plurality of follower nodes; designating at least one predetermined frequency range as a public channel; transmitting on the public channel information advertising at least one property of the leader node; with a new device to the mesh wireless network, listening on the public channel for the information transmitted advertising at least one property of the leader node; configuring the new device to follow the leader device using the at least one advertised property describing the leader node; with the new device to the mesh wireless network, receiving a sync message transmitted from the leader node; and requesting the leader node to join the mesh wireless network. The step of transmitting on the public channel information advertising at least one property of the leader node is performed by at least one of the follower nodes in response to receipt of a sync message. The step of transmitting on the public channel information advertising at least one property of the leader node is performed by the leader node after transmission of a sync message. The at least one property of the leader node comprises at least one of frequency hop parameters and the total number of leader and follower nodes on the network. The at least one property of the leader node comprises frequency hop parameters comprising a multiplier, an intercept and a seed for linear congruent generator. The frequency hop parameters further comprise channel mask parameters defining predetermined channels as either one of used and unused. The frequency hop parameters further comprise a length of time for the network interval. The at least one property of the leader node comprises the total number of leader and follower nodes on the network and wherein the new follower node will not attempt to join the network if the total exceeds a predetermined value.

In an aspect, a method of joining a follower node to a leader node in a wireless mesh communication network with features as described herein comprising: designating the leader node; designating the plurality of follower nodes; designating one or more predetermined frequency ranges as a public channel; from the leader node and during a plurality of network intervals having a predetermined length of time, transmitting a sync message at a beginning of each network interval to the plurality of follower nodes; during each network interval in which a sync message is received by any one of the follower nodes, transmitting from any of the plurality of follower nodes receiving a sync message, upon the least one public channel, a message advertising at least one property of the leader node after receipt of the sync message; providing a new follower node not yet configured to receive the sync message; with the new follower node, listening to the public channel until the at least one property of the leader node is broadcast and received by the new follower node; and from the at least one property, causing the new follower node to configure itself to communicate with the leader node on the next network cycle to join the network. The method further includes providing a new follower node not yet configured to receive the sync message; with the new follower node, listening to the public channel until the at least one property of the leader node is broadcast; and from the at least one property, causing the new follower node to configure itself to communicate with the leader node on the next network cycle to join the network. The at least one property of the leader node comprises at least one of frequency hop parameters and the total number of leader and follower nodes on the network. The at least one property of the leader node comprises frequency hop parameters comprising a multiplier, an intercept and a seed for linear congruent generator. The frequency hop parameters further comprise channel mask parameters defining predetermined channels as either one of used and unused. The frequency hop parameters further include a length of time for the network interval. The at least one property of the leader node comprises the total number of leader and follower nodes on the network and wherein the new follower node will not attempt to join the network if the total exceeds a predetermined value. The leader node is an environmental sensing device. The devices are environmental sensing devices. The leader node and follower nodes are environmental sensing devices.

In an aspect, a network with features as described herein for connecting a plurality of network nodes comprising: a leader node; and a plurality of follower nodes, wherein the leader node transmits a sync message to the plurality of follower nodes indicating a beginning of a network interval, wherein the sync message contains data indicating the number of network nodes in the network, wherein the leader node and the plurality of follower nodes transmit information during a transmission period of the network interval and do not transmit information during a sleep period of the network interval, wherein the network interval is of a fixed length of time, the transmission period is of a variable length of time based upon the number of network nodes in the network, and the sleep period comprises remaining time of the network interval after the transmission period. The transmit time is divided between a first transmit time for transmitting high priority data and a second transmit time for lower prior data. The first transmit time and the second transmit time are equal length periods of time. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When any of the plurality of follower nodes receive a sync message, the follower node transmits a message advertising one or more properties of the leader node during a predetermined period of the network interval. The one or more properties of the leader node includes at least one of a channel hopping sequence and a total number of the network nodes on the network. When the timer is further adapted to time an expected receipt of future sync messages of future network intervals and when an actual receipt of the future sync message deviates from an expected receipt of the future sync message by a predetermined amount of time for a predetermined number of network intervals, the follower node adjusts the timer to more closely correspond with the actual receipt of the future sync message. The network nodes are environmental sensing devices. The information is assigned to the node by reading an NFC tag. The information relates to a concentration of gas. The information relates to an environmental attribute.

In an aspect, a network with features as described herein for connecting a plurality of network nodes comprising: a leader node; and a plurality of follower nodes, wherein the leader node transmits a successive plurality of sync messages to the plurality of follower nodes indicating a beginning of successive network intervals, wherein the leader node and the plurality of follower nodes transmit information during a transmission period of each network interval and wherein the leader node changes a channel of the sync message in subsequent network intervals according to a channel change schedule and wherein the plurality of follower nodes change a channel to receive the sync messages of successive network intervals according to the same channel change schedule, and leader node does not change a channel of transmission during the transmission period of the network interval. The channel change schedule changes the channel for each successive network interval. The channel change schedule changes the channel after a plurality of network intervals. The channel change schedule is changed according to a linear congruential generator. When any of the plurality of follower nodes receive a sync message, the follower node transmits a message advertising one or more properties of the channel change schedule. The channel change schedule is changed according to a linear congruential generator. The one or more properties of the channel change schedule comprises a seed, a multiplier and an intercept for the linear congruential generator. The channel change schedule further indicates channels that are unavailable to broadcast the sync message. The channel change schedule further indicates channels that are available to broadcast the sync message. The network nodes are environmental sensing devices. The information is assigned to the node by reading an NFC tag. The information relates to a concentration of gas. The information relates to an environmental attribute.

In an aspect, a static memory device comprising: an instrument comprising at least one of an environmental sensing device, a hazard detection device, and an industrial safety device, the instrument operating in a first sleep cycle in which the instrument is generating data related to the instrument type; a wireless radio for sending and receiving information on a wireless mesh network with features as described herein, the radio operating a second sleep cycle different from the first sleep cycle in at least one of period and phase; and a shared memory operatively connected to the instrument and the radio, the shared memory comprising static message memory comprising static messages related to the instrument; an outgoing memory portion that receives outgoing information from the instrument and transmits the outgoing information to the radio for transmission on the wireless mesh network, an incoming memory portion that receives incoming information from the radio and transmits the incoming information to instrument, the shared memory further comprising request and grant lines for the radio and for the instrument to allow the radio and the instrument to request and grant data to the incoming memory or the outgoing memory, wherein the shared memory is adapted to not allow the both the radio and the instrument to raise the grant lines and grant data to either the incoming or the outgoing memory simultaneously. The device further includes a radio internal buffer for providing additional memory space to the radio. The first and second sleep cycles differ in both period and phase. The shared memory further comprises an urgent line that provides an indicator to the instrument or the radio that the information in outgoing or incoming memory portion should be accessed immediately. The information is assigned to the node by reading an NFC tag. The information relates to a concentration of gas. The information relates to an environmental attribute.

In an aspect, a network for connecting a plurality of network nodes comprising: a static memory device comprising: an instrument comprising at least one of an environmental sensing device, a hazard detection device, and an industrial safety device, the instrument operating in a first sleep cycle in which the instrument is generating data related to the instrument type; a wireless radio for sending and receiving information on a wireless mesh network with features as described herein, the radio operating a second sleep cycle different from the first sleep cycle in at least one of period and phase; and a shared memory operatively connected to the instrument and the radio, the shared memory comprising static message memory comprising static messages related to the instrument; an outgoing memory portion that receives outgoing information from the instrument and transmits the outgoing information to the radio for transmission on the wireless mesh network, an incoming memory portion that receives incoming information from the radio and transmits the incoming information to instrument, the shared memory further comprising request and grant lines for the radio and for the instrument to allow the radio and the instrument to request and grant data to the incoming memory or the outgoing memory, wherein the shared memory is adapted to not allow the both the radio and the instrument to raise the grant lines and grant data to either the incoming or the outgoing memory simultaneously; and a wireless mesh network communicating with the radio comprising: a leader node; and a plurality of follower nodes, wherein the leader node transmits a sync message to the plurality of follower nodes indicating a beginning of a network interval, wherein the leader node and the plurality of follower nodes transmit information during a transmission period of the network interval and do not transmit information during a sleep period of the network interval, the leader node and plurality of follower nodes using less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. The network further includes a radio internal buffer for providing additional memory space to the radio. The first and second sleep cycles differ in both period and phase. The shared memory further comprises an urgent line that provides an indicator to the instrument or the radio that the information in outgoing or incoming memory portion should be accessed immediately. The information is assigned to the node by reading an NFC tag. The information relates to a concentration of gas. The information relates to an environmental.

In an aspect, a mesh network device for connecting to, sending and receiving information on a mesh wireless network with features as described herein comprising: an instrument comprising at least one of an environmental sensing device, a hazard detection device, and an industrial safety device, a radio for transmitting and receiving information on the mesh wireless network; and a display for presenting a signal quality indicator of a connection of the radio to other nodes of the mesh wireless network, the signal quality indicator derived from a combination of the received signal strength (RSS) and packet receive ratio (PRR) of all the instruments in the mesh wireless network. The instrument multiplies an RSS of a most recent message received from each node in the mesh network by the PRR, which is the ratio of packets received from each device in the mesh wireless network to a number of expected packets from each respective device in the mesh wireless network. The RSS represents a most recent network hop taken by a packet. The PRR is a counter that begins at a predetermined number and is incremented and decremented when expected packets are received or not received, respectively. The increment and decrement values are 3 and 2, respectively. The signal quality indicator is based on the product of RSS*PRR for each node, summed and divided by a number of nodes in the network. An alarm sounds when the signal quality indicator drops below a predetermined level. The information is assigned to the node by reading an NFC tag. The information relates to a concentration of gas. The information relates to an environmental attribute.

In an aspect, a network with features as described herein for connecting a plurality of network nodes comprising: a leader node; and a plurality of follower nodes, wherein the leader node transmits a sync message to the plurality of follower nodes indicating a beginning of a network interval, wherein the sync message contains data indicating the number of network nodes in the network, wherein the leader node and the plurality of follower nodes transmit information during a transmission period of the network interval and do not transmit information during a sleep period of the network interval, wherein each of the plurality of the follower nodes randomly select an interval during the transmission period to transmit data and without respect to a time selected by any of the other follower nodes. The time randomly selected is with reference to beginning of the transmission period. The network interval is of a fixed length of time, the transmission period is of a variable length of time based upon the number of network nodes in the network, and the sleep period comprises remaining time of the network interval after the transmission period. The transmission period is divided between a first transmit time for transmitting high priority data and a second transmit time for lower prior data and wherein the time randomly selected to transmit data is with reference to the beginning of the first transmit time and the second transmit time. The first transmit time and the second transmit time are equal length periods of time. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When any of the plurality of follower nodes receive a sync message, the follower node transmits a message advertising one or more properties of the leader node during a predetermined period of the network interval. The one or more properties of the leader node includes at least one of a channel hopping sequence and a total number of the network nodes on the network. When the timer is further adapted to time an expected receipt of future sync messages of future network intervals and when an actual receipt of the future sync message deviates from an expected receipt of the future sync message by a predetermined amount of time for a predetermined number of network intervals, the follower node adjusts the timer to more closely correspond with the actual receipt of the future sync message. The network nodes are environmental sensing devices. The information is assigned to the node by reading an NFC tag. The information relates to a concentration of gas. The information relates to an environmental attribute.

In an aspect, a network with features as described herein for connecting a plurality of network nodes comprising: a leader node; and a plurality of follower nodes, wherein the leader node transmits a sync message to the plurality of follower nodes indicating a beginning of a network interval, wherein the sync message contains data indicating the number of network nodes in the network, wherein the leader node and the plurality of follower nodes transmit information during a transmission period of the network interval and do not transmit information during a sleep period of the network interval, wherein the transmission period is divided between a first transmit time for transmitting high priority data and a second transmit time for transmitting lower prior data. Each of the plurality of the follower nodes randomly select an interval during the transmission period to transmit data and without respect to a time selected by any of the other follower nodes and wherein the time randomly selected to transmit data is with reference to the beginning of the first transmit time and the second transmit time. The network interval is of a fixed length of time, the transmission period is of a variable length of time based upon the number of network nodes in the network, and the sleep period comprises remaining time of the network interval after the transmission period. The first transmit time and the second transmit time are equal length periods of time. The leader node and plurality of follower nodes use less power in the sleep period than the transmission period, the plurality of follower nodes each comprising a timer, the timer adapted to time the transmission period and sleep period of a plurality of future network intervals in an absence of continued receipt of the sync message from the leader node during the plurality of future network intervals. When any of the plurality of follower nodes receive a sync message, the follower node transmits a message advertising one or more properties of the leader node during a predetermined period of the network interval. The one or more properties of the leader node includes at least one of a channel hopping sequence and a total number of the network nodes on the network. When the timer is further adapted to time an expected receipt of future sync messages of future network intervals and when an actual receipt of the future sync message deviates from an expected receipt of the future sync message by a predetermined amount of time for a predetermined number of network intervals, the follower node adjusts the timer to more closely correspond with the actual receipt of the future sync message. The network nodes are environmental sensing devices. The information is assigned to the node by reading an NFC tag. The information relates to a concentration of gas. The information relates to an environmental attribute.

In an aspect, a catalytically activated combustible gas sensing element may include a filament of resistance wire forming a coil, wherein a first end of the resistance wire is attached to a first support post and a second end of the resistance wire is attached to a second support post, a cantilever support supporting the coil, wherein the cantilever support is attached to a third support post, and a catalytic bead substantially surrounding the coil and cantilever. The resistance wire may be coated via chemical vapor deposition with an insulating material preventing winds of the coil from electrically conducting through an exterior surface of the wire. The cantilever support may be attached to the resistance wire, such as by soldering. It may be attached to a single coil of the resistance wire, to more than one but not all coils of the resistance wire, or to all coils of the resistance wire. The cantilever support may be disposed within, but does not contact the resistance wire. The cantilever support may be disposed below the resistance wire or above the resistance wire. The gas sensing element may further include a bead enveloping the cantilever support and the resistance wire. The bead may include a catalytic material, such as one or both of platinum or palladium, or a ceramic material. The bead may include an inner layer of a porous oxide-supported precious metal catalyst and an outer layer of a porous oxide-supported catalytic material.

In an aspect, a catalytically activated combustible gas sensing element may include a filament of resistance wire forming a coil, wherein the resistance wire is of a diameter equal to or less than 0.5 millimeters, wherein a first end of the resistance wire is attached to a first support post and a second end of the resistance wire is attached to a second support post; and a cantilever support adapted to support the coil, wherein the cantilever support is attached to a third support post; wherein the resistance wire can withstand more than eight drops of one meter onto concrete without breakage. The cantilever support is attached to the resistance wire. It may be attached to a single coil of the resistance wire, to more than one but not all coils of the resistance wire, or to all coils of the resistance wire. The cantilever support may be disposed within, but does not contact the resistance wire. The cantilever support may be disposed below the resistance wire or above the resistance wire. The gas sensing element may further include a bead enveloping the cantilever support and the resistance wire. The bead may include a catalytic material, such as one or both of platinum or palladium, or a ceramic material. The bead may include an inner layer of a porous oxide-supported precious metal catalyst and an outer layer of a porous oxide-supported catalytic material.

In an aspect, a portable electrochemical gas sensing apparatus may include a housing comprising an exterior surface that defines an interior space, wherein at least one depression is formed in the exterior surface; an electrochemical gas sensor at least partially disposed within the at least one depression of the housing; and a processing unit disposed in the interior space of the housing and in electrical communication with the electrochemical gas sensor. The components of the electrochemical gas sensor may include an electrode stack, wherein the electrode stack comprises at least one gas permeable membrane, at least one electrolyte absorption pad, at least one measuring electrode, and at least one counter electrode. The at least one depression may include a first reservoir, a second reservoir, and a centrally-disposed raised platform formed within the at least one depression of the exterior surface, and the platform is shaped to support, at least in part, the electrode stack. The electrode stack may rest on the raised platform and covers the second reservoir. The second reservoir may be adapted to hold an electrolyte solution that is in fluid communication with the electrode stack. The electrode stack may be in electrical communication with an alarm modality, wherein the alarm modality is disposed in the interior space of the housing. The alarm modality is wirelessly connected to the processing unit. The apparatus may further include a cap sized to fit over the at least one depression. The cap includes a capillary hole providing access for gas entry into the electrode stack. The electrochemical sensor senses one or more of: oxygen, carbon monoxide, methane, and hydrogen sulfide. The interior space of the housing is sealed. The apparatus may further include a power source disposed in the interior space of the housing to power the alarm modality.

In an aspect, a portable combustible lower explosive limit (LEL) gas sensing apparatus may include a housing comprising an exterior surface and that defines an interior space, wherein at least one depression is formed in the exterior surface; a combustible gas sensor at least partially disposed within the at least one depression of the housing; and a processing unit disposed in the interior space of the housing and in electrical communication with the combustible gas sensor. The at least one depression holds at least one catalytic sensing bead in a chamber. The at least one catalytic sensing bead is in electrical communication with components of the apparatus disposed in the interior space. The at least one depression includes two chambers with an chamber separator integrally formed in the depression, wherein each chamber is adapted to hold at least one catalytic sensing bead. The apparatus may further include a sensor flame arrestor that covers the at least one depression. The apparatus may include a gas sensing element including an electric heating element, a first layer coated on the electric heating element and comprising a precious metal catalyst supported on a porous oxide, the precious metal catalyst catalyzing combustion of a combustible gas to be detected by the sensing element, and a second layer overlaying the first layer, and comprising a catalytic compound capable of trapping gases that poison the precious metal catalyst, said catalytic compound being supported on a porous oxide; a compensating element comprising an electric heating element, said compensating element not including a catalyst capable of catalyzing combustion of a combustible gas to be detected by the sensing element; and a processing unit to which the sensing element and compensating element are connected, the processing unit being constructed and arranged to detect changes in resistance of the sensing element and compensating element, and to provide a reading of said changes. The catalytic materials for the first and second layers may include one or more of oxide-supported metal oxides supported on porous oxide supports, solid acids, solid bases, and metal-loaded zeolites and clays. The apparatus may further include at least one reference electrode.

In an aspect, a circuit for tuning an unbalanced Wheatstone bridge circuit in a combustible catalytic gas sensor to minimize baseline voltage drift may include a first branch comprising a sensor bead in series with a compensating bead wherein the temperature and resistance of the sensing bead increases in comparison to the compensating bead when in the presence of a combustible gas, a second branch, connected in parallel with the first branch, comprising two resistors; a meter to measure a baseline voltage differential between the two branches connected between the beads on the first branch and between the two resistors on the second branch; and one or more variable resistor in parallel with each of or both of the sensor bead and the compensating bead; wherein the one or more variable resistors may be adjusted to maintain the baseline voltage differential as indicated by the meter at about zero volts. The one or more variable resistor in parallel with each of or both of the sensor bead and the compensating bead may include a variable resistor in parallel with the sensing bead and a variable resistor in parallel with the compensating bead. The one or more variable resistor in parallel with each of or both of the sensor bead and the compensating bead may include a variable resistor in parallel with sensing bead. The one or more variable resistor in parallel with each of or both of the sensor bead and the compensating bead consists of a variable resistor in parallel with the compensating bead.

In an aspect, a circuit for tuning an unbalanced Wheatstone bridge circuit in a combustible catalytic gas sensor to minimize baseline voltage drift including a first branch may include a sensor bead in series with a compensating bead wherein the temperature and resistance of the sensing bead increases in comparison to the compensating bead when in the presence of a combustible gas, a second branch, connected in parallel with the first branch, comprising a first and a second resistance; a meter to measure a baseline voltage differential between the two branches connected between the beads on the first branch and between the two resistors on the second branch; and wherein the first resistance comprises one of a variable resistor or a fixed resistor in parallel with a variable resistor; and wherein the second resistance comprises one of a variable resistor or a fixed resistor in parallel with a variable resistor, but wherein the first resistance or second resistance comprises at least one variable resistor; wherein the at least one variable resistor may be adjusted to maintain the baseline voltage differential as indicated by the meter at about zero volts. The first resistance may include a fixed resistor. The first resistance may include a fixed resistor in parallel with a variable resistor. The second resistance may include a variable resistor. The second resistance may include a fixed resistor in parallel with a variable resistor.

In an aspect, a circuit for tuning an unbalanced Wheatstone bridge circuit in a combustible catalytic gas sensor to minimize baseline voltage drift may include a first branch comprising a sensor bead in series with a compensating bead wherein the temperature and resistance of the sensing bead increases in comparison to the compensating bead when in the presence of a combustible gas, a second branch comprising a potentiometer comprising a first and a second leg having a first and second resistance, respectively, the first resistance in parallel with the sensor bead and the second resistance in parallel with the compensating bead; and a meter to measure a baseline voltage differential between the two branches connected between the beads on the first branch and between the first and second leg of the potentiometer; wherein the potentiometer is adjusted to maintain the baseline voltage differential as indicated by the meter at about zero volts. The circuit may further include one or both of a primary resistor in parallel with the first leg of the potentiometer and a secondary resistor in parallel with the second leg of the potentiometer. The circuit may further include one or both of a primary resistor in series with the first leg of the potentiometer and a secondary resistor in series with the second leg of the potentiometer. The circuit may further include a microprocessor, wherein the meter comprises an analog to digital convertor for providing the baseline voltage differential between the two branches to the microprocessor and potentiometer comprises a digitally controlled potentiometer controlled by the microprocessor for varying the first and second resistances of the first and second legs of the digital potentiometer.

In an aspect, a process for manufacturing a hydrogen sulfide filter for use with a catalytic bead gas sensor may include preparing a solution of a copper compound; applying the solution of copper compound to a glass fiber paper; drying the glass fiber paper; preparing a solution of sodium borohydride; applying the solution of sodium borohydride to the copper compound on the glass fiber paper; and drying the glass fiber paper. The copper compound is one of copper chloride and copper sulfate.

In an aspect, a process for manufacturing a hydrogen sulfide filter for use with a catalytic bead gas sensor may include preparing a solution of a copper compound; applying the solution of the copper compound to a glass fiber paper; drying the glass fiber paper; and applying hydrogen in nitrogen to the glass fiber paper. The copper compound is one of copper chloride and copper sulfate.

In an aspect, a process for manufacturing a hydrogen sulfide filter for use with a catalytic bead gas sensor may include preparing a solution of a copper compound; preparing a solution of sodium borohydride; mixing the solutions of the copper compound and sodium borohydride; and drying the resulting metallic copper particles. The copper compound is one of copper chloride and copper sulfate.

In an aspect, a filter for use with a catalytic bead sensor may include particulate metallic copper, wherein the sizes of the metallic copper particles are predominantly between 1 nm and 100 nm and a substrate to support the particulate metal copper. The substrate may include at least one of glass fiber paper, alumina, silica, zirconia, and titanium. The substrate may be coated with the particulate metal copper.

In an aspect, a filter for use with a catalytic bead sensor may include an assembly of particulate metallic copper dried to form a shape suitable for use as a filter, wherein the sizes of the metallic copper particles are predominantly between 1 nm and 100 nm.

In an aspect, a hydrogen sulfide filter for use with a catalytic bead sensor may include a metal not comprising lead wherein the sensor sensitivity to methane remains above 0.65 mV/% LEL for greater than 20,000 seconds. The metal may include a metallic copper.

In an aspect, a hydrogen sulfide filter for use with a catalytic bead sensor may include a metal not comprising lead wherein the sensor capacity to hydrogen sulfide is greater than 550 parts per million hours. The metal may include a metallic copper. The sensor capacity to hydrogen sulfide may be greater than 600 parts per million hours, 650 parts per million hours, 700 parts per million hours, or 750 parts per million hours.

In an aspect, a device for determining a heat index may include a housing, which in embodiments may be adapted to be attached to the human, the housing including a temperature sensor; a humidity sensor; a microprocessor in communication with the temperature sensor and the humidity sensor; and at least two microphones, the microphones arranged to provide a first and second signal, respectively, to the microprocessor for determining an estimated wind speed; wherein the microprocessor, based upon data communicated from the temperature sensor and the humidity sensor and from the estimated wind speed, is configured to calculate a heat index and wherein the microprocessor provides a notification signal to alert when the heat index is determined to be excessive. The device includes at least three microphones. The temperature sensor, humidity sensor and microphones may all be solid-state. The housing further includes or the device is at least one of a portable or area environmental sensing device, a portable or area gas sensor, a portable or area multi-gas detection instrument, a respirator, a lighting device, a fall arrest device, a thermal detector, a flame detector, and a chemical, biological, radiological, nuclear, and explosives (CBRNE) detector. The housing further includes an electrochemical gas sensor at least partially disposed within the housing comprising an electrode stack, wherein the electrode stack comprises at least one gas permeable membrane, at least one electrolyte absorption pad, at least one measuring electrode, at least one counter electrode, and at least one reference electrode, the circuit in communication with the microprocessor to provide a signal related to the presence of one or more particular gases and the microprocessor adapted to provide an alarm related to an excessive level of one or more of the particular gases. The housing further includes a combustible gas sensor at least partially disposed within the housing comprising at least one catalytic sensing bead in a chamber, the combustible gas sensor in communication with the microprocessor to provide a signal related to the presence of one or more combustible gases and the microprocessor adapted to provide an alarm related to an excessive level of the one or more combustible gases. The wind speed is at least one of a maximum wind speed, an instantaneous wind speed, and an average wind speed. The alert is an audible alarm to the human based on the calculated heat index. The alert is an electronic communication transmitted to a remote location based on the calculated heat index.

In an aspect, a method of protecting a human or device from exposure to excessive heat may include providing a housing, optionally adapted to be attached to the human, the housing including a temperature sensor; a humidity sensor; at least two microphones; and a microprocessor; with the microprocessor calculating a wind speed from a signal received from the at least two microphones; with the microprocessor calculating a heat index based upon data received from the temperature sensor, humidity sensor and from the wind speed; and providing an alert when the calculated heat index is determined to be excessive. The at least two microphones include at least three microphones. The temperature sensor, humidity sensor and microphones may all be solid-state. The microprocessor may further be electrically connected to one of a portable or area environmental sensing device, a portable or area gas sensor, a portable or area multi-gas detection instrument, a respirator, a lighting device, a fall arrest device, a thermal detector, a flame detector, and a chemical, biological, radiological, nuclear, and explosives (CBRNE) detector. The method may further include the steps of: providing an electrochemical gas sensor at least partially disposed within the housing comprising an electrode stack, wherein the electrode stack comprises at least one gas permeable membrane, at least one electrolyte absorption pad, at least one measuring electrode, at least one counter electrode, and at least one reference electrode; providing a signal from the electrochemical gas sensor to the microprocessor related to the presence of one or more particular gases; and with the microprocessor, providing an alarm signal when the signal from the electrochemical gas sensor indicates an excessive level of one or more of the particular gases. The method may further include the steps of: providing a combustible gas sensor at least partial disposed within the housing comprising at least one catalytic sensing bead in a chamber, providing a signal from the combustible gas sensor to the microprocessor related to the presence of one or more combustible gases; and with the microprocessor, providing an alarm signal when from the combustible gas sensor indicates an excessive level of one or more combustible gases. The wind speed is at least one of a maximum wind speed, an instantaneous wind speed, and an average wind speed. The alert is an audible alarm to the human based on the calculated heat index. The alert is an electronic communication transmitted to a remote location based on the calculated heat index.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 6A depicts a list of instruments on a display.

FIG. 6B depicts a shadow gas display.

FIG. 13 depicts the wireless network fitting in a 7-layer OSI Model.

FIG. 39B depicts the coil resting on the cantilever.

FIG. 39C depicts the cantilever touching an inside surface of the coil.

DETAILED DESCRIPTION

Figure 1:
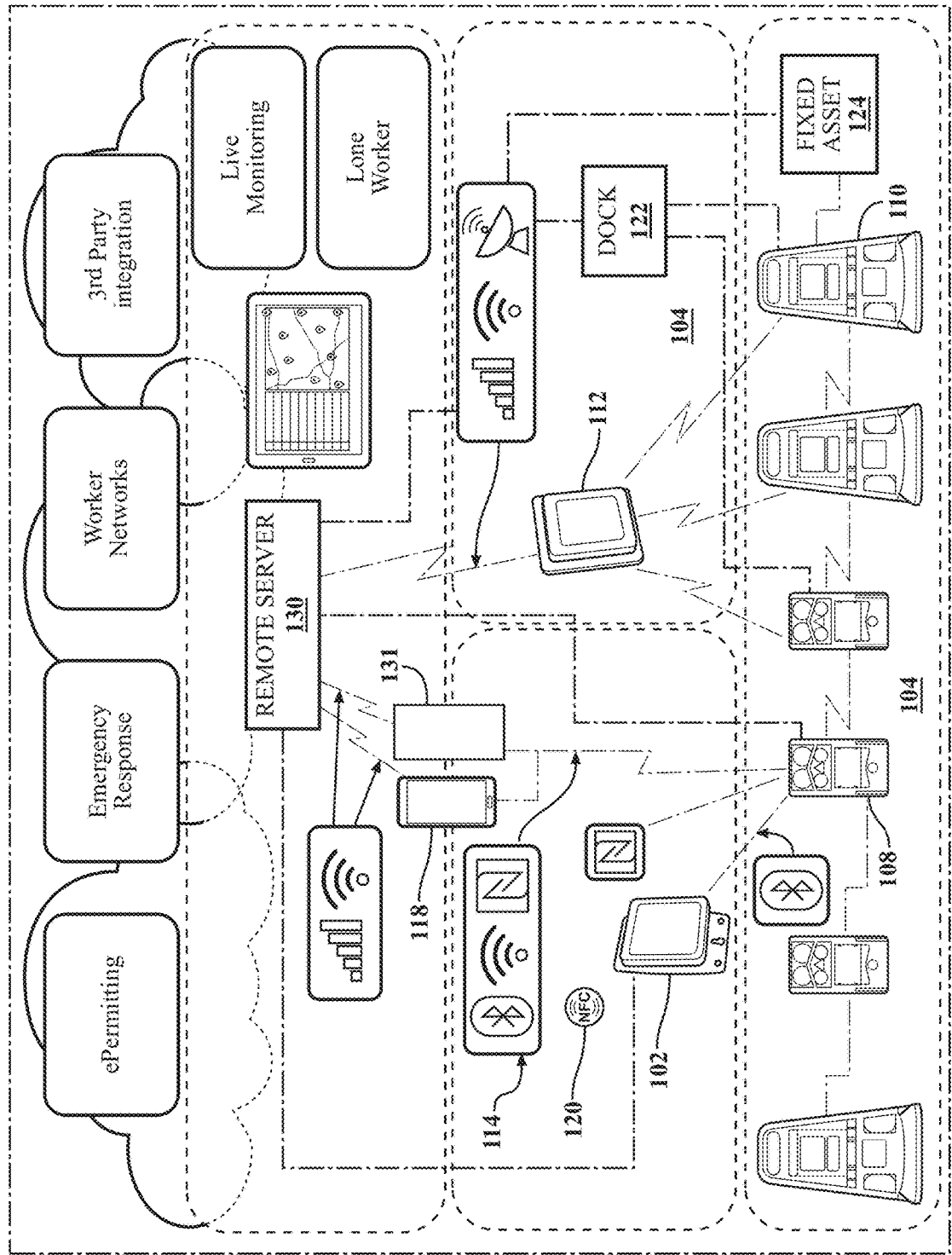
FIG. 1 depicts an overview of the worker safety system.

Referring to FIG. 1, in order to provide various services and monitoring in a real-time or near-real time fashion with respect to portable environmental sensing devices, hazard detection devices, and other safety instruments and devices, instruments and devices is such a system need reliable methods communicate with each other and/or with a remote location, all while in a challenging environment. This disclosure describes various aspects of a worker safety system, general components of which are shown in FIG. 1. The disclosure describes various communications strategies and technologies to enable various applications and services related to worker safety. In addition to showing the general components of such a system, FIG. 1 and the accompanying description provide an overview of the communication approaches and strategies, certain useful accessories, and various applications enabled by the worker safety system.

FIG. 1 illustrates certain portable environmental sensing devices 108 and area monitors 110, but it should be noted that other safety devices may be used with the system such as, multi-gas detection instruments, a gas detection instruments, a portable electrochemical gas sensing apparatuses, respirators, a harness, lighting devices, fall arrest devices, thermal detectors, flame detectors, or a chemical, biological, radiological, nuclear, and explosives (CBRNE) detector. In embodiments, environmental sensing device may be as described in "VENTIS PRO" U.S. Pat. Nos. 9,000,910, 9,575,043, 6,338,266, 6,435,003, 6,888,467, and 6,742,382, which are incorporated by reference herein in their entirety. In embodiments, area monitors such as described herein as well as in U.S. Patent Application Publication No. 2016/0209386, entitled MODULAR GAS MONITORING SYSTEM and filed on Jan. 15, 2016, the disclosure of which is incorporated herein by reference in its entirety. Throughout this disclosure, the terms environmental sensing devices (or instruments) 108, area monitors 110, and it should be understood that any of methods, systems, applications, interfaces, and the like described herein may be used by any of the environmental sensing devices (or instruments) 108, and area monitors 110. In addition, the disclosure may refer to environmental sensing devices and area monitors collectively as "instruments". In embodiments, the environmental sensing devices 108 and area monitors 110 may communicate with one another using a mobile ad hoc wireless network (MANET) 104. As used herein, the term MANET is a continuously self-configuring, infrastructure-less network of mobile devices connected wirelessly. One such MANET that may be implemented is a mesh network. As used herein a mesh network is a network topology in which each node relays data for the network and all mesh nodes cooperate in the distribution of data in the network. Embodiments of the mesh network between environmental sensing devices 108 and area monitors 110 will be described further herein. In embodiments, the mesh network can enable communication between components of the system without the need of other conventional communications technology for wireless communication, such as WiFi, satellite, or cellular technologies. Because the mesh wireless network overcomes the challenge of operating a computer network where devices communication solely with a centralized device, such as a hub, switch or router, the network better operates in challenging environments where obstructions or distance prevent wireless communication from a device to a hub. By utilizing the mesh network, devices can communicate with one another to transmit messages from devices to other devices to communicate with one another or to pass information among devices or to eventually transmit the message to a device on the perimeter of the network for forwarding to another network, such as a device in the cloud. Industrial environments also typically represent challenging environments because sensors may be constantly moving or regularly changing location, the environment can be large or remote from public wireless infrastructure, large obstruction such as metal tanks may block signals, and the environment may be underground. This disclosure may also include devices, nodes, and the like communicating on a peer-to-peer network (P2P), which may be part of a mesh network.

It should be understood that the embodiments described herein may operate on a mesh network, P2P network, or similar type of network. FIG. 1 also depicts various approaches to ultimately communicate data from the instruments to the cloud or remote server, such as via an API 114, smart device 118 or other mobile gateway 131, a gateway 112, and a dock 122.

In embodiments, the mesh network 104 of this disclosure delivers "ready to use" wireless functionality to instrument platforms. When equipped with hardware to be compatible with the mesh network 104 and embedded firmware, instruments are able to communicate wirelessly with one another. Mesh wireless networking provides instrument features such as peer alarms, or "shadowing" readings from one instrument on another instrument's screen—all within challenging environments typical to industrial safety. The mesh networking feature set is available for area monitors and portable instruments and enables interoperability, allowing a mixed network of portable and area monitor instruments to share readings and alarms.

Instruments 108 also communicate, via the mesh network with other mesh network-enabled infrastructure devices that further enable live monitoring, automated messaging, and location awareness, such other mesh network-enabled infrastructure devices including network gateway device (also referred to herein as "gateway") 112 and docks 122. For example, a network gateway device 112 may be placed in location in proximity to instruments, devices, computers, vehicles, equipment, and the like to enable communication with a network infrastructure. The instruments may communicate with the network gateway device 112 through the mesh network 104, and in embodiments, the data may be ultimately communicated, to a cloud server, via networking technology, such as WiFi, cellular, satellite, and the like, for downstream uses, for example by a remote server as described herein. There may be two-way communication through the gateway 112 such that remote servers or applications running in the cloud may be used to control, configure or otherwise communicate with the instruments 108, 110 through the gateway 112.

In embodiments, the dock 122, or docking station, may be used with the instrument to provide predictive diagnostic information, as described in U.S. Pat. No. 6,442,639, entitled Docking Station for Environmental Monitoring Instruments, which is incorporated by reference in its entirety herein. The docking station or gateway 112 (or API 114/Smart Device 118/mobile gateway 131 as described herein) may be connected, typically via the Internet, to a remote server 130, and exposure data, calibration data and diagnostic data are communicated from the instrument to the docking station and from the docking station to the remote server 130. Mathematical analysis of the collected data from all available sources is performed by the remote server 130 to, among other things, generate predictive warnings to alert the users of potential instrument faults, thus allowing preemptive maintenance, incident management, and the like. The analysis methods include principle component analysis and other statistical methods, fuzzy logic and neural networks. In embodiments, the worker safety system can take data from components of the system, store such data, generate reports to be sorted based on the data and communicate the data to a user. Such data communicated to a user can include, for example, events, need for calibration/bump testing, maintenance record, alert that settings are incorrect or sub-optimal, and error codes. The remote server 130 may also generate alerts to send to users, can change settings remotely, can alert a user if another user has an alarm and provide information on where to respond, and other end use applications as described herein.

Figure 2:
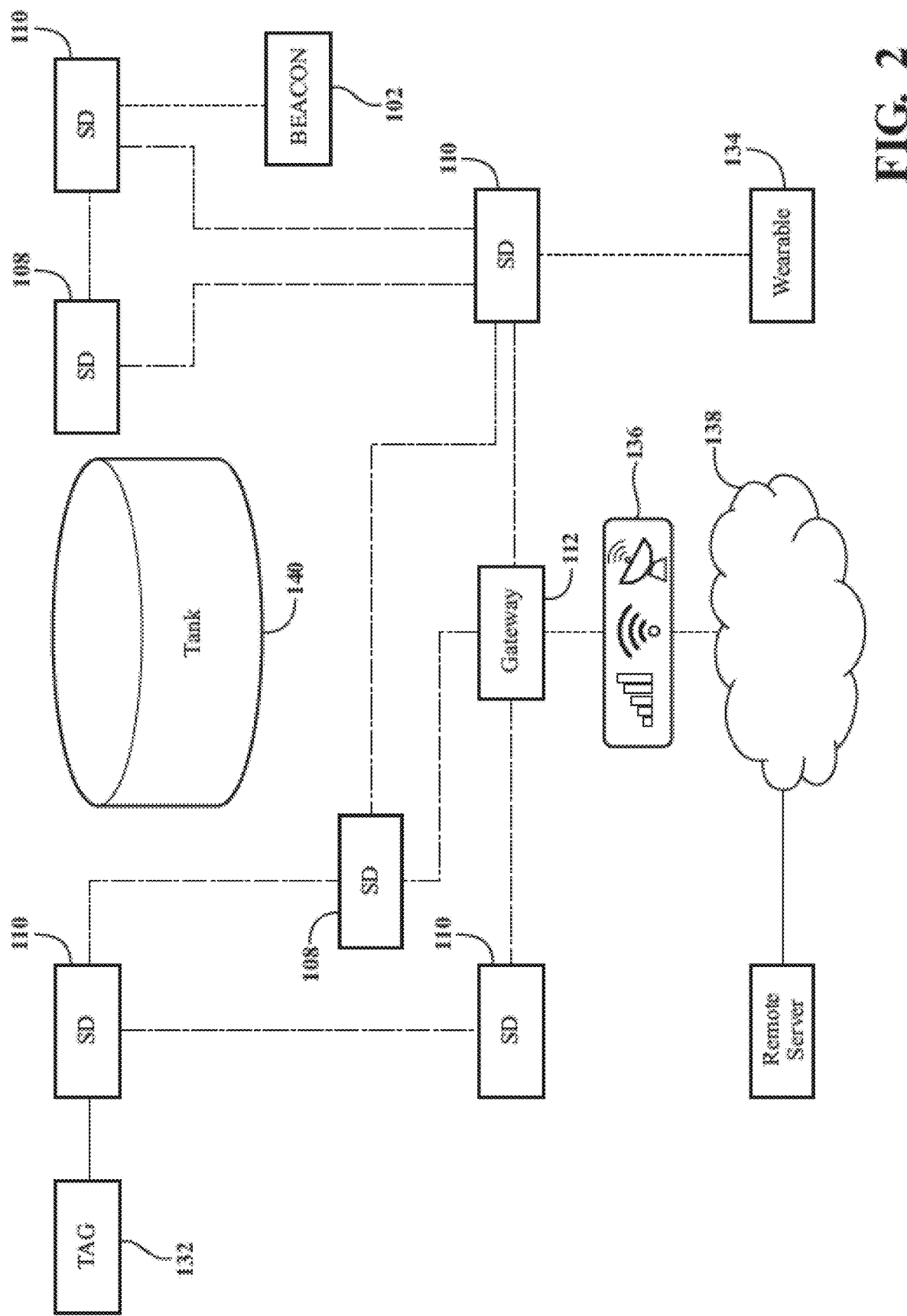
FIG. 2 depicts a challenging environment for networking.

The mesh network may be tailored to the unique needs of worker-to-worker communication. In an embodiment, the wireless network may be applied to the challenge of hazardous gas detection—relaying alarms and readings among a group of gas detection instruments in the challenging environments described herein. Referring to FIG. 2, a particular challenging environment is shown. Instruments 108 and 110 communicate with a beacon 102, a tag 132, a wearable 134 and to a gateway 112 through an external cellular, satellite, or WiFi network 136 to the cloud 138. A large metal tank 140 is present in the environment though which signals will not pass. FIG. 2 illustrates that instruments 108 and 110 either communicate with nearby instruments 108 and/or 110 and not with remote instruments or instruments blocked by obstructions, such as tank 200. Instruments 108 and 110 interoperate to create paths for data between instruments 108 and 110 which are not directly connected.

True mesh communications allowing sensors to communicate directly with one another is novel in portable gas detection. Daisy-chain alarms, such as perimeter or fence line, for area monitoring exist, but current wireless implementations for portable devices 108 only relay information to a central display or "controller", such as a laptop computer or a dedicated display device.

This disclosure describes the features of the wireless network, and how these features work in concert to address the challenges of worker-to-worker communications. These challenges include ease of use, difficult environment, dynamic network topologies, and power consumption.

The mesh wireless network 104 may relay an alarm notification from one instrument to another instrument. "Peers" could be, for example, two portable instruments worn by two members of a crew, three area monitors surrounding a work zone, or some combination thereof. Peers are equals in the network and information may be exchanged in both directions.

Points in a network are called nodes. Nodes in the mesh wireless network 104 may include instruments 108, 110, devices 118, beacons 102 (which are described further herein), gateways 131, 112, docks 122, and the like. Most wireless networks have a coordinator node, a single entity in the network to coordinate the activities of others. In star network topologies such as WiFi, the coordinator node is the access point. In Bluetooth, the coordinator node is the master (smartphone or PC). In other mesh protocols like Zigbee and WirelessHART, a dedicated coordinator node is used. ZigBee is a registered trademark of Philips Electronics North American Corporation. WirelessHART is a registered trademark of Hart Communication Foundation. In all of these cases, the coordinator role is necessary for the network to operate and is a dedicated device for performing the coordinator function. The coordinator manages routing tables, sets Time Division Multiple Access (TDMA) slots, coordinates frequency hopping, etc. The coordinator may be line-powered for reliability and availability for communication. For example, in WirelessHART, the role of the coordinator is vital, a backup coordinator is held in reserve, just in case the primary coordinator fails.

A coordinator node is not required with the mesh wireless network 104 of the present invention, as it is a truly ad-hoc network. Any collection of two or more instruments may form a network, without the need for any infrastructure. The mesh network 104 can tolerate the loss of any member, at any time, without warning because each device communicates with all other devices within range and maintains a database of devices from whom communications have been received. When messages from a device have not been received within a predetermined period of time, the device is removed from the database.

For security, every node has a default private encryption key which may be changed. By changing the encryption key, a network can be kept secure but also can be altered to keep mesh networks intended to operate separately in the same space from communicating with one another, such as keeping the network of different contractors in an industrial environment from contacting one another. The network is blind to nodes operating on a different encryption key. Also for security, dynamic frequency hopping, as described below, is implemented so that the channel on which the network will be communicating is pseudo-random and constantly changes. Finally, security may be implemented by bringing a node into contact or near-contact with a near field communication device ("NFC") to identify and authorize that node on the network, as described below.

High bandwidth, low latency MANETs, like those used on the battlefield, are extremely sophisticated. They involve multi-radio units and significant communications processing hardware, but wireless environmental sensing such as gas detection may not require this level of performance. The mesh network 104 excels at sharing a small amount of information, with a plurality of other instruments, with relatively low (such as a few seconds) delay without the complexity of existing high-bandwidth, low latency MANETs. One feature eliminating the complexity of other MANETs is that the mesh network 104 assumes messages reach their destination In embodiments, the mesh network 104 emphasizes energy efficiency using power-efficient broadcasts of information. The network 104 operates on a constant network interval, for example 1 second. Within the network interval is a period of broadcasting and a period of sleep cycling. Moreover, the length of the period of broadcasting is altered in the mesh network 104 based upon the number of devices currently joined to the network, such that a network with few devices can be even more power efficient by increasing the period of sleep cycling within each network interval, as further described below.

In embodiments, the mesh network 104 may not be a long-range link. The mesh network 104 may typically operate at distances of 100-200 m between individual nodes, and is not intended for remote monitoring of a distant site. The mesh network 104 feature set is meant to communicate between, and alert workers within, the same group and working in the same vicinity. It provides acceptable range and coverage by leveraging the mesh topology.

The mesh network 104 shares information and alarms with other instruments without a dedicated coordinator node, or any fixed nodes for that matter.

In embodiments, the mesh network 104 provides a setting-free, self-forming, self-healing, resilient wireless network without a dedicated coordinator node. As described below, there are no user settings required, no channel selection, and no PAN id to enter. In one embodiment, with the intuitive action of touching two instruments together, a network may be formed. Touching another instrument to an existing member of a network joins the new instrument into the network if the instrument is not already in a network itself. Touching the instruments may be a tap, double tap, bump, both being shaken together, a touch of the tops of the instruments, a touch of the bottoms of the instruments, and the like. In embodiments, if when the instruments are tapped it is determined that they are each already members of a different network, each instrument may be prompted to leave their network, and if one leaves, upon re-tapping, the network joining may be successful. In a distributed fashion, the network is maintained and adapts as member instruments come and go and move about the challenging RF environment typical of industrial settings.

The wireless network's adaptability and resilience is a result of an emphasis on wireless diversity. This diversity takes three forms: space diversity, frequency diversity, and time diversity. Space diversity involves transmitting a wireless signal over several different propagation paths, with the understanding that different paths experience radically different RF impediments. Space diversity is the reason most WiFi access points have more than one antenna—even separating two antennas by a few inches significantly reduces "dead spots" in coverage caused by reflections off walls and other objects. Instruments operating on the mesh network 104 are too small to benefit from multiple antennas; however a mesh network such as 104, where messages can take alternate paths through a network provides the same effect, even with as few as three nodes—as illustrated by the example above.

Frequency diversity, also known as frequency hopping, is a scheme where a communication system regularly changes the frequency (channel) used for communications. Frequency diversity helps overcome some sources of dead zones because areas of destructive interference due to RF reflections (called multi-path fading or multi-path interference) occur at different locations at different frequencies. Frequency diversity also helps avoid interference with other users of the wireless spectrum. If a nearby device is using only a portion of the spectrum, only some transmissions are impacted. In embodiments, the mesh network 104 may implement a slow-hopping scheme. Each network interval (for example, about once per second), the network may switch frequencies, preferably using a pseudorandom sequence. This is in comparison to a "fast-hopping" system like Bluetooth, which changes frequencies 1,600 times per second. Fast-hopping is appropriate when an interruption of just milliseconds would matter—like streaming audio from a phone to a stereo. Slow hopping requires less computational horsepower (saving power) and simplifies the process of locating and joining networks.

Time diversity involves transmitting the same information at different instances of time. The chances of a message getting blocked multiple times is far lower than if the message is sent just once. In the mesh network 104, time diversity may be achieved by at least two means. First, instruments on the mesh network 104 may transmit their information quite often—at least once every few seconds. Second, each regular transmission from an instrument on the mesh network 104 may be a complete (yet compact) snapshot of the instrument's current condition (called state-based communications). For example, an instrument on the network 104 may be a gas sensor which transmits its current state to the network, including information identifying it as a gas sensor, a gas reading, an alarm status, whether a panic between has been pressed, instrument status, etc. In embodiments, nothing important is sent just once (event-based communication), for example in a gas sensor the snapshot of the devices current condition may be sent every network cycle, for example. If one transmission is lost, for example due to a collision with another instrument's transmission, the next message is likely to make it through. Time diversity is particularly effective when combined with frequency diversity, as the next transmission will use a different part of the RF spectrum that has different RF impediments.

In embodiments utilizing mesh networking, which is a collection of wireless nodes that communicate with each other either directly or through one or more intermediate nodes, the nodes may operate in harmony, cooperatively passing information from point A to point B by making forwarding (routing) decisions based on their knowledge of the network. Through this collaboration, a mesh network can extend over long distances and operate in spite of very poor RF "line of sight" conditions between some of the nodes of the network.

Through the process called binding, which relates to the process of placing two or more nodes into the same network, the wireless network 104 may automatically correct settings mismatches between instruments, such as the timing of the network interval and the frequency hopping sequence. In this way, any errors made in network setting that a user, for example entered by an industrial hygienist, or administrator can be corrected automatically when two instruments bind.

The wireless network may implement a radio incorporating mesh networking technology. The radio uses relatively common IEEE 802.15.4 radios similar to those used in ZigBee. The radio adds a network operating system layer that implements a self-forming mesh routing layer. Networking functions are distributed with the network, it requires no central coordinator node for operation. All nodes can forward packets, creating and updating their own routing tables.

In embodiments, the end application, such as a gas detection instrument 110 or 108, interacts with the networking layer using a novel approach. The radio module implements a virtual machine, with access to nearly all radio module and networking functions. The behavior of the radio and network can be tailored and highly optimized by the application layer to operate the mesh network 104 of the present invention to the specific needs of the application using custom scripts. The wireless network behaviors can be highly tailored to the unique needs of gas detection.

In embodiments, the wireless network may be implemented in scripting ("radio scripts", or "script" herein). Wireless network scripts run within the network operating system (also referred to as "radio firmware" or "firmware").

The network operating system platform also includes a hardware abstraction layer (HAL) that insulates the application from radio hardware specifics. This allows the same script to run on different supported radio hardware without modification.

The radio modules use radios compliant with IEEE 802.15.4. These radios can be operated at different frequencies. The wireless network uses the 2.4 GHz band due to its nearly universal world-wide acceptance (without the need for end-user licenses) and improved performance in industrial environments with lots of metal obstructions. In embodiments, there may be 16 available channels, each 2 MHz wide, in a 2.4 GHz 802.15.4 system.

Figure 4:
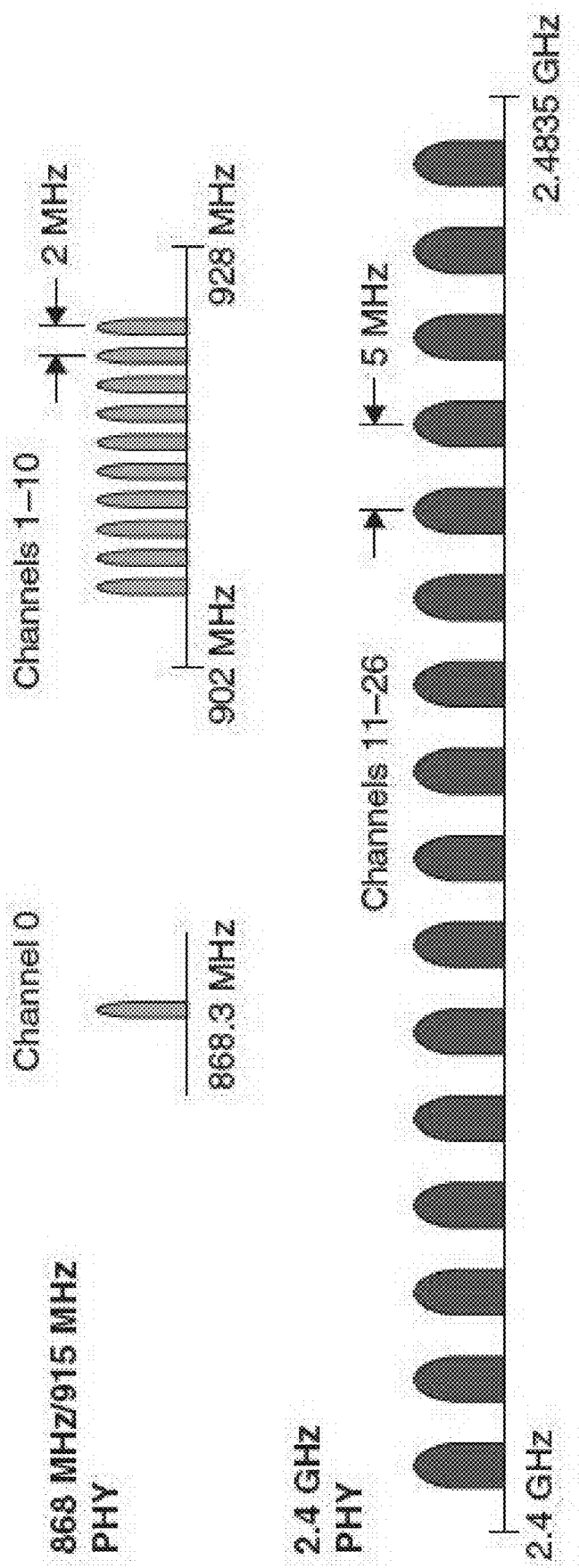
FIG. 4 depicts frequency channel overlap.

Referring to FIG. 4, the channels may overlap with the same spectrum used by Wi-Fi, Bluetooth, and other consumer and industrial systems, so the wireless network may be designed to coexist with other wireless systems through the diversity schemes introduced herein, particularly frequency diversity.

With respect to power conservation, sleep cycling is a process where the entire mesh network communicates with one another during a regular, but small window of time. It is important to understand that the entire network wakes and sleeps at the same time. The advantage of sleep cycling is reduced power consumption. By allowing nodes to sleep while they are off the air, the average current consumption is reduced. The ratio of communication time to sleep time may be directly proportional to average current consumption. If radios only spend 10% of their time in the communication period, their average current consumption will be roughly 10% of their on-state current (sleep current is negligible). The advantage of sleep cycling in a mesh network is its simplicity—when it is time to talk, the mesh network behaves as if it were always on. There is no need to plan time slots for each pair of nodes or understand the physical topology of the network, which would be easier to do with a dedicated coordinator. The challenge in sleep cycled networks is keeping everyone on the same schedule, but can be overcome with synchronization techniques as described herein.

Both the instrument itself (for example, a gas detector) and the wireless network radio may employ sleep cycling. Most instruments wake once a second (or two seconds in some cases) to measure an environmental parameter, such as gas, and perform housekeeping functions before going back to sleep to reduce average power consumption. As discussed herein, the wireless network sleeps too, under the direction of the network leader. In embodiments, these two sleep cycles cannot be synchronized. Different instruments have different wake/sleep schedules, and the rates at which gas concentrations are measured are subject to considerable regulation. A system where gas measurement rates are not deterministic would be difficult to certify. Communicating between these two sleeping systems is difficult.

To address the challenge of the radio and the instrument operating on different wake and sleep cycles, nodes of the mesh network 104 may employ a shared memory interface between the radio and instrument. Described functionally, the shared memory interface may be analogous to a mailbox. Anyone can stop at the mailbox and insert items for someone else, while at the same time checking to see if any in-bound mail has arrived. A second person can do the same. The two people don't need to be at the mailbox at the same time to exchange information. If there is something urgent in the mailbox for the other person, the indicator flag may be raised to ensure they pick it up at the next opportunity. If two people arrive at the same time and try to check/deliver mail simultaneously, they could end up dropping some mail on the ground in the confusion. The shared memory interface uses "Request" and "Grant" lines, one each for the radio and instrument to ensure two people don't reach into "the mailbox" at the same time. The arbiter is a special circuit that prevents two "Grants" from being active at any moment in time. The shared memory also implements an "Urgent" line that is the equivalent of the indicator flag on the mailbox.

Figure 5:
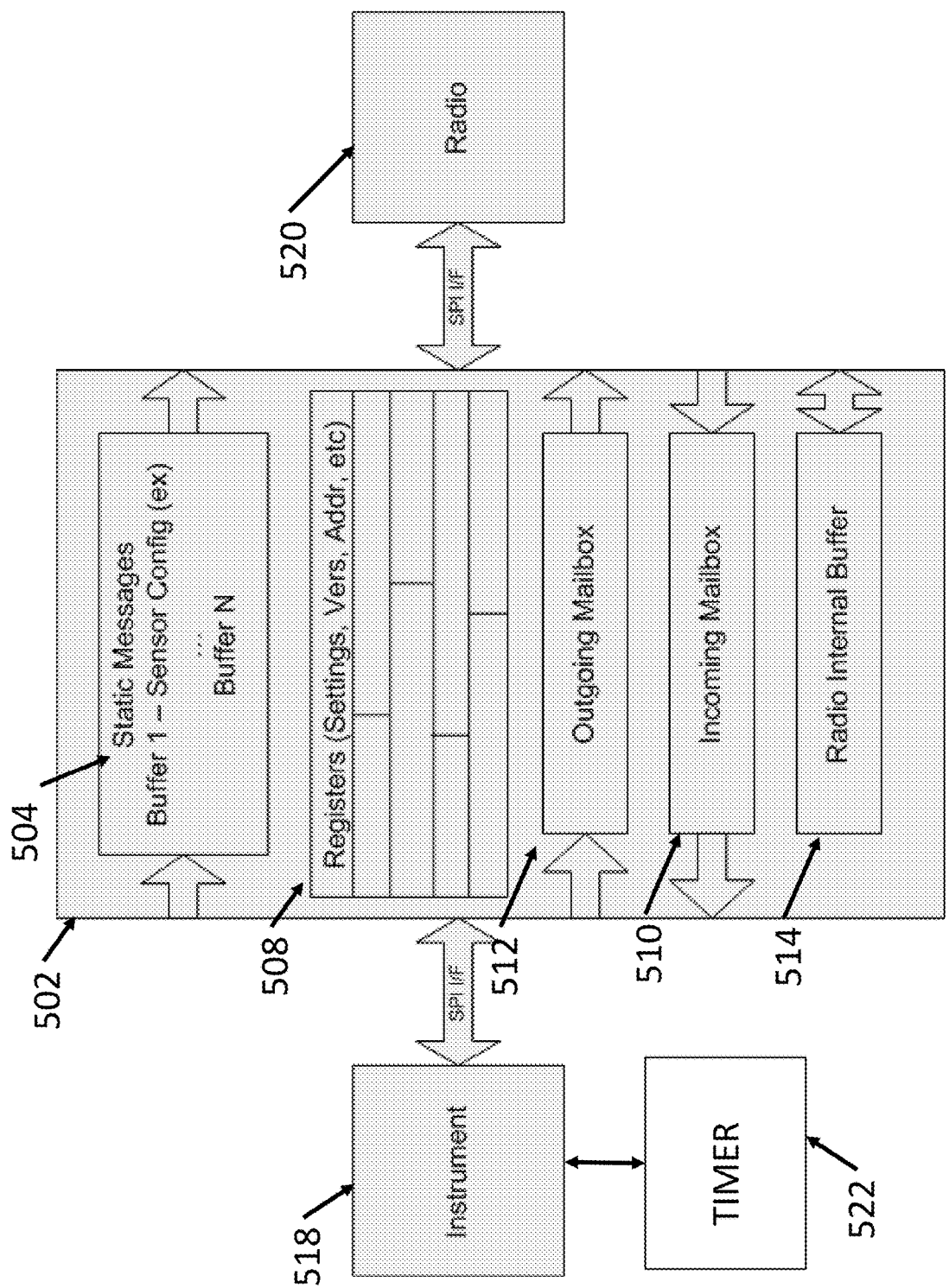
FIG. 5 depicts a shared memory interface.

Referring to FIG. 5, the shared memory is described structurally. The shared memory is a simple 32 kB static RAM chip 502. Within this memory space, the wireless network implements different storage locations for different types of information. Commonly sent messages have dedicated memory locations (Static Messages 504). An example of a static message would be a message indicating the type of instrument attached to the node. The radio's 520 configuration and status may be communicated using a bank of registers 508. Incoming 510 and outgoing 512 mailboxes handle all messaging not covered by a Static Message type. Finally, some memory is allocated to the radio module, a radio internal buffer 514, for its internal use, because the memory structure available within the network OS may be limited.

Furthermore, every node (for example, portable environmental sensing devices 108 and area monitors 110 in the mesh network 104) include a precision timer integrated circuit 522, as described below.

In embodiments, the host instrument 518 may control nearly everything about the wireless network radio. Configuration messages may be provided to modify the vast majority of the radio settings. In a couple of cases, the instrument 518 may modify settings through registers as well. The instrument 518 may also control the state of the wireless network radio 520 and can place the radio 520 into Sleep or Off Air modes at will.

In embodiments, instruments compatible with the mesh network 104 may send a surprisingly small variety of messages. The most common message is instUpdt( ). The payload of this message is a snapshot of the instrument status.

In order to minimize network traffic, the wireless network may implement two different flavors of instUpdt( ) message. If all is normal with the instrument, and all sensor readings are near "zero", a short ("terse") version of the instUpdt( ) message is sent. The terse version essentially says "I'm Ok". If the instrument is detecting gas or experiencing any alarm, the more detailed "verbose" format is sent, which includes all sensor readings and alarm details.

In embodiments, a verbose message with 6 sensors may be around 40 bytes. The terse form of the message may only be 10 bytes long. An instrument may send status messages in the terse format unless: another instrument requests it to go verbose (for example if it wants to display real-time gas readings for a confined space entry), a gas reading is above the wireless deadband (currently set at 25% of the low alarm level), or the instrument is in alarm for any reason (including panic and man-down).

When one instrument wants to see all information from another instrument (for example, when an attendant wants to display real time readings from a confined space entrant), even near-zero readings, it can request the instrument send the verbose format by issuing the setVerbose( ) message. For example, an instrument may be requested to go into a verbose mode when the instrument is being shadowed, such as when the instrument wearer enters a confined space. The payload of this message may include the number of seconds for which the sender is requesting verbose messages be sent.

A set of messages termed "identify" may provide the relatively static information needed to correctly interpret the payload of the instUpdt( ) message. These messages may contain configuration details about the instrument, including numbers and types of sensors, instrument type, serial number, current user and current site. When an instrument first joins a network, it may broadcast this information for other instruments already in the network to save. Instruments that join later, or for any reason need to fill in their details about another instrument can request an instrument resend this data (broadcast or unicast) using the idReq( ) message.

Using the information found in instUpdt( ) and the identify messages, a relatively complete picture may be generated to reflect the current status of any instrument in the network.

Referring to FIG. 6A, as instUpdt( ) messages arrive, receiving instruments are expected to extract the relevant information, correlate it to the correct instrument, and update their internal peer status list accordingly. When a message arrives from a new instrument, as indicated by a new media access control ("MAC") address, the instrument is added to the peer list and missing information is filled in from the identify messages. A MAC address is a unique identifier assigned to network interfaces for communications at the data link layer of a network segment that uniquely identifies the device on the network. When an instrument leaves the network (e.g., user selects "disconnect", or powers down the instrument), it sends a special "disconnecting" message, which may be send repeatedly, and should be removed from the peer list of other nodes on the network. Instruments expect to hear an instUpdt( ) message from each peer in each network cycle. If these messages stop after the expiration of a predetermined number of network cycles, the peer instrument may be marked "lost" and a warning may be sounded (if enabled).

Referring to FIG. 6B, shadow gas is a term used to describe the instrument feature where one instrument can display the real-time readings of another instrument remotely, which may be particularly helpful for confined space use cases. Shadow gas feature is activated by selecting a peer instrument from the List of Instruments, as shown in FIG. 6A. A screen representing the remote instrument may be displayed and update in near real-time. In this case, even near zero gas readings may need to be displayed, to provide confidence to the user that the readings are indeed being relayed to the observer. In addition to the shadow gas readings, the other instrument's location may be displayed, such as on a map.

To enable this functionality, some combination of the identify messages and setVerbose( ) are used. When a remote instrument is selected, the instrument will gather information such as the username, sensor details, and the like to populate the Shadow Gas display. The remote instrument will be set to transmit verbose readings.

One of the ways to improve robustness of a wireless network is to enlist the help of the end user such as by displaying a relevant signal quality indicator on the user's screen, analogous to the "4 bars" displayed on most cellular phones. The signal quality indicator helps users diagnose connection issues themselves, reducing support calls. It also warns users of an impending loss of communication, so they can address it. Preferably, the signal quality indicator displays an indicator of the quality of connections of all of the nodes on the network. Alternatively, the signal quality indicator displays the quality of the connection between the instrument and a predefined node on the network. Alternatively, the signal quality indicator displays the quality of a connection between the instrument and the strongest direct connection with another node.

For the mesh network 104, the signal quality indicator may be derived from a combination of the received signal strength (RSS) and packet receive ratio (PRR, or "Health Counter") of all the instruments in a given network. This is unlike a cellular phone, which displays only the signal quality between a phone and the nearest tower.

The RSS is available from the MAC layer of the radio for each received packet. The instrument records the RSS from the last message received from each peer instrument. The signal strengths represent the last network hop taken by the message and do not necessarily reflect the weakest link in the path taken. The PRR or health counter is a measure of the recent number of received messages versus the number of expected messages (based on the network interval). The PRR or health counter is tracked for each peer. The PRR or health counter is a counter that begins at a predetermined number, such as 10, and is incremented and decremented when expected packets are received or not received, respectively. The increment and decrement values may not be the same, such as incrementing by 3 and decrementing by 2.

When the health counter reaches zero, the node presumes that it is lost from the network.

The signal quality indicator is based on the product of RSS*PRR for each node, summed and divided by the number of instruments in the network. Alerts may be set for one or more remote nodes to monitor signal strength, and a warning may occur when the strength drops below a threshold and an alarm may issue when signal drops out. A critical alert may be set when the signal being monitored is a safety monitoring point.

The wireless network feature set may be implemented in several parts and layers of an instrument, including the instrument firmware, radio scripts, and radio firmware. As features evolve, each part of the system may need to be updated. A robust system may be needed to allow for field updates while ensuring all the pieces remain compatible.

Figure 7:
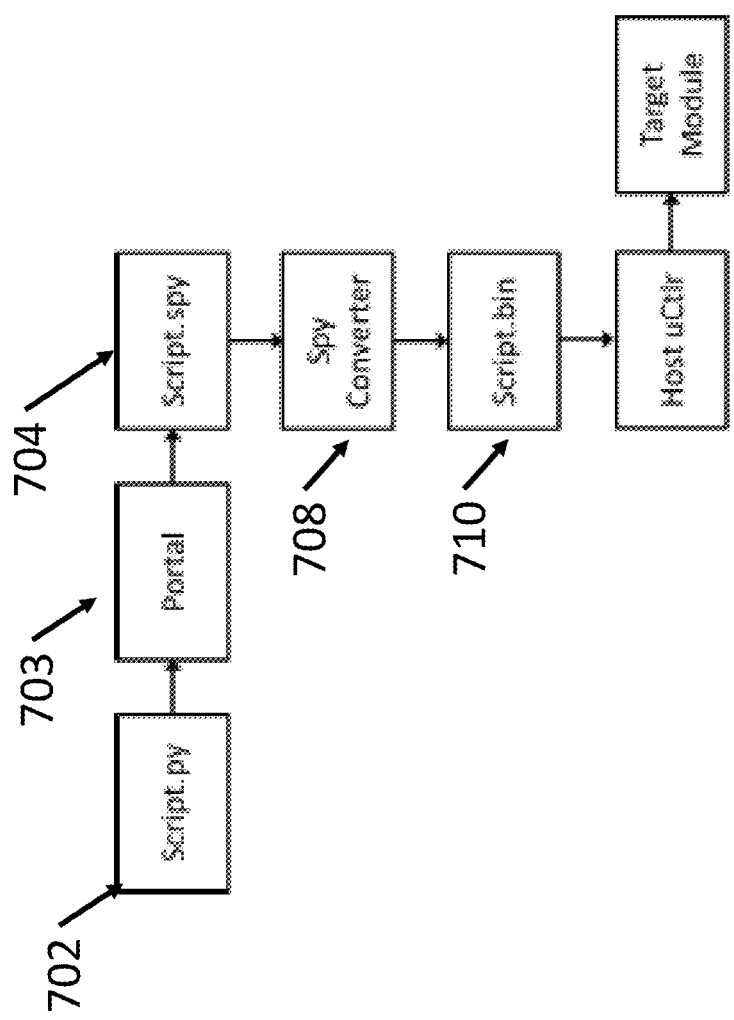
FIG. 7 depicts a script process for the wireless network.

Referring to FIG. 7, wireless network scripts may be written in a scripting language developed using the portal IDE 703. The script 702 (Script.py) can then be "compiled" to bytecode for a specific radio module (or "platform") into a .spy file 704 (e.g., SM200 radio module and an SM220 radio module have different .spy files). The Portal IDE also provides a checksum for the compiled script (used later). A converter application 708, such as the Windows-based PC application SpyConverter may be used to convert the .spy file type 704 into a .bin file 710. The .bin file 710 is converted to a .hex file using the programming utility (e.g., JFLASH) and merged with other parts of the instrument firmware. The script's checksum (from the Portal IDE), Radio Hardware Version (e.g., SM200=0x01 . . . ), and the script version (3 bytes—Major.Minor.Build) may be appended to the script file, again using the programming utility, for use by the instrument in checking the radio's programming. The checksum and version (including hardware and script) should match what is reported by the radio module, or an error may be generated. The complete .hex file may be loaded into instrument memory by the instrument bootloader, like any other part of instrument firmware. Accessory Software, iNet, servers, worker safety system, and the docking stations have no knowledge that the instrument firmware image actually also contains firmware for the radio.

At power up, the instrument may check the radio module's script version, which may be displayed on the startup screen and available through Modbus. When the instrument detects an out of date script, it may begin the script update process. This process uses a special communications port between the radio and instrument. The instrument uses an embedded Script Uploader utility (similar to a bootloader) to transfer the file (in blocks) from instrument memory to radio memory. When complete, the new script is checked for validity before the radio module is rebooted and normal operation commences.

Once the wireless network script is running, the instrument may also check the radio module's firmware version that comes preloaded on the radio module. It is displayed on the startup screen, and available through Modbus. The instrument checks to see that the radio module firmware version is same or newer than the revision the instrument firmware and script are expecting (this value is hard coded in instrument firmware). This approach is based on the understanding that, in embodiments, features may be added, but not removed, from the radio network operating system. If the radio module version is out of date (not supported), the instrument may disable wireless network functionality (instrument continues to operate) and instruct the user to get the radio module firmware updated.

Once the wireless network script is running, the Radio module type (or Platform, e.g., SM200, etc.) may be read by the Radio module, translated into a single-byte value (e.g., SM200=0x01 . . . ) and posted to the host interface as the Radio Hardware Version. The instrument may post this value to modbus. At power up, the instrument may compare the Radio Hardware Version to the value appended to the programmer hex file. This may allow the instrument to confirm any future instrument firmware or radio script updates are compatible with the radio hardware installed.

Instruments compatible with the mesh network include any described herein as well as a barometer, which may be operable in an indoor location. The readings may be available using the host interface. The barometer reading may be saved to a Modbus register to enable factory testing. Using the barometer the altitude of the instrument can be detected. This feature can be used, for example, to determine the floor level of the instrument, such as in an underground facility. A compensation barometer, implemented as an instrument on the network located at, for example, ground level can be used to determine atmospheric pressure at the reference level. Using the detected atmospheric pressure and the reference atmospheric pressure, the floor level of the instrument can be determined. This information may be relayed through the network, and possibly through a gateway and to an external network, where the location of instruments can be displayed on a computer to show the location of instruments in latitude, longitude and elevation.

While the wireless network is operating normally, it is sleep-cycling, frequency-hopping, and encrypted. In this mode, it may be difficult to perform certain activities like testing the radio in manufacturing or performing an over the air update of radio module firmware. For this reason, a Test Mode may be implemented. In test mode, the radio stops sleeping and frequency hopping, and switches the encryption key to one that can be shared with service centers, manufacturing applications, etc. In test mode, the radio may respond to several external wireless commands that allow factory testing of the radio and over-the-air updates to radio firmware. Test mode may be accessible, in embodiments, by writing a special password to the test mode Modbus register (using software like DUSS, or a manufacturing application).

In embodiments, every node (for example, portable environmental sensing devices 108 and area monitors 110) in the mesh network 104 may include a precision timer integrated circuit 522. This timer 522 should be a stable timer, for example, stable to within a few milliseconds over an hour or more.

In most networks, synchronization is handled by a dedicated coordinator node. In the mesh network 104, this job is performed by one of the members of the network, called the leader. The most important job of the leader is to synchronize the mesh. The leader regularly broadcasts a wireless synchronization message to members of the network that marks the beginning of the period that the network is able to actively communicate, otherwise known as a "sync message" or sync( ) message. Follower nodes maintain synchronization with the leader's instructions. The leader node becomes the "master timekeeper" and all other nodes adjust their internal timers' interval and phase to match the leader's timer.

These synchronization messages issued by the leader may also contain a value that represents the number of nodes the leader believes are currently in the network. The leader bases this value on the number of instruments that are reporting messages, such as status messages or readings messages, such as gas status readings. The amount of time the network remains awake is preferably dependent on the size of the network to save power. Each node calculates its awake time, based on the value in the last synchronization message it received. For example, a network with only 3 instruments will spend much less time awake than a network with 20 instruments, saving power.

In embodiments, if a follower node doesn't receive a sync( ) message, it may still wake up at the prescribed time and exchange messages with other nodes. Because the hardware timers are so stable, even if several synchronization messages are missed or corrupt, the nodes continue to wake at the right time. Followers are not dependent on the leader for second-to-second transmissions, however, if synchronization messages stop altogether, a follower may eventually decide that it has lost the leader and will begin the process of rejoining the network, as described herein. Each time the network wakes, it uses the next channel in the frequency hopping sequence, as described herein with respect to frequency diversity.

In summary, by synchronizing the clocks of the mesh, the wireless network is capable of sleep cycling and frequency hopping, even without a dedicated coordinator.

Because the mesh network 104 is sleep-cycling and frequency hopping, it is only operating on a given channel about once every 14 seconds and there is little certainty regarding what set of channels a given wireless network is using. As a result, it may be difficult to join a new instrument into an existing network without considerable delay.

The mesh network 104 solves this problem by using advertising messages on the public channels. Members of a network allow others to join (or re-join) a network by "advertising" on pre-defined public channels. New (or lost) nodes can locate an existing network by listening on these channels. During every network cycle, the leader and all followers advertise the current network parameters on both public channels using a message, an example of which is called boPeep( ). The boPeep( ) message may include all information needed to synchronize with an existing network, including synchronization of timers, the number of devices on the network and the identity of the frequency hopping sequence. New members or members that have lost synchronization with the network may use these network parameters to join the network and re-synchronize with the leader. boPeep( ) messages (unlike most other wireless network messages) may be sent only with a single network hop. This is done to prevent flooding the network with retransmissions. Further, followers may only send boPeep( ) messages in network intervals when they have received a sync( ) message from their leader. Therefore, each follower helps identify only the current network leader.

Figure 8:
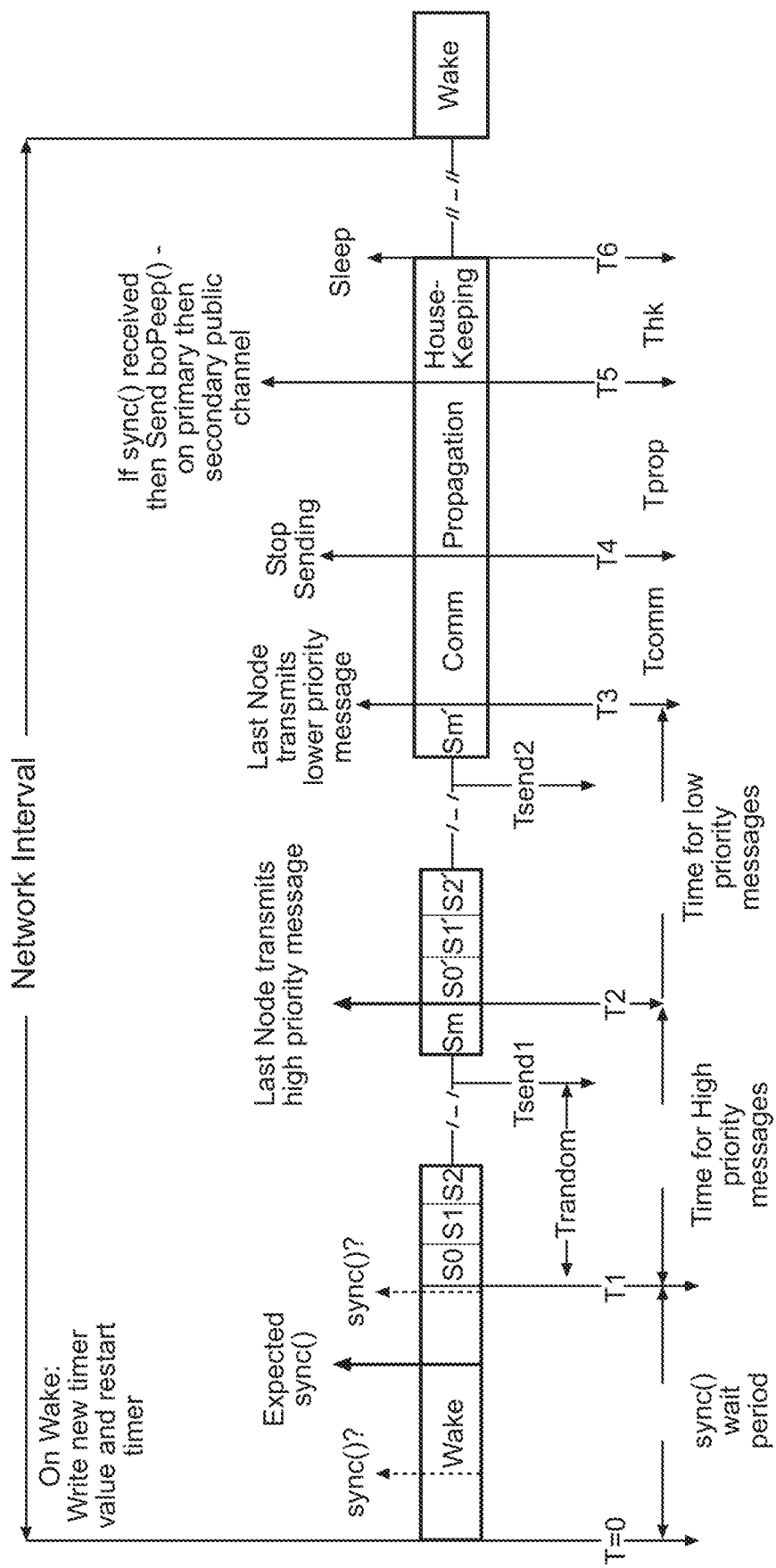
FIG. 8 depicts a synchronization scheme and FIG. 8A depicts a method for choosing a leader from members of a network.

Referring now to FIG. 8, most routine wireless messages are broadcast without collision avoidance or collision detection measures enabled, which is a byproduct of the mesh network's 104 synchronization scheme. During a first time interval (T0 to T1), followers listen for the leader to broadcast a sync( ) message. When the sync( ) is received, the followers calculate a time for the next expected network interval. If a sync( ) message is not received and has not been received for a predetermined number of network intervals, the node determines that it has lost the network and begins a network rejoin sequence, as described below.

In embodiments, to compensate for the negative aspects of lack of collision avoidance or detection, the awake time during the network interval is divided into sections (S0, S1, S2, . . . , Sm) during which nodes choose a turn to broadcast to help spread out the network traffic over the time the network is active (thus reducing the probability of collisions). Messages of the highest priority, such as instrument status messages, are sent first during period T1 to T2. All other messages are sent after each instrument has been given an opportunity to send its status message (T2 to T4). Transmissions will stop, and then a suitable time is left to allow all messages to propagate the network (T4 to T5). Finally, if a sync( ) message was heard in that network cycle, nodes go to each public channel and send a boPeep( ) message to advertise the network's parameters for lost nodes or new nodes wanting to join (T5 to T6). After T6, the node goes to sleep until the next network interval.

In embodiments, the number of slots (S0-Sm) may be proportional to the number of instruments in the network (n), and when number of slots is proportional to the number of instruments in the network, the leader broadcasts (n) in each sync( ) message. Each node calculates the network timing and selects a slot for broadcast at random. While this does not guarantee a dedicated slot, this mechanism may still be effective at spreading network traffic. Consider also that each node's clock may be slightly out of phase with the other nodes—the clock synchronization allows nodes to be as much as 10 mS out of phase with the leader. A typical wireless transmission may take less than 4 mS. Another key point is that each node's slot for broadcasting is randomly reselected on each network interval. Even if a node happens to transmit at the same time as another node, those two nodes are highly unlikely to select the same slots in the next network interval. Even with large networks, most messages get through and any one node is unlikely to be blocked for several back-to-back messages. Further, by increasing the number of slots available for transmission versus the number of devices in the network, the chance for collision is reduced.

Figure 8A:
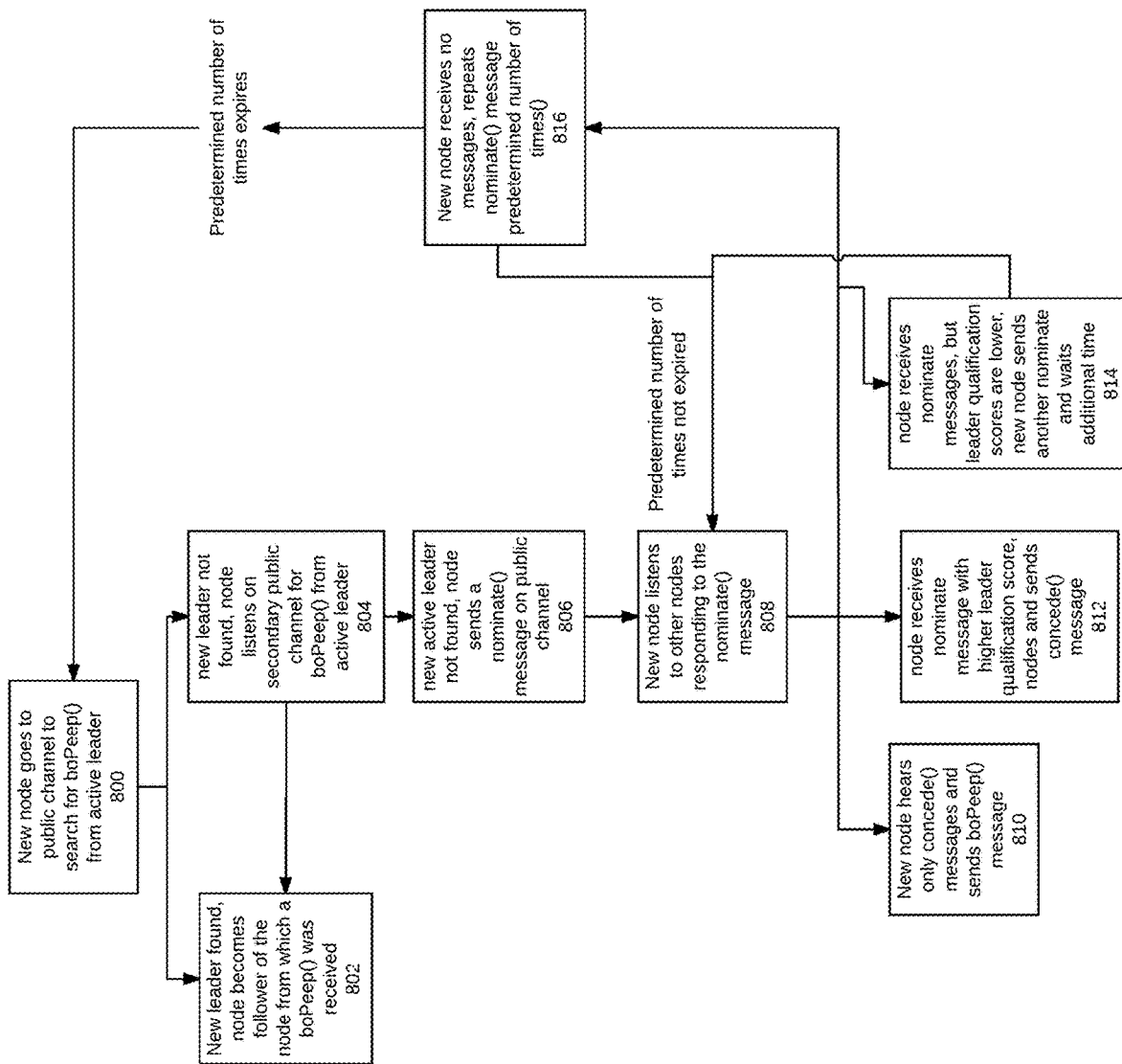

In embodiments and referring to FIG. 8A, the wireless network chooses a "leader" from the members of a network. Any node must be prepared to do the job of the leader. In the event that the current leader suddenly disappears, a different node performs the job of the leader. The process of picking a leader consists of nominations, elections, and ongoing monitoring.

In embodiments, in a first step 800, when a new node goes to the public channel to search for a network, it listens (such as for 4 seconds) for a boPeep( ) message on a first public channel, which indicates there is already an active leader. In a step 802, if a boPeep( ) is heard, the node assumes the role of a follower of the node from which the boPeep( ) was received. In a step 804, if no boPeep( ) is heard, the new node switches to the secondary public channel and listens again (such as for 4 more seconds). If a boPeep( ) is heard, the node assumes the role of a follower of the node from which a boPeep( ) was received in the step 804. If no boPeep( ) is heard on either public channel, the node returns to the primary public channel and begins the election process in a step 806.

In embodiments, in the step 806, the node sends a nominate( ) message, which may include a leader qualification score. The leader qualification score may be calculated based upon instrument type, battery state of charge, and past signal quality. Instrument type may be a relative measure of suitability as a leader—e.g., a fixed area monitor makes a better leader than a portable instrument. These parameters determine which radio will eventually be selected for the leader role. As further example, instrument types with large battery capacity make the best leaders because leaders consume more power than followers and a large battery leads to less leader interruption. Some instrument types may be larger and have greater range due to power and antenna size. Some instruments, for example fixed area monitors, make good leaders because they do not move, may have higher power and are typically located near the center of the mesh.

In embodiments, in a step 808, the nominating node may listen for a period of time on a public channel, such as for 1 second. Any other node listening may compare the nomination message and send a concede( ) or nominate( ) message depending on how the node's own leader qualification score compares to the nominating node's leader qualification score. Next, one of the following cases occurs: 1) in a step 810, if the nominating node hears concede( ) messages, but no nominate( ) messages, it declares itself leader by issuing a boPeep( ) or 2) if the nominating node hears any nominate( ) message, it compares the sender(s) leader qualification score to its own and in a step 812, if the sender's score is better, it sends a concede( ) message, or 3) in a step 814, if the sender's score is worse, it sends another nominate( ) message and waits an additional period of time, such as for 1 more second. If the qualification scores are the same, the lower MAC address is considered better. In a step 816, if the nominating node hears no messages after 1 second, it sends another nominate( ) message in step 806, which may be sent repeatedly, such as up to 4 more times if the nominating node hears no message. If, after 5 seconds or a predetermined number of nominate( ) messages, for example, the nominating node has heard no messages, it goes back to listen on the public channels in step 800 for an additional period of time, such as 8 more seconds, before repeating the election process.

After being selected as the leader of a network, the leader will begin to frequency hop by changing the broadcast channel in each successive network interval. By broadcasting the boPeep( ) in the public channel, it will allow the nodes that lost the election to join its network and follow its frequency hop sequence.

In embodiments, certain area monitors on the wireless network may continue this process indefinitely, so that whenever a second area monitor is powered on (and on the same channel), they will connect automatically. Certain portable gas detectors may be expected to stay in this searching mode only for a limited time (e.g., minutes), before the radio is powered off to save power.

In addition to synchronizing the network, the leader has a couple of other important jobs. One may be a process that prevents multiple leaders of a given network. This step is important in resolving cases where the leader becomes separated from the network, or one half of a network becomes separated from the other, such as when the leader moves away from multiple devices. In such a circumstance, the devices separated from the leader will nominate a new leader. However, if the two leaders come into proximity with devices that had previous followed a different leader, confusion can result from the existence of two network leaders with the same network ID. These cases can result in multiple leaders of the same network, which in turn can lead to erratic behavior. Therefore, it is necessary for leaders to occasionally stop to listen for other leaders in the network.

Figure 9:
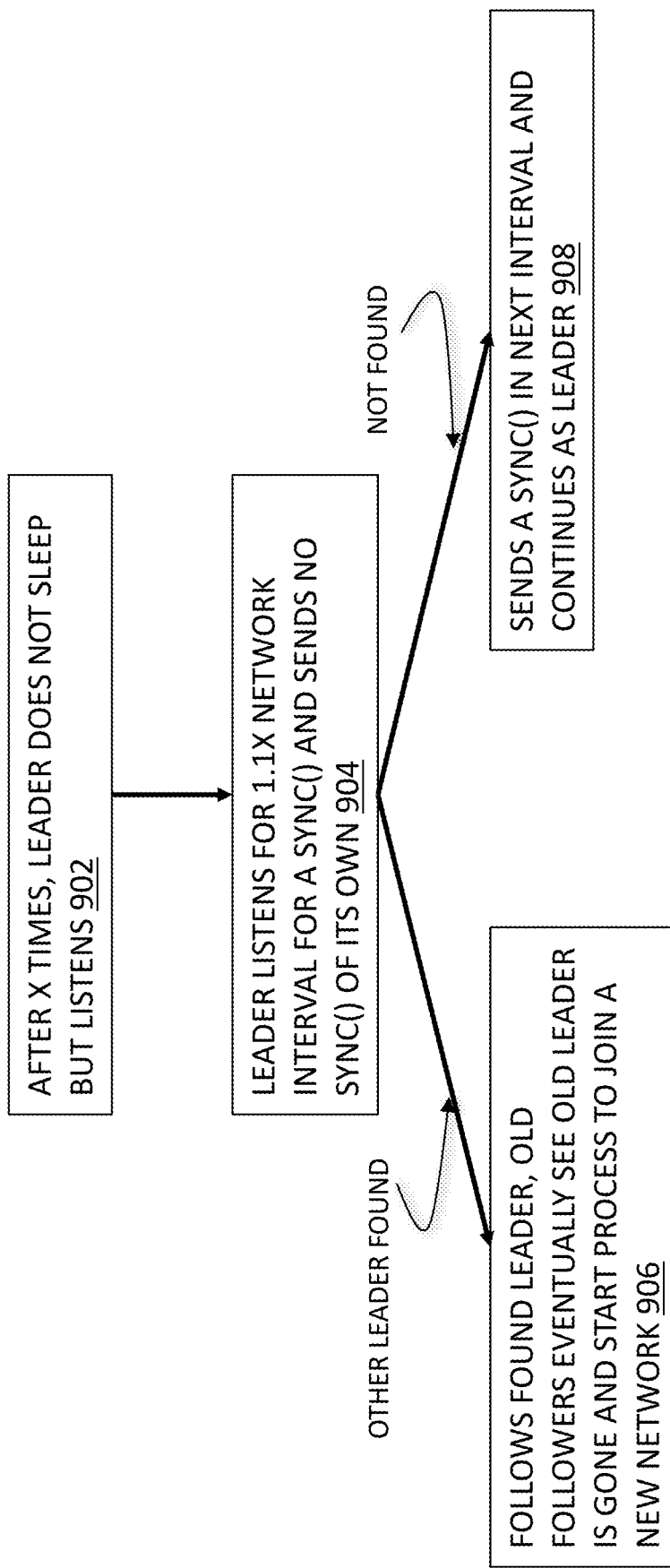
FIG. 9 depicts a leader election process.
Figure 10:
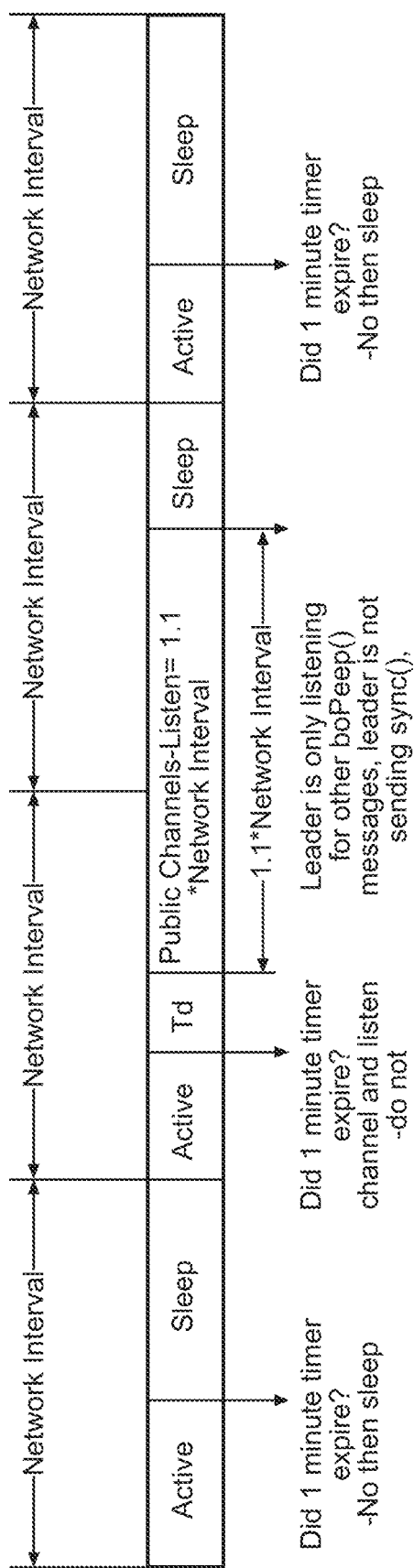
FIG. 10 depicts a sleep cycle process.

In that regard and referring now to FIG. 9 and FIG. 10, at a regular interval (such as every 60 seconds), just after the network wake period ends, instead of going to sleep the leader remains awake (step 902) and goes to the public channels and listens for advertising messages to determine whether other nodes are leaders of other networks that are in range (step 904). During this time, the leader intentionally skips sending a sync( ) message for the next network cycle. This causes the leader's own followers not to send boPeep( ) messages in that cycle. During this time, the leader listens for any boPeep( ) messages on the public channels. If the leader hears one, it means that there is another leader within range operating under the same network name. The leader relinquishes leadership and begins to follow the other leader (step 906). The leader's old followers (through leader health monitoring) will realize their leader is gone, and will also go to listen on the public channels and will find a new network. To maintain the leader health monitoring, a leader health counter is maintained and incremented by one when the leader is heard in a network interval and decremented by one in a network interval where the leader is not heard. When the leader health counter reaches zero, the node presumes that it has lost its leader and begins the process of finding a new leader. Therefore, this handles the difficult case where a network is split in two. Each half elects its own leader but is still operating under the old network name. When these two groups come back into range of one another, the behavior described above causes them to be rejoined. The new leader also sets a new awake time interval for the network by including the network size n=#peers+1 in the payload of the sync( ) message. The leader's radio bases the network size on the number of peer instruments reported by its instrument software (active or lost) plus 1 (the leader). The network size (peers+1) is also sent in each boPeep( ) to prevent more than the allowed number of instruments from joining one network.

If a new leader is not elected (step 908), the leader continues in its role as leader and resumes sending sync( ) messages at the beginning of network intervals.

The leader also needs to be aware of a special situation called "Leader of none." Considering the case where all peers have left a network (no active or lost peers), the leader should not continue to operate the network without followers. Instead, the instrument will relinquish leadership and will return to listening on the public channels, ready to form a new network when another instrument is detected.

In embodiments, the wireless network may use frequency hopping, where every network interval occurs on a different channel, or frequency. An exemplary process and architecture for frequency hopping is described herein. In an embodiment, the channels (16 channels in the case of an IEEE 802.15.4 network) may be divided between active channels and public channels. Preferably there are two public channels and the remainder of available channels are active channels. The active channels may be used in the hopping sequence, whereas the public channels are used for forming/joining/rejoining networks, as described above. Preferably, public channels will be non-adjacent and should utilize frequencies that are not heavily utilized (e.g., between WiFi bands, managed spectrum, etc.)

Active channels may be, by default, all channels other than the public channels; however, channels can be "blacklisted" by using an active channel mask. Some active channels may be blacklisted due to local regulations or due to high traffic levels known to be on the channel. For example, a wireless video camera operating on a channel will create heavy traffic on that channel, and therefore it may be desirable to avoid that channel.

During operation, a different active channel may be used for each network cycle, called frequency hopping. The order of the hopping may be a repeating nonrandom sequence or a pseudorandom sequence, such as one calculated using a linear congruential generator (LCG).

The inputs to the generator ("hopping parameters") are a multiplier, intercept and a seed. At power up, each node randomly chooses a valid set of hopping parameters and saves them, in case it is ever called on to lead a network. In an embodiment, using the recommended settings with public channels 4 and 9 in a 16 channel environment, and no channels blacklisted, the algorithm generates hopping sequences where the next channel is always at least 2 channels away from the current channel (non-adjacent). If either the public channels or masks are modified, this may not always be the case.

When a node wins a leader election, it sends its hopping parameters in the advertising message (boPeep). Followers compute the sequence, using the leader's parameters, and advance to the next channel, waiting to hear the leader's sync( ) message. With each network interval, the leader and all followers advance one step in the sequence.

Leaders and followers transmit the hopping parameters on both public channels in the advertising message (boPeep) near the end of every network cycle, to allow other instruments to find the network. An instrument wanting to join a given network, need only listen on one of the public channels to compute the proper sequence and next channel. The node advances to the next channel and waits for the leader's sync( ) message to begin hopping.

The LCG calculates the next channel using the formula:

$$X_{n+1} = (aX_n + c) \bmod m$$

where X is the sequence of pseudorandom values, and
m,m>0 the "modulus"
a,m>a>0 the "multiplier"
c,m≥c≥0 the "intercept"
$X_0$,m>$X_0$≥0 the "seed"

These values are all integers that define the sequence. In a sequence where the modulus is known, for example a network with 16 total channels, the modulus may be assumed by all of the nodes rather than transmitted in a sync( ) message. Further, when a public channel or a backlisted channel is the result of the sequence the node can either choose the next non-reserved channel or the next channel in the sequence.

Using wireless technology introduces certain information security risks. The system may include measures that prevent unauthorized listening-in to instrument readings and status, prevent injection of false/misleading information into a network (like false alarms), and prevent jamming or other denial of service attacks that would prevent effective use of the wireless feature set.

Wireless message contents may be encrypted by default. Encryption means that the contents of a wireless message are garbled and unrecognizable unless a receiver knows the secret password, called a "key." The wireless network may use Advanced Encryption Standard (AES) encryption with a 128 bit key length for messages sent wirelessly. This encryption is standard for the 802.15.4 radios used. These radios may have built-in hardware encryption engines, so using encryption has minimal impact on throughput or power consumption.

Multiple approaches to wireless network security may be possible. In one approach, each wireless network-compatible device may leave the factory with a default key. The key is kept private, and it is not visible to the end user in any device or software—it is embedded (and, in embodiments, hidden) within the instrument source code. Since all instruments have the same default key, there is no need to transmit it between devices, just a need to agree to use the default key. In another approach, if the user wishes, they can enter a customer key into their devices, using the instrument UI, iNet, or other maintenance tool—again, once entered, this key is never displayed. To ensure that new instruments can be added to a network using a custom key, the key may be shared as part of the binding process.

The wireless network's system of binding also helps protect from unauthorized access to a given network. To participate in a given network, a user first learns the network's unique name through close contact with an instrument that is already a member of the group (via IR or Near-Field Communications).

Binding is the process of joining two or more wireless devices into the same wireless network. Implied within binding is the understanding that the devices want to share alarms and/or information—that is, there is no network without intent to share information. The binding process of the present disclosure does not include the concept of being connected for future use. If a node is connected to the network, it is sharing and broadcasting. No further authentication is needed if the devices are bound to the network using the touch process, described further below. Anyone in the network is trusted with allowing a new entry. Binding is similar to the process of "pairing" used in point-to-point networks, including Bluetooth. However, the network 104 is a mesh network, so more often than not, binding is actually bringing a new device into an existing network including several other devices, so "pairing" is not entirely accurate because it implies only two devices are involved. That said, any reference to "pair" or "pairing" herein can encompass the binding described herein. In certain embodiments, the mesh network 104 may be established in instruments 110 and/or 108 and/or gateways by an NFC binding process where the network parameters are passed and peer networks in area monitors may be established by choosing the same named network.

The wireless network may have multiple binding methods, such as Named Network and Secure Simple Binding.

Named Network is implemented in the wireless network as a list of predefined networks, say "A" through "J", which will be called "Channels" in this example, though they may have nothing to do with the frequencies used. Each wireless network-compatible device may come pre-programmed for these Channels when they leave the factory. Connecting two devices may be as simple as making sure they are both set to the same Channel (letter). Two instruments set to the same Channel may connect automatically at power up if they are within range of one another.

With Named Networks, the selected channel is defaulted at the factory, and remembered through power cycles. At power up, a device may seek out and connect to any other devices in range and set to the same channel. Because their primary wireless network use case is replacement of daisy chain cables, area monitors may use Named Network as their primary binding mechanism. Area monitors may ship with a default network setting and connect "out of the box". More sophisticated users can set up different groups of area monitors by using different channels for different groups.

Area monitors may remember their network settings and try to reconnect every time they are powered up. This means that area monitors could connect unintentionally with an existing network. This problem should be manageable, given the smaller number of these devices and the generally-higher level of user expertise, instruction, and training.

Secured Simple Binding (SSB) may be implemented in the wireless network by passing network "secrets" (like the PIN in Bluetooth). SSB takes advantage of a second, simple, short-range communications technology, called an Out-Of-Band (OOB) link, to pass a network's credentials to a joining member. In the case of the wireless network, an instrument's infrared may be used (e.g. IrDA) and Near Field Communications (NFC) for the OOB link.

Portable instruments with the wireless network compatibility may use Simple Secure Binding (SSB) as their primary mechanism. Near Field Communication (NFC) may be used for the out-of-band (OOB) link. The portable binding implementation may be biased towards 1) preventing unintended connections and nuisance alarms, and 2) ease of connection. In embodiments, portables may forget their network associations at power down. When the instruments power up, they are in a disconnected state but are always watching the NFC interface for another instrument. When two portables are placed together, they connect to the same network, with no other user intervention required. The simple action of touching the instruments together ensures the connection is deliberate.

There are three scenarios to consider: 1. If neither device is currently in a network, the two devices may form a new network and connect; 2. If one device is already participating in a network, it passes the existing network credentials to the new instrument and allows it to join the existing network; and 3. If, on the other hand, both devices are already part of different networks, the binding process fails and both instruments display a screen asking the user if they want to leave their old network. After at least one of the users leaves their existing network, the binding process can be repeated with success.

Area monitors may also implement Simple Secure Binding (SSB) as a secondary mechanism. This is a robust method for connecting any two area monitors. Regardless of how their configurations have been changed (custom encryption, different channel settings, etc.), performing SSB will arbitrate these settings so they connect. In the same way, a rental or replacement monitor can be added to the network without the need for an expert user, specialized software (e.g. ISAS software or iNET), and the like. SSB on the area monitor may also be used to connect a portable instrument to join into an existing area monitor network.

The following information may be communicated during the Secure Simple Binding process: Low 3-bytes of the MAC Address, Proposed Network Name, Active Channels to be Used, Primary Public Channel, Secondary Public Channel, and Custom Encryption Key (if used).

Once this information is exchanged, the instruments may have all the information they need to complete a connection. A confirmation tone (and/or vibratory signal) may be emitted to indicate that the instruments no longer need to be held together.

After two instruments exchange the binding information, they must decide which instrument's settings will be used in the network. If one instrument is already part of a network (i.e., it sent an "Allow" message), its settings are used. If neither instrument is part of a network, the settings of the instrument with the lower MAC address are used, except in the case where one instrument has custom encryption enabled and the other has default encryption enabled. In this case, custom encryption is considered more robust and will be used.

After arbitration, the instruments apply the appropriate settings to the radio module and attempt to connect. When the connection is successful (indicated by receipt of at least one other instrument's status message), a confirmation tone may sound and the wireless icon may be illuminated. The connection process is expected to complete within a few seconds.

With respect to performance, range is a function of link budget minus path loss. Link budget is the difference between transmitter output power (including antenna gain/loss) and receiver sensitivity. Output power is limited by regulations and/or battery life, while receive sensitivity is a function of electronics design quality and data rate.

Shown below is the free-space path loss equation that predicts range (d) of a RF signal.

$$d = \frac{\lambda}{4\pi} \sqrt{\frac{P_t G_t G_r}{P_r}}$$

$P_t$ is the transmitted power, $P_r$ is the received power
$G_t$ is the transmitter, $G_r$ is the receiver antenna gain
d is the distance between transmitter and receiver, or the range
Lambda is the wavelength $$\lambda = \frac{c}{f} = \frac{\text{Speed of light}}{\text{Frequency}}$$

Eqn. 1

Using a radio module as example: $P_t$=3 dbm; $P_r$=−100 dbm; and d=250 m, including a conservative fade margin of 15 db. Fade margin captures the practical sensitivity of the receiver, and includes antenna polarization, reflections, multi-path interference, etc. A fade margin of 6 dB would represent ideal conditions (clear weather, antennas aligned, etc.); a more conservative number might be 15 dB.

Practical range in an industrial setting is different from a free-space environment. Through a typical warehouse environment, actual range for the radio modules may be about 75 m. Line of site through a large factory may be approximately 100 m. Actual range may vary widely depending on the environment, and the mesh topology extends the effective range dramatically. Height off the ground may also impact range.

In embodiments, the mesh network 104 may be designed to operate with between 2 and 25 instruments in a given network. If there are too few nodes for an environment, the network may not have enough paths to be effective. When networks grow too large, the individual nodes have to compete for the shared resource of network bandwidth. Therefore, in embodiments, the optimum network size is typically between 8 and 15 instruments.

Because of the frequency hopping and the short transmission time of 802.15.4 radios, hundreds of instruments can operate within the same area without interference, provided they are operating on different networks, as described herein. The discussion herein with respect to joining/rejoining a network provides details on how network size is controlled.

Hardware enabling wireless network-compatibility may include: An 802.15.4 Radio system on a chip ("SoC"), supported by a network operating system (typically a pre-certified module); memory IC and circuitry that implements a shared memory interface; and a precision timer used to maintain network synchronization. In some embodiments, a barometer may also be included.

Hardware enabling wireless network-compatibility may be implemented directly on the portable gas detecting instrument mainboard. For models of the portable gas detecting instrument without wireless functionality, these parts are depopulated. In other embodiments, such as for area monitors, the hardware enabling wireless network-compatibility may be implemented in a pluggable PCB (module), such as for area monitors. The module may also add a GPS receiver (which may or may not be populated). While not technically part of the feature set, the GPS feature may be implemented as part of the script running on the Radio SoC. Although a slightly different radio module may be used on area monitors, the other circuitry may be identical to the hardware implementation for portable instruments (other than GPS).

Figure 11:
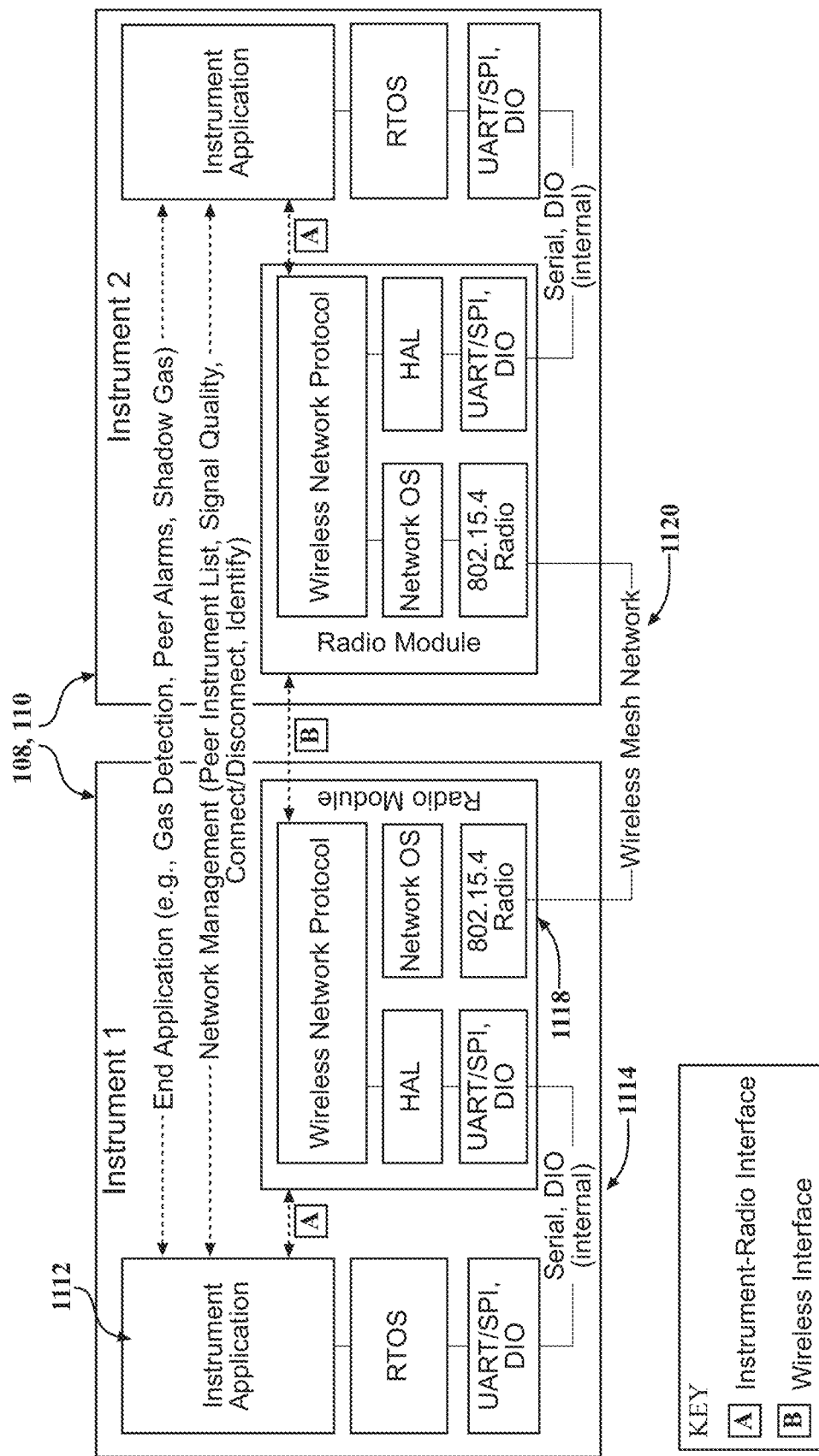
FIG. 11 depicts the wireless network mesh architecture.

FIG. 11 depicts the wireless network architecture. In FIG. 11, the structure of two instruments 108, 110 with radio modules that interact in a wireless mesh network is depicted. Each of the instruments are depicted as being similar, but the instruments may be different instruments, and their structures may be that of a portable device, area monitor, or the like. Each instrument may have one or more end applications, such as gas detection, peer alarms, shadow gas, and the like. Each instrument may be involved in network management, such as with activities such as peer instrument list, signal quality, connect/disconnect, identify, and the like. An instrument-radio interface 1114 (e.g. serial, digital I/O) is shown operating to connect the instrument application component with the radio module 1118 and its wireless network protocol. A wireless interface 1120, the wireless mesh network, is shown between the radio modules 1118. FIG. 13 depicts the wireless network fitting in a 7-layer OSI Model.

In embodiments, the same wireless radio useful in the wireless network may be used in a master-slave relationship between an instrument and its accessory. In this case, each accessory device would include a similar radio as the instrument. Possible accessories include auxiliary alarm devices, smart sample draw pumps, or even a bridge to a smartphone or other mobile gateway or computing device. The bridge would communicate with the instrument using the wireless network technology but convert communications to another format. The other format could be Bluetooth to connect to a smartphone 118, or an industrial protocol like HART or WirelessHART, or WiFi. Accessories could also include additional sensing devices (gas, workers vital signs, or otherwise) that would share the display, datalog, and alarms already found in the gas detector. Another example is an adapter that holds an inline benzene filter, and communicates with the instrument to indicate filter state (engaged/bypassed) or filter age.

In certain embodiments, the parts of a gas detector (sensor, display, alarm, etc.) may actually be separate devices, connected wirelessly. With this model, a sensor could communicate with a smartphone 118.

Figure 12:
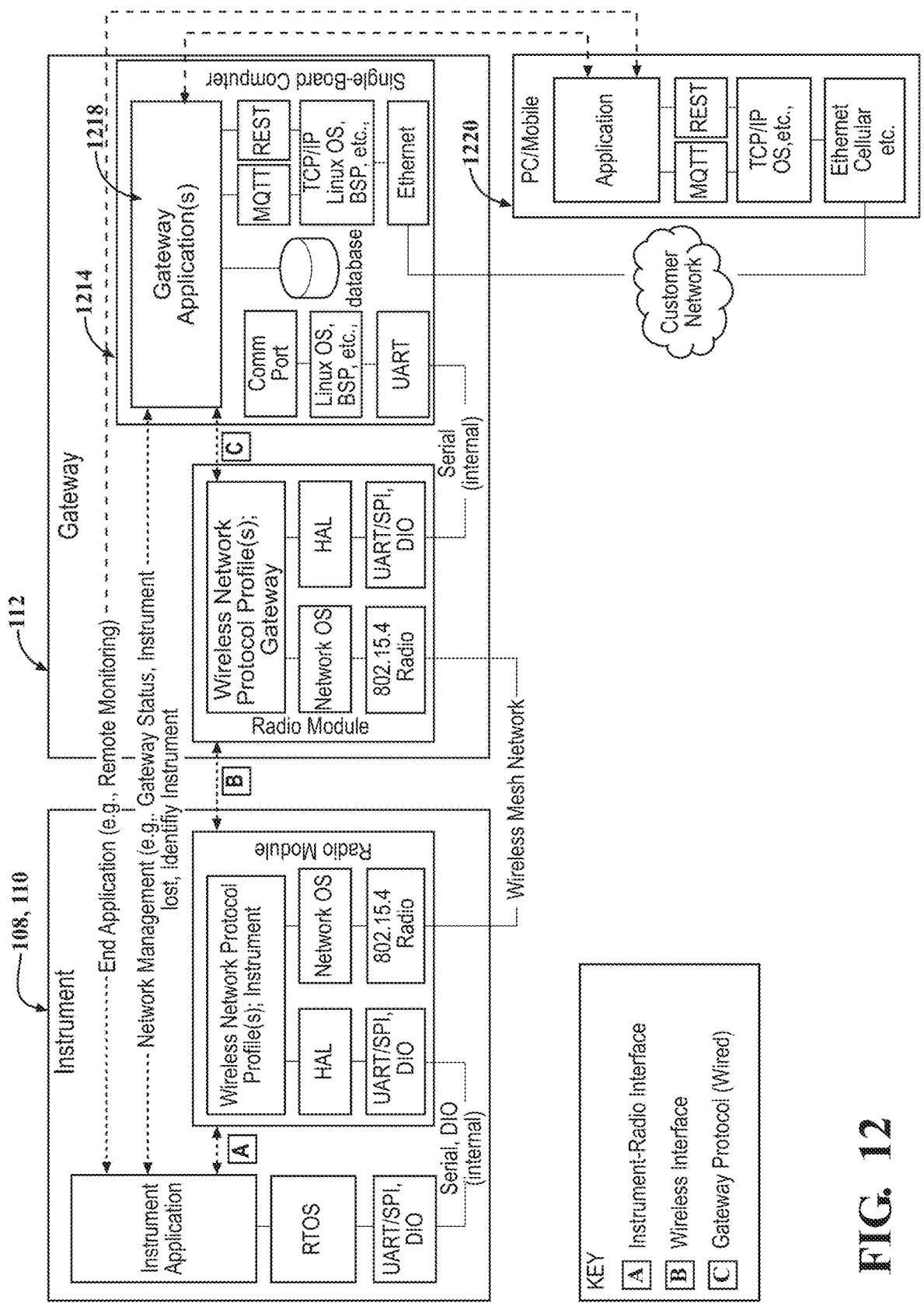
FIG. 12 depicts how the hardware enabling wireless network-compatibility can be extended to a platform using gateways to the Internet.

FIG. 12 depicts how the hardware enabling wireless network-compatibility can be extended to a platform using gateways 112 to the Internet for the end application of remote monitoring and the like. For example, the gateway device 112 may receive data from an instrument 108, 110 through the mesh network 104 and transmit it to the cloud via cell, Wi-Fi, Ethernet, or satellite. The gateway device 112 may be intrinsically safe, extended battery power (such as 7 days), rugged, and wall-mountable or transportable. FIG. 12 depicts an instrument 108, 110 structure similar to the ones shown in FIG. 11, but the instrument 108, 110 is in communication with a gateway 112 in this instance via a wireless mesh network, such as the mesh network 104. The gateway 112 may include a radio module 1118 with a serial connection to a single-board computer 1214. The single-board computer 1214 may include a gateway application 1218 that is in communication with a database, and with a network through a communications protocol, such as the internet, Ethernet, cellular, WiFi, satellite, and the like. The network may ultimately allow an end user to connect to the worker safety system with a PC/mobile device 1220. The gateway 112 is shown in FIG. 1 where wireless network-compatibility is extended to a platform using gateways 112 to the Internet. Data may be transmitted between devices using the mesh network 104 and data may be transmitted to the gateway 112 using the mesh network 104. The gateway 112 may transmit data to the cloud via cellular technology, WiFi, and/or satellite where it may be used in a variety of applications as further described herein. For example, when a gas detector goes into alarm and the data are transmitted back to the cloud, a remotely located supervisor may deploy a response team, send a message back to the gas detector, call the worker with the gas detector on a separate phone or on the gas detector itself if it possesses telecommunications functionality, ask another nearby worker to check in on the worker, and the like. Data may be aggregated over time regarding alarms and other safety-related data to identify risks or safety-related issues in an area, as is described herein.

With continuing reference to FIG. 1, data may be transferred from the instruments 108, 110 to other devices, such as mobile devices, tablet computers, local computers, beacons, and the like using communications protocols such as NFC, Bluetooth and the like. In an illustrative example such as that depicted in FIG. 1, an API 114 may be used to transfer data between the instruments 108, 110 and smart devices 118/mobile gateways 131, wherein the smart devices may use the data itself or transmit the data on to a remote server 130 or the cloud via WiFi, cellular, satellite or the like. In some embodiments, the instruments 108, 110 may transmit data directly to a remote location, such as by having integrated WiFi, cellular or satellite technology. There may be two-way communication through the device 118 or mobile gateway 131 such that remote computers or applications running in the cloud may be used to control, configure or otherwise communicate with the instruments 108, 110 through the device 118 or mobile gateway 131. For example, a report from a gas detector or a group of gas detectors that a gas threshold has been reached may be sent to a remotely located supervisor. The supervisor may be enabled to take many actions through the worker safety system, such as communicate back to the instrument, change the display on real-time signage, take control of a local device, such as a drone-mounted gas detector or camera, and the like. In embodiments, the worker safety system may automatically take control of local devices or instruments based on a report from an instrument.

Figure 3:
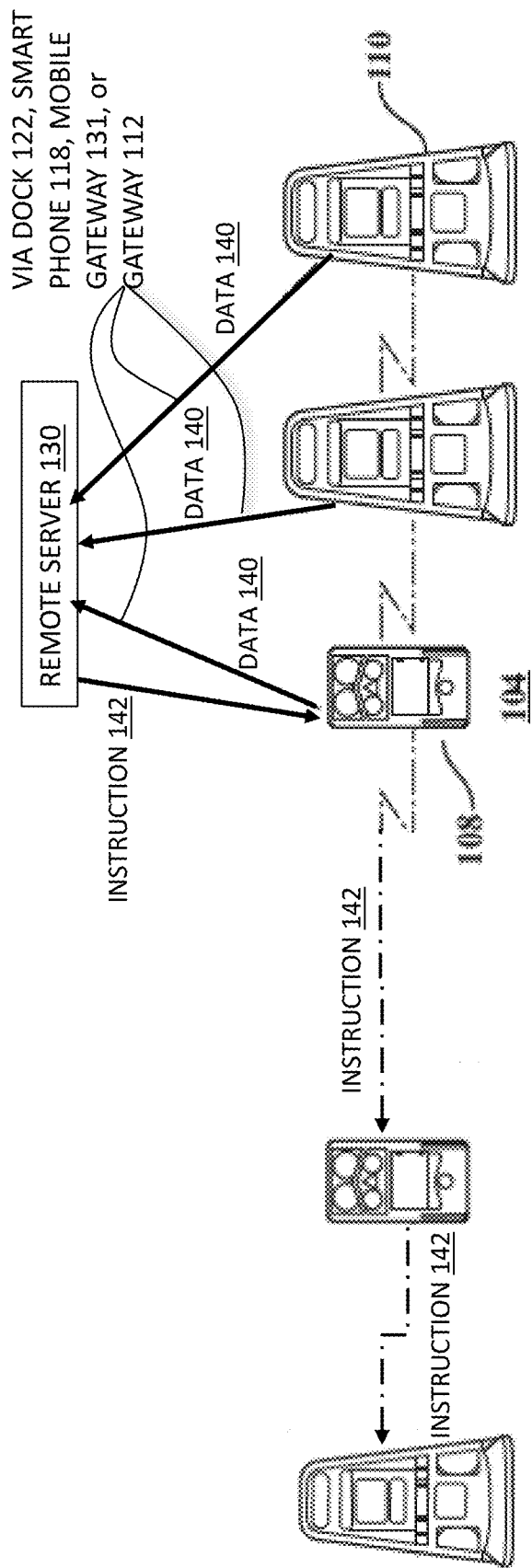
FIG. 3 depicts a system for propagating an alarm in a mesh network.

Referring now to FIG. 3, a plurality of portable environmental sensing devices 108, 110 in a work area adapted to communicate with one another in a mesh network 104 are shown. In FIG. 3, some devices 108, 110 are shown in communication with a remote server 130 or computer via a communications facility, such as a dock 122, gateway 112, mobile gateway 131, or smart phone 118. Other devices in the mesh network 104 may not be in direct communication with the remote server 130 or computer and instead rely on receiving data or instructions through the mesh network 104 from other devices 108, 110 that are in communication with remote servers 130 and computers. The communications facility transmits data from at least one of the plurality of portable environmental sensing devices to a remote computer, wherein the remote computer is configured to monitor at least one of a hazardous condition and an activation of a panic button in the work area based on data from the at least one of the plurality of portable environmental sensing devices. The remote computer is configured to receive, from the at least one portable environmental sensing device, an alarm related to the hazardous condition or activation of panic button, and transmit to any of the portable environmental sensing devices an instruction to be propagated throughout the mesh network. The instruction may be a request to check the safety of a user of the at least one portable environmental sensing device, an evacuation instruction, a risk mitigation instruction, and the like. The remote computer may further be configured to display the location of the portable environmental sensing devices in a map of the work area and transmit the map for display on any of the portable environmental sensing devices. The data transmitted by the communications facility can be sensed gas data, wherein the hazardous condition is based on the sensed gas data exceeding a threshold. The remote computer may be further configured to display the sensed gas data in a map of the work area, wherein a size of the representation of the gas data is proportional to the gas level. The remote computer may be further configured to request an emergency response at the location of the at least one portable environmental sensing device.

In an illustrative example, applications resident on the smart device may send data to the cloud. Applications served by a cloud or other remote server 130 may receive data sent by smart devices or from the gateway 112 and provide web interfaces for various end use applications, such as monitoring, mapping workers and alarms/events, notifications, alarms, e-permitting, compliance, emergency response, safety inspections, accountability, risk management, compliance, lone worker solutions, worker networks, 3$^{rd}$ party integration, device/instrument control, and the like, as will be described further herein.

Continuing with FIG. 1, the instrument 108 is depicted as in communication with a beacon 102. The beacon 102 allows for broadcasting information to the instrument 108. In embodiments, the data broadcast by the beacon 102 may be stored by the instrument 108.

FIG. 1 also depicts an NFC tag in relationship to the instrument 108 and thus other components of the system. For example, data collected by the instrument 108 from the NFC tag may be used to tag gas detection data to enable quickly identifying the gas detection instrument operator and location to make the gas detection information more actionable.

Gas detection instruments, portable environmental sensing devices, and other safety devices with integral technology that collects temporary assignment and location information may enable valuable insight into gas exposure data, safety events and user behavior, while being useful when managing assets and investigating potential issues. Tagging gas detection data and other collected data allows anyone reviewing the data to easily see who had the instrument and where the operator was using it, making the information more actionable. This disclosure may refer to gas detection instruments and area monitors in the description and examples of the systems and methods. Such references are meant to apply to the components of the system described herein, such as environmental sensing device 108, area monitor 110, gateway 112, API 114/Smart Device 118 or mobile gateway 131, it should be understood that other environmental sensing devices, area monitors, and components may be used with the embodiments described below.

NFC tags are short range, small, non-powered tags with a small memory and a radio chip attached to an antenna. Having no power source, they draw power from the device that reads them, thanks to magnetic induction. When a reader gets close enough to a tag, it energizes it and transfers data from that tag. The assignment tag may be small, light, require no battery, and may withstand harsh outdoor environments. Assignment tags may be in multiple styles, such as a sticker tag, a waterproof sticker tag, an outdoor tag, a keychain tag, and the like. The assignment tags may be continually overwritten as needed or locked so that they cannot be reprogrammed.

The gas detection instruments with NFC technology may support multiple assignment types, such as recurring and temporary assignments. A recurring assignment may persist with the instrument when the instrument is restarted. A recurring assignment may be made using an application or software, such as iNet Control, DSSAC (Docking Station Software Admin Console), or accessory software resident on the instrument or other component of the system that communicates with the instrument. A temporary assignment may be made via an application or through the instrument settings. Temporary assignments may overwrite recurring assignments and stay with the instrument until it is restarted. Upon restart, an instrument with a temporary assignment may revert to the recurring assignment, if one is available. If there is no recurring assignment, the instrument may be unassigned. Alternatively, to remove a temporary assignment, the assignment tag may be re-touched to the instrument when the assignment is no longer needed.

Figure 14:
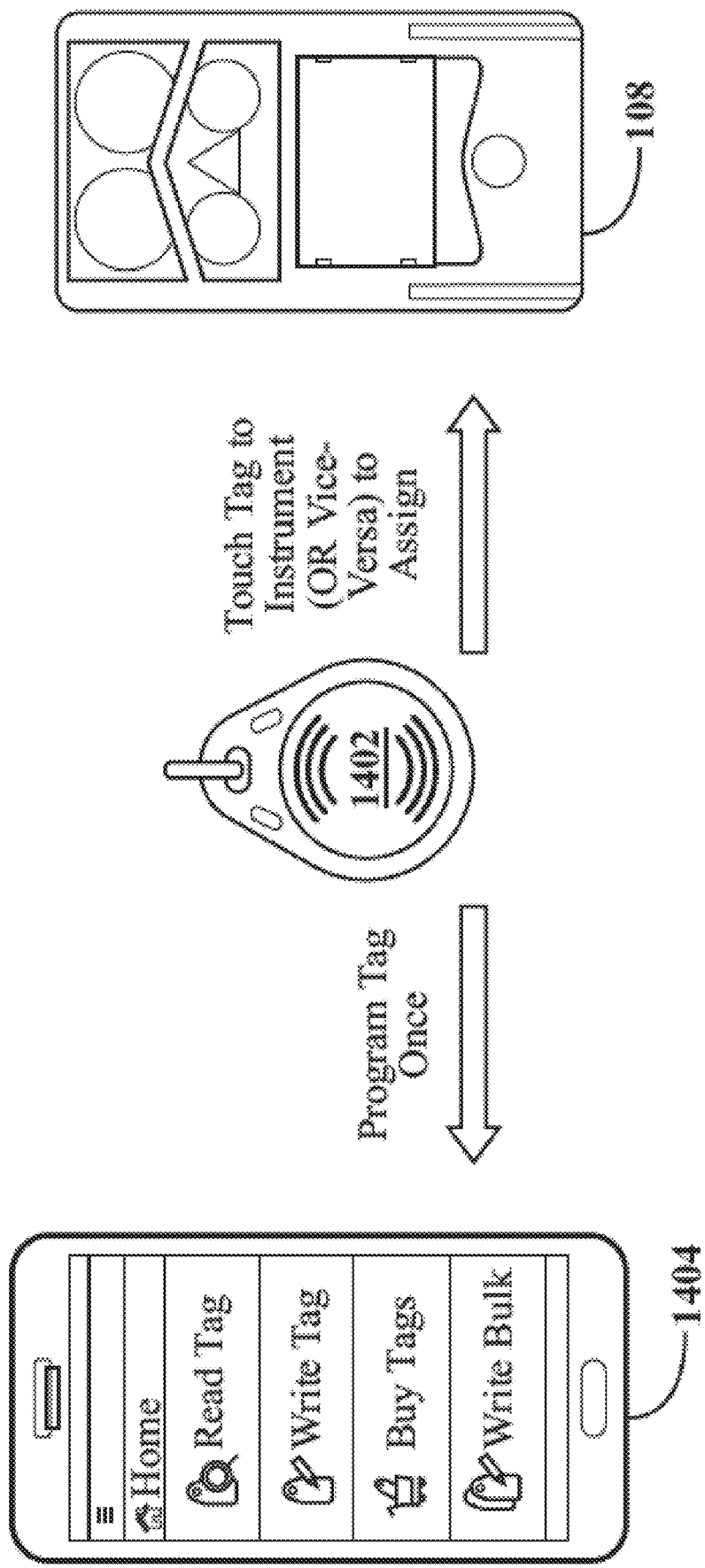
FIG. 14 depicts a method of the disclosure.

In an embodiment, and referring to FIG. 14, in order to make use of the NFC assignment capabilities of the gas detection instrument, assignment tags 1402 may be programmed with an assignment using an assignment application 1404 or other assignment software. The tags may need to only be programmed once. The tags may then be distributed to instrument operators or installed at a location. Then, instrument users may touch the gas detection instrument 108 to an assignment tag so that the NFC radio in the instrument may sense the assignment tag.

Assignment tags for identifying individuals may be programmed with a variety of identification data, such as name, size and weight (such as to be able to calculate a person-specific gas hazard threshold), typical work locations, job function, security and or authorization information which may include whether the user is authorized to use a specific instrument or be in a specific location, typical instruments used by the user, pre-existing events caused or experienced by the user such as prior alarms or gas events, languages known by the user, prior alarms, and the like. Assignment tags for identifying locations may be programmed with a variety of data, such as location within a space, GPS location, equipment at the location, fuel sources at the location, known hazards at the location, typical gas concentrations for the location, other environmental conditions for the location, recent gas events at the location, recent man down alarms triggered at the location, recent alarms triggered at the location, recent messages triggered at the location, and the like.

Figure 15:
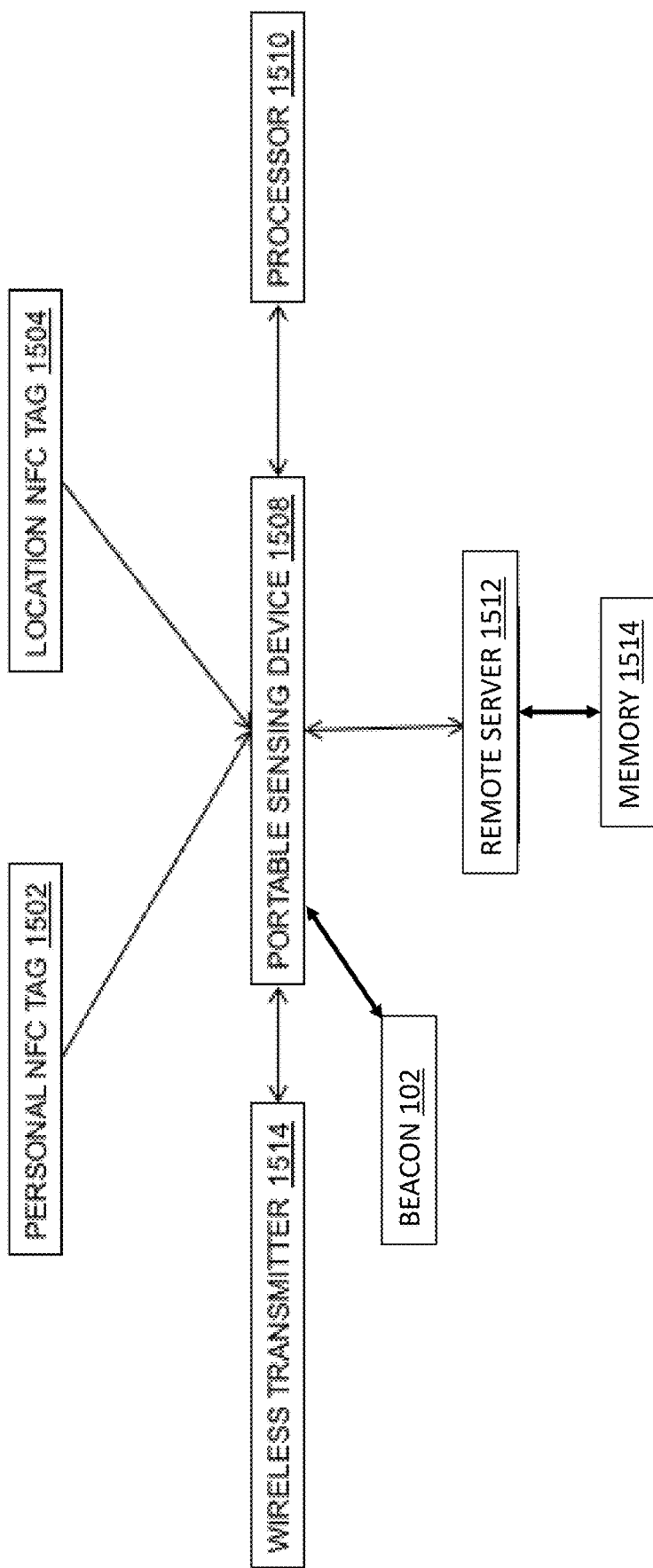
FIG. 15 depicts a block diagram of an embodiment of the disclosure.
Figure 16:
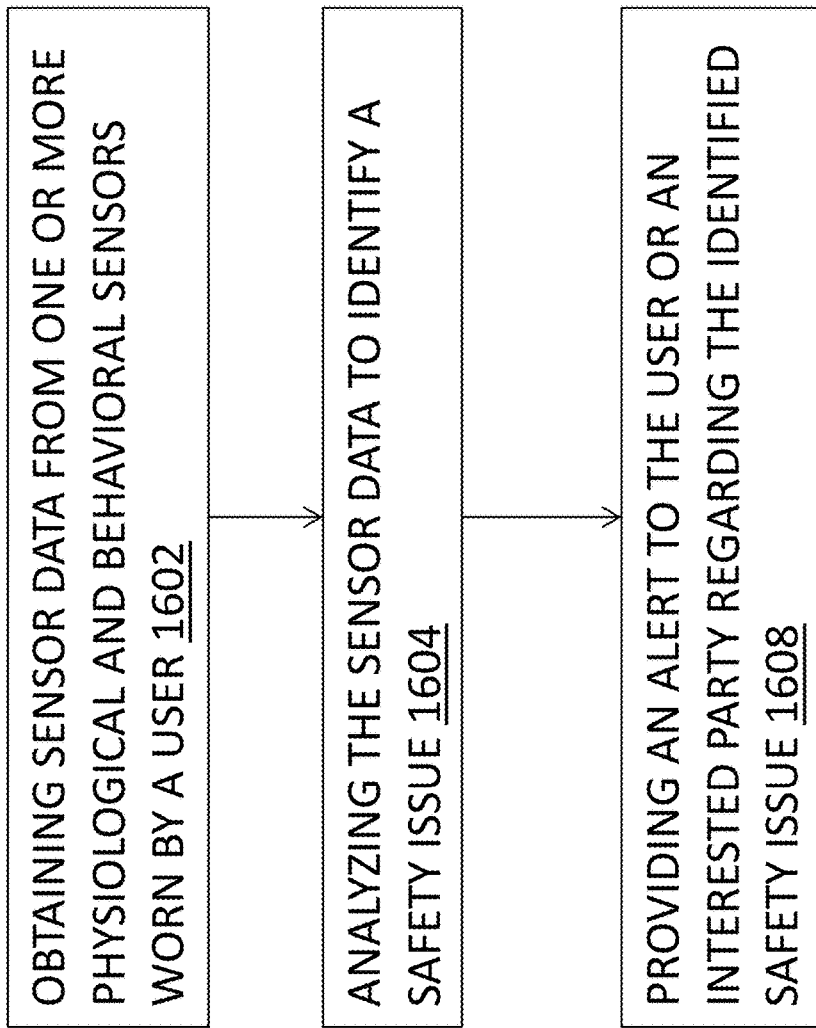
FIG. 16 depicts a method of providing safety alerts.

Referring now to FIG. 15, as described herein the worker or industrial safety monitoring system may include a personal NFC tag 1502 assigned to a worker, wherein the tag assigned to the worker comprises identity information of the worker, such as name, size, weight, job title/function, company, languages spoken, certifications/licenses, accommodations, approved tasks, approved locations, approved equipment, hours worked, typical work location, a typical instrument/equipment used, a pre-existing concern, a prior alarm, a prior gas or safety event, any prior radiation exposure levels, a prior message, a security clearance, and the like.

NFC assignment tags 1502 may be carried by workers or attached to a name badge, employee ID, hardhat, tool belt, or other personal item. The system may also include and/or interact with a plurality of location NFC tags 1504 assigned to locations, each location tag placed in a location comprising information of the location in which the location tag is placed. Certain parameters associated with the location may be programmed into the NFC tag, such as for example, location name, latitude/longitude/GPS coordinates, typical temperature, typical humidity, a level of authorization needed to enter/service the location, the type of equipment in the location, a certification/license needed to operate equipment at the location, personal protection or safety gear required, instructions to be followed, instructions for on-site equipment, gas detection instrument dock nearby, a fuel source at the location, a known hazard at the location, a typical gas concentration for the location, an environmental condition for the location, a recent gas event, a recent man down alarm, a recent alarm, a recent message, and the like.

A portable environmental sensing device 1508 detecting data of an environmental parameter may be configured to (i) read the personal NFC tag and store the identity information of the worker using the sensing device, (ii) read at least one of the plurality of location NFC tags and store the information of the location of a location tag read by the at least one portable environmental sensing device, (iii) associate the location information, identification information, and/or any parameters detected by the sensing device and store such associated information, and (iv) transmit any of the information above to other components of the system. Note that the transmission of data may be accomplished in accordance with the methods described herein, such as via a P2P network, mesh network and/or to and through the cloud in manners described herein. Components receiving and operating on the data may be as described herein. In accordance with the description herein at least one processor 1510, which for example may be located in another instrument 108/110 or part of the remote server 130, may be in communication with the at least one portable environmental sensing device 1508 and may receive any of the information above (i)-(iv) from the at least one portable environmental sensing device 1508. In embodiments, the at least one processor 1510, itself, may be programmed to determine an environmental parameter of the worker using the sensing device 1508 and the location of the determined environmental parameter based on the data it received from sensing device 1508. The system may further include a remote server 1512 comprising a memory 1514 in communication with the at least one portable environmental sensing device 1508 that stores the detected data and the information in a data log. The system may further include a wireless transmitter 1514 that transmits, including in the manners described herein, the detected data and the information to a cloud-based or other remote server 130 or log. The transmitter may be the gateway 112, API 114/Smart Device 118 or mobile gateway 131 as described herein in connection with FIG. 1. In embodiments, the wireless transmitter 1514 transmits the detected data and the information to another portable environmental sensing device 1508 or other safety device. For example, a detected event on a first portable environmental sensing device may be transmitted to one or more other portable environmental sensing devices, gas detection instruments, safety devices, servers, computers, smartphones, and the like in the form of a message, an alert, or raw data, wherein the transmission may include the information derived from the NFC tags.

In an aspect, workers may wirelessly enter a name and a location into the device 1508 or instrument 108/110 simply by tapping the NFC assignment tag to the instrument. Alternatively, location information may be automatically collected via GPS or other location sensing technology. Once the user and/or site information has been transferred from the assignment tag to the instrument, data recorded by the device 1508 or instrument 108/110 may be tagged with the user and location information and saved, in the instrument data log or wirelessly transmitted to a cloud-based or other remote server 130.

In another example, each employee may receive his or her own assignment tag identifying them which can be attached to a name badge, employee ID, or other personal item. Then, each day, the employee may pick up an instrument from a shared pool or tool crib, wherein the instruments may be compliant, calibrated, and/or bump-tested, at the start of his or her shift. When the instrument is touched to the assignment tag, the assignment is complete. The device may be further configured to the user's needs and/or specification, and may also include data about the user. This may be an example of a temporary assignment. In another example of a temporary assignment, the assignment application may be used to assign the location "Tank 1" to an assignment tag. The tag can then be installed at the entrance to Tank 1. When instrument operators enter Tank 1, they can touch their instruments to the tag and the location assignment will be saved to the instrument. These examples may describe separate scenarios or a single scenario. For example, the instrument operator may temporarily assign themselves an instrument from the tool crib, then assign the 'Tank 1' location upon arrival to Tank 1. Thus, data will be tagged with both the user identification and the location at which other data are collected.

In embodiments, using NFC tags, a permission-based perimeter fence may be established. For example, if only certain users are allowed to enter 'Tank 1', only those users may be able to assign the 'Tank 1' location to their instrument, which may then be used for electronic entry to 'Tank 1', for example.

In embodiments, the system of FIG. 15 includes a beacon 102, which may repeatedly transmit an informational message, the beacon's payload.

In embodiments, customized on-screen messages may be provided to the gas detection instrument with specific information or instructions, such as instructional text to assist users in knowing how to react properly in the event that an instrument alarm occurs. The messages may be programmed into the instrument itself or any system component in communication with the instrument and automatically triggered, such as through detection of one or more particular gases or detection of a threshold amount of gas. In other embodiments, the messages may be manually delivered, such as from a supervisor, another instrument user, a facility manager, an instrument manager, a control center, or the like. Certain messages may display during the instrument start-up sequence. Certain messages may display during gas or other safety events. In embodiments, a unique instructional message may be set for each of these events for each sensor: gas present (alert, low alarm, and high alarm), STEL (short-term exposure limit), and TWA (time-weighted average). For example, an alarm action message may be programmed for each all alert/alarm set points for each sensor of the gas detection instrument to tell the user, in their native language, whether they should wear a respirator, leave the area, seek shelter or take whatever action is dictated by the company emergency response plan. Alarm action messages mean that an instrument user need not be trained to interpret and understand the meaning of all gas readings, rather the user simply need to read the display and heed the instructions. Alarm action messages may change based on assigned user or location.

In embodiments, the gas detection instrument may feature audible, visual, and/or vibrating alarm indicators that may be used in multiple modes. For example, the audible indicator may be capable of delivering a tone at a programmed decibel level, in embodiments, 95 dB, at a pre-set distance. In another embodiment, output could be visual such the flashing action of four ultra-bright LEDs, of varying colors such as red and two blue, may attract the attention of the user and others around. In yet another embodiment, a vibrating alarm may provide a tactile alert to the user in the highest noise environments.

In embodiments, the device 1508 or instrument 108/110 may execute an application that is programmed to utilize the assignment data, such as user identification and location or other information programmed to the assignment tag, to trigger alarms and/or messages, or filter the triggers. The application may be updated periodically by the server 130, such as to modify variables that will cause a trigger at particular locations or relationships concerning worker variables and alarm triggers. For example, at one particular location, detection of a particular gas may not be cause for alarm, however, at another location where conditions may be different, the same gas at the same detected concentration may be concerning or dangerous. For example, methane detected at a particular level may trigger an alarm and/or message at a location where ignition sources are present but cause no triggers at locations where it is known that no ignition sources are present. In another example, the gas detection instrument may only trigger a high carbon monoxide alarm if the user assigned is above a certain weight.

As discussed herein, data transmitted through the gateway 112 or a device to a remote location may be used in various end applications either by itself or in conjunction with other data, other devices, other information or the like. Any number of applications of the worker safety system may be imagined, a number of exemplary applications will be described herein.

In one example, data from instruments 108, 110 or other nodes may be used for continuous safety inspections. Limits for particular measured variables may be set for individuals and/or groups in respect of automated, real-time, monitoring of safety parameters. The worker safety system may issue warnings when limits are approached to the appropriate audience.

In one example, data from instruments 108, 110 or other nodes may be used for lone worker monitoring. For example, if a lone worker's device triggers an alarm, such as a gas alarm, the connectivity of the instrument to a smart device, such as via an API 114, allows for that alarm to be detected remotely. Remote detection of an alarm may allow a supervisor, for example, to check-in on the lone worker or be able to send help as needed.

In an example, data transmitted to the cloud from instruments 108, 110 may be used for e-permitting. Certain confined spaces cannot be entered without first sampling the environment in the confined space, thus a sampling device may need to be present. Typically, permitting to enter the confined space is done using manual data entry to apply for a permit. The disclosure herein enables the same device that collects data on the environment of the confined space to transmit that data to an electronic permitting application for use in applying for a permit to enter the confined space. In embodiments, the device 118 may be a ruggedized tablet with an integrated gas sensor or with a connection to an instrument 108, 110 that provides gas sensing, wherein the sensed data are automatically provided to auto-fill an onboard application or transmitted to the cloud for use in an application, and in embodiments, is auto-submitted to the relevant permitting authorities.

In an example, data transmitted to the cloud from instruments 108, 110 may be coordinated with third party data. For example, additional hazards may be alarmed through the instruments 108, 110 by overlaying location data derived from the devices 118 or instruments 108, 110 with third party data, such as NOAA data, news/threat/terrorist data, or other external/$3^{rd}$ party data. Such a capability may be especially important for lone workers.

In an example, data transmitted to the cloud from instruments 108, 110 may be used by fire responders and other first responders. In addition to SCBA data, data from environmental monitoring (e.g. gas data), can be delivered automatically to fire responders (or other first responders) to provide site/all-in-one safety. The worker safety system may support automatically configured emergency nodes for first responders. For example, automatic configuration/pairing may occur for emergency responder use in a monitoring group. In embodiments, separate indicators may be used for responder-worn nodes In an example, data transmitted to the cloud from instruments 108, 110 and various safety devices may be used by the worker safety system in the personal monitoring of various physiological and/or behavioral attributes of an individual in order to obtain information relevant to workplace safety, or to alert nearby users regarding a workplace safety situation. Thus, the worker safety system provides a remote and local biometric monitoring interface with nodes in the ad-hoc P2P or mesh network. A user-worn node has an interface to a worker to monitor physiological and/or behavioral attributes. The measured biometric levels are used for remote monitoring and alarms. The goal of such monitoring may be to determine the root causes and acute symptoms of death and injury in the workplace and mitigate the risk of death in the workplace or other major accidents and exposures, such as injury from fires or explosions, exposure to harmful substances or environments, falls, slips, trips, contact with objects and equipment, assaults and violent acts, suicide, terrorism, transportation incidents, overexertion, repetitive motion, and the like. A further goal may be to determine and understand the physiological and behavioral effects of the root causes and acute symptoms of death and injury in the workplace. The worker safety system may be useful in various industries, such as in mines, diesel/fuel plants, refrigeration, fertilizer plants, food & beverage, firefighting, chemical processing & manufacture, HazMat, medical, law enforcement, insurance, and the like.

Illustrative physiological markers may include ECG, heart rate, breathing rate, skin temperature, posture, activity, accelerometry, blood pressure, pulse, body odors, blood alcohol level, glucose levels, oxygen saturation, and the like. Illustrative behavioral markers may include gait, walking patterns, eye movements, motion patterns, noises, removal of the sensor from the person before a prescribed time, and the like.

Physiological and/or behavioral attributes may be measured by sensors, such as sensors integrated with instruments 108, 110, sensors located on the body of an individual, clothing, and/or devices worn or used by the individual. In embodiments, various sensors may be used to measure a person's physiology and behavior, such as one or more of heart rate sensors, blood pressure sensors, gait detection sensors, olfactory sensors, galvanic skin response sensors, proximity sensors, accelerometers, eye tracking sensors, cameras/image sensor, microphones, infrared sensors, gas sensor, capacitive sensor, fingerprint sensor, signal detectors (e.g. WiFi, Bluetooth, mobile phone, etc.), location detectors (e.g. GPS sensor), and the like.

The physiological and/or behavioral attribute information may be used to gain insight into the characteristics of an individual, a department, or a category of employee that may have an effect on the safety and working conditions thereof. For example, the worker safety system may obtain data for an individual to obtain a day-to-day baseline and may compare current information to the baseline information. In another example, the worker safety system may compare an individual's information with a pool of data or with co-workers in a similar situation. The worker safety system may obtain and analyze the physiological and/or behavioral data to determine the physiological state of an individual (e.g., under stress, fatigued, etc.), the causes of accidents in the workplace, or to make predictions about workplace accidents. The worker safety system may utilize sensed data and algorithmic output to provide intervention to the individual or other interested parties (e.g. after two "near misses", a supervisor is alerted and re-training may be scheduled), to block a user from being able to access certain systems (e.g. after detecting a change in gait coupled with a temperature change, a signal is sent to nearby heavy machinery to block access to the individual), to allow a user to access systems (e.g. this individual was blocked because of flu but their temperature is now normal), to suggest behavioral changes to avoid an accident (e.g. after eye tracking indicates fatigue, the user is signaled with a suggestion to take a break), and the like. The collected data may go into a pool of data that can be used for subsequent comparisons.

The worker safety system may use the human body, such as human physiology and human behaviors, as a safety sensor or monitor to detect hazards including various sensors to measure a person's physiology and behavior, and then make use of data from a person or group of people, both physiological and behavioral, of data algorithms to identify a safety issue, and of the data from a person or group of people to prevent accidents or fatalities using certain physiological or behavioral markers. In embodiments, sensors deployed to obtain human physiology and human behaviors may form a body area network.

In embodiments, the use of data from a person or group of people, both physiological and behavioral, may be used to predict an accident, workplace injury, incident, "near miss", etc.; determine if a person is in danger; determine if the environment is hazardous; identify the hazard or family of hazards; make judgments about the safety of a person, group of people or the environment; alert the person, group of people or someone who will intervene via visual, audible, haptic alarms and the like; determine if the person is at risk of a future accident (including the use of near miss data); look for known patterns or to identify new patterns related to personal safety, and the like.

In embodiments, the use of data algorithms may be used in the following ways to identify a safety issue: compare a person against themselves in near time or in historical time; compare the person against the data from a population; compare the data from one person to others working with them at that point in time, and the like.

In embodiments, use of the data from a person or group of people may be used to prevent accidents or fatalities using physiological or behavioral markers. For example, at least one of heart rate, eyelid closures, pupil size, blood pressure, posture, jaw drop, breathing rate, ECG, skin temperature, and sweat may be used as markers to prevent accidents or fatalities in the field of transportation. In another example, at least one of gait, acceleration, blood pressure, heart rate, breathing rate, and posture may be used as markers to prevent accidents or fatalities in the field of contacts with objects or equipment. In another example, at least one of gait, acceleration, blood pressure, heart rate, breathing rate, posture, ECG, sweat, and skin temperature may be used as markers to prevent accidents or fatalities in the field of slips, trips or falls. In another example, at least one of gait, acceleration, blood pressure, heart rate, breathing rate, posture, ECG, sweat, and skin temperature may be used as markers to prevent accidents or fatalities in the field of exposure to harmful substances. In yet another example, at least one of blood pressure, heart rate, breathing rate, posture, ECG, sweat, and skin temperature may be used as markers to prevent accidents or fatalities in the field of assaults or violence. In still another example, at least one of gait, acceleration, blood pressure, heart rate, breathing rate, posture, ECG, sweat, and skin temperature may be used as markers to prevent accidents or fatalities in the field of fires or explosions.

In embodiments, a database of sensor readings may be used to determine the appropriate prediction or identification of the safety issues and the appropriate response. The sensor readings may be wirelessly transmitted to a computer, instrument 108/110, or device 118 and processed in near real time or real time to provide information and insight regarding safety and hazard issues. The database may be consulted for matching sensor readings and matching combinations of sensor readings. Each combination of sensor readings may be associated with one or more particular safety issues and may be associated with one or more particular responses. The safety issue and/or response may be further limited by an additional factor, such as a supervisor or administrator preference, a facility preference, a location, a user, a context, a season, or a business rule. In an aspect, a method of the disclosure may include obtaining sensor data from one or more physiological and behavioral sensors worn by a user 1602, analyzing the sensor data to identify a safety issue 1604, and providing an alert to the user or an interested party regarding the identified safety issue 1608. Analyzing may include matching the sensor data to a known combination of sensor readings in a database of sensor reading combinations. In an embodiment, an application resident on the instrument 108/110 or device 118 may determine a condition hazardous to safety based on the sensor readings and algorithms to determine if the readings are indicating of a root cause or acute symptom of an incident. If a root cause or acute symptom is identified, an alert may be generated and sent through the instrument/device via the wireless network 104 to alert other users and ultimately on to the server 130. In embodiments, the transmitted information may be used to de-authorize the user from an area or equipment, deploy personnel, remotely close off an area, request a check-in on the user, and the like.

In embodiments, when certain physiological markers are combined with certain behavioral markers in a known pattern, a condition may be determined and an alert or response may be elicited. In one example, when a person falls or almost falls, physiological markers of the condition may include the heart speeding up, blood pressure rising, sweating, lungs breathing faster, and the temperature in the extremities may decrease. Behavioral markers of the condition may include a noise being made, a sudden acceleration then a period of not moving, and the like. These markers taken together may form a pattern indicative of a fall or an almost fall.

In another example, when an individual is sleep-deprived, physiological markers of the condition may include increased heart rate, increased blood pressure, and reduced leptin levels. Behavioral markers of the condition may include increased eyelid closure, eyes rolling, and yawning.

Table 1 indicates various incidents and their possible root causes or acute symptoms. When text is present in the cell, it is an indication that there is a correlation between the incident and the possible root cause or acute symptom. In some embodiments, there may be a temporal aspect to the correlation, such as if the root cause or symptom can be measured prior to the incident (Before), after the incident (After), or both (Both). In some instances, a simple correlation (Correlated) is indicated. The cells in Table 1 are blank if no correlation is currently known.

TABLE 1

Root Causes or Acute Symptoms of Incidents

| Root Causes or Acute Symptoms | Transportation | Violence | Contact with Objects/Equipment | Falls, Slips, Trips | Exposure to Harmful Substances/ Environments | Fires and Explosions |
|---|---|---|---|---|---|---|
| Acute Stress | Both | Both | | | | |
| Fatigue | Before | | | | | |
| Under influence (Drugs/Alcohol) | Both | Correlated | | Both | | |
| Distracted | Before | | Correlated | | | |
| Excessive Speed | Before | | | | | |
| Equipment Failure | Correlated | | | | | |
| Weather | Correlated | | | Before | Before | |
| Aggressive | Correlated | | | | | |
| Anger | | Both | | | | |
| Fear | After | | | After | | |
| Awkward Gait | | | | Both | | |
| Injury | | | | Before | | |
| Old age | | | | Both | | |
| Inadequate traction | | | | Before | | |
| Speed of movement | | | | Before | | |
| Light/Dark | Before | | | Before | | |
| Temperature | | | | | Before | Before |

With respect to fatigue, markers including heart rate, blood pressure, eyelid closures (slow closures, frequency of closures), pupil size, head position, and jaw drop, as well as other cardiovascular disturbances and sympathetic activity may be used to identify the condition.

With respect to stress, markers including heart rate (e.g. increased heart rate), sweat, dilated pupils, shallow breathing, increased blood pressure, changes in a person's voice (pitch, rate, volume), odor and tightened scalp may be used to identify the condition.

With respect to being under the influence, markers including breathing rate, increased blood pressure, increased heart rate, gait and speech changes may be used to identify the condition.

With respect to anger, markers including jaw clenching/ teeth grinding, headache, stomachache, increased blood pressure, increased breathing rate, increased heart rate, sweating (especially hands), feeling hot in the neck/face, shaking/trembling, and dizziness may be used to identify the condition.

With respect to slips, trips, and falls, markers including breathing rate, blood pressure, heart rate, and awkward gait may be used to predict or identify a slip, trip, or fall. For example, the pattern for fear of heights, which is an indicator of potential falls, may be heart rate increase, stress temperature decrease, and systolic BP increase. However, if the situation includes an activity, such as climbing a ladder which might increase the heart rate independently, then adding a gait measurement may be necessary to determine if the individual is in motion or not.

With respect to carbon monoxide exposure, markers including nausea, vomiting, restlessness, euphoria, fast heart rate, low blood pressure, cardiac arrhythmia, delirium hallucinations, dizziness, unsteady gait/stumbling, confusion, seizures, central nervous system depression, unconsciousness, respiratory rate changes, and respiratory arrest may be used to identify the condition.

TABLE 2

Physiological Markers of Root Causes or symptoms.

Part 1.

| Root Causes or Acute Symptoms | Heart Rate | Blood Pressure | Sweat | Breathing Rate | Gait | Pupil Size Change | Shaking/ Trembling | Dizzy |
|---|---|---|---|---|---|---|---|---|
| Acute Stress | X | X | X | X | | X | X | X |
| Fatigue | X | X | | X | | X | | X |
| Under influence (Drugs/Alcohol) | X | X | X | X | X | X | | X |
| Distracted | | | | | | | | |
| Excessive Speed | | | | | | | | |
| Equipment Failure | | | | | | | | |
| Weather | | X | X | | | | X | X |
| Aggressive | | | | | | | | |
| Anger | X | X | X | X | | | X | X |

TABLE 2-continued

Physiological Markers of Root Causes or symptoms.

Part 1.

| | | | | | | | | |
|---|---|---|---|---|---|---|---|---|
| Fear | X | X | X | X | | X | | |
| Awkward Gait | | | | X | | X | | X |
| Injury | | | | | | X | | |
| Old age | | | | | | X | | |
| Inadequate traction | | | | | | X | | |
| Speed of movement | | | | | | X | | |

Part 2.

| Root Causes or Acute Symptoms | Stomach ache | Head ache | Hot/flushed face & neck | Body Temp | O2 Level | Odor | Eye Blinks | Head position, facial changes, jaw drop | Voice changes |
|---|---|---|---|---|---|---|---|---|---|
| Acute Stress | | | | | | X | | | |
| Fatigue | | | | X | X | | X | X | X |
| Under influence (Drugs/Alcohol) | | | | X | X | | | | X |
| Distracted | | | | | | | | | |
| Excessive Speed | | | | | | | | | |
| Equipment Failure | | | | | | | | | |
| Weather | X | X | X | | | | | | |
| Aggressive Anger | X | X | X | | | | | | |
| Fear | | | | X | | X | | | |
| Awkward Gait | | | | | | | | | |
| Injury | | | | | | | | | |
| Old age | | | | | | | | | |
| Inadequate traction | | | | | | | | | |
| Speed of movement | | | | | | | | | |

In embodiments, the systems and methods for monitoring physiology and behavior to identify or predict safety issues and mitigate risk may be embodied in a wearable device. In embodiments, the wearable device may include multiple physiological or behavioral sensors, such as those described herein. In embodiments, the wearable device may be a garment with one or more embedded sensors, a watch, a portable device, a badge, eyewear, a ring, and the like. The wearable device may include a wireless transmitter to transmit data in the manners described herein and ultimately to a server for analysis. The device may include a display to present content from a server based on analyzed data. The content may be information or an alert. The garment may be a vest, hardhat, jumpsuit, belt, band, and the like.

In embodiments, simulation software may be built on data models developed after a period of data collection on personal monitoring. The simulation software may have input variables, such as behavioral, mechanical, environmental, and physical, and risks may be identified. In one example, the input variable may be a piece of personal protective equipment and a simulated work environment and risk factors may be identified.

In embodiments, software application resident on a device, such as an instrument 108, 110, safety device, mobile device, or the like, may overlay safety concerns on a real time view of the surrounding environment using augmented reality. Safety concerns can be pre-identified or can also be identified in real time.

In an embodiment, certain behaviors may be rewards and incentives offered to workers who do the right thing safety/compliance-wise based on analysis of collected data. For example, if the data collection indicates that the worker fell and then checked in to the nurses' office within a set period of time, they may be rewarded with a meal voucher or the like. Rewards may be given for other compliant behavior, such as checking an instrument back in to a tool crib, tagging instrument data with a location-based NFC tag, wearing PPE correctly, checking in with another worker, and the like.

Commercially available wearable devices useful in the disclosed systems and methods include devices such as the Zephyr BioHarness™, Aframe Digital MobileCare Monitor, BodyMedia FIT, Nonin, Valencell Performtek, Gaitometer, Wahoo Strap Monitor, Stress Thermometer, and others.

Continuing with another example of an application of the worker safety system, an application, which may be executing on instruments 108/110, devices 118, the server 130 or on a third party device, may prepare a dynamic map view of node location in the ad-hoc P2P or mesh network to monitor and display one or more node locations. The map may display relative location without reference to an area map, absolute location with reference to an area map, or 3D location on a topographic map or tunnel system. The map view may present alarm locations. In embodiments, a plurality of instruments 108/110, which may be enabled to communicate in the wireless network 104 or may be NFC-enabled, may transmit data (e.g., sensed data, assignment data, location data, calibration status, etc.) to the server 130, at least partially transmitted by the wireless network 104, wherein the data may be further displayed in the map view.

Continuing with another example of an application of the worker safety system, real-time information signage may be used in conjunction with data collected from instruments 108, 110. For example, a real-time sign may be in electronic communication with one or more instruments 108/110, devices 118, the server 130 or a third party device such as by WiFi, Bluetooth, RFID or the like The real-time sign may be located in an area and may display data based on an alarm from a nearby instrument 108, 110 and may serve as a remote alarm. The data may be transmitted directly to the sign using the wireless network 104 or may be transmitted to the cloud where it is processed to determine if it should be displayed on the real-time information sign. In embodiments, a plurality of instruments 108/110, which may be enabled to communicate in the wireless network 104 or may be NFC-enabled, may transmit data (e.g., sensed data, assignment data, location data, calibration status, etc.) to the server 130, at least partially by the wireless network 104, wherein the data may be displayed by the real-time sign.

In another example of an application of the worker safety system, data collected from instruments 108, 110, such as noise dosimeters, may be used to alarm workers. For example, if a gas detector tripped a detection threshold but a noise dosimeter indicated noise above a certain decibel range, the gas detector instrument will be signaled to relay its alarm via haptic and illuminated messaging as well as an audible alarm. Further, the alarm message may also be displayed on a nearby real-time informational sign.

In another example of an application of the worker safety system, data collected from instruments 108, 110 may determine an amount of oxygen in the environment. Under certain oxygen concentration conditions, a catalytic bead sensor may not work so the instrument may provide a warning. A remotely located supervisor may be alerted to the situation and deploy additional resources, such as personnel or different sensors, to the area to ensure safe and accurate monitoring.

In another example of an application of the worker safety system, data collected from instruments 108, 110 may be used in combination to trigger various levels of alert/alarm. For example, if an instrument reads a high carbon monoxide level, an alarm may be sounded but it may only be sounded at the instrument that made the reading. If an instrument's accelerometer determines that a man is down, an alarm may be sounded on the instrument as well as a few nearby instruments as determined by presence in the same wireless network 104 or proximity (e.g. GPS location, same NFC check-in to a location, manually identified location). If an instrument determines that both carbon monoxide is high and a man down is down, a critical alarm may be sounded on the instrument, to nearby workers, and in a wide area.

In yet another example of an application of the worker safety system, the system may be used for leak detection/pipeline monitoring. For example, sensors for pipeline leak inspections for safety and compliance monitoring, such as vehicle- or drone-mounted gas detectors, thermal conductivity or IR sensors, optical sensors, underground sensors, gas utility instruments and the like used to detect leaks may transmit data to the cloud or other remote location directly or through a device 118 or gateway 131, 112. In this example, the drone may be operated remotely in a two-way fashion so that control can be done locally or, for example, if the area needs to be evacuated, control can be remote. Applications may use the data to remotely configure the sensors and maintain the status of the sensors.

In still another example of an application of the worker safety system, the system may obtain data from eye wash stations, chemical showers, first aid stations, AED/defibrillator, fire extinguishers, sorbent stations or other fixed assets 124. In one example of an eye wash station or chemical shower, sensors may be placed at the station/drain to detect hazards/toxins that are being washed off a user, wherein the sensors may communicate data back to the cloud or remote location by any communication method described herein, either directly or through a device 118 or gateway 131, 112. In embodiments, the sensors may be stand-alone sensors with remote communications capability or may have local communications capability at a nearby dock or instrument that further transmits the data. In any event, such information may be used in an application used by first responders to determine what equipment/personnel to deploy. The data may be combined with other data being collected by the worker safety system that may be localized to the same area through the use of a shared assignment (e.g. NFC tags) or a known location (e.g. GPS or known fixed asset 124 fixed location). Continuing with this example, the drain sensor may determine particular toxins and a sensor in a smoke detector may indicate an identity of particulates in the air from a fire, in addition to temperature and visibility data. Images may also be captured from a nearby camera. These data combined together may alert a first responder that not only is there a fire, but it is a chemical fire and what the specific chemical it is that has caused the fire. Second responders may also be alerted as to what the specific cleanup needs will be. Thus, without any on-site personnel calling an emergency number and explaining the situation, first and second responders may have unprecedented situational awareness.

Continuing with this example, secondary alarms may be generated from an eyewash/shower pull. An inventory of items in the area may be needed in order to generate the secondary alarms, wherein the inventory is known at the remote location so that it gets displayed to first and second responders upon the eyewash/shower pull or the inventory is gathered by a nearby instrument and transmitted remotely. The inventory may include information such as strong acid present, tank of phosphine present, gases present, chemicals present, combination of gases and chemicals present, or any information that would be on a posted hazard placard.

Continuing with the example of fixed assets 124 contributing to the worker safety system, a nearby sensor or integrated sensor may be able to transmit data regarding the kind of fire extinguisher that was used during a fire, such as a water, foam, dry powder, carbon dioxide, ABC, wet chemical, metal, and the like, or what kind of sorbent was utilized for a spill. Such information may be useful to a first or second responder in determining equipment and personnel to deploy.

Continuing with the example of fixed assets 124 contributing to the worker safety system, a sensor in area that sense an acid spill or other like hazard may transmit data back to a remote location for processing. Depending on the kind of hazard detected, instructions or information may be transmitted to devices in the area, displayed on a real-time information signage, transmitted to responders, and the like. For example, directions to the nearest eyewash/shower may be transmitted to instruments or real-time signage in the area upon sensing an acid spill or other hazard. If there are multiple hazards, the instructions may be specific as to which station to go to if one or more have not been maintained or are already in use, which would be known from sensed data at that location. Nearby instruments may also be informed of the hazard, of the activation of a nearby eyewash/shower station, or asked to check in with the user of a nearby instrument or warned to stay away from an area. When a first worker is asked to check in with a second worker, they may receive reminders of the request until the worker safety system detects that the workers are near each other or if some other proof of contact has been transmitted. For example, a voice print from the second worker or an image of the second worker may be recorded with the instrument or device of the first worker doing the checking.

Continuing with the example of fixed assets 124 contributing to the worker safety system, integrated sensors with an eyewash station or shower may be used to automate and accelerate periodic testing of flow rate, total volume, water temperature, salinity, pH, and the like, in respect of safety inspections, compliance with local or federal requirements, and to predict the need for maintenance. With the integrated sensors in communication with the worker safety system, automated maintenance reminders may be delivered, automated records may be created of testing results and technicians performing tests, automated certificates of compliance may be generated, performance statistics may be gathered, and the like.

In embodiments, one component of the worker safety system is to perform a job hazard analysis (JHA) and then apply the hierarchy of hazard controls. The specific job is analyzed to understand various safety-related aspects, such as an identification of tasks, an identification of potential hazards (e.g. gas, electrical, chemical, thermal, noise, etc.), and the like. The worker safety system may have the information about various tasks and known potential hazards and pay perform an analysis to determine if the hazard can be eliminated from the task. If not, the worker safety system may recommend a way to mitigate the hazard. For example, certain controls may be used to minimize hazards, such as engineering/mechanical controls. Altered behavior such as through training, real-time signage as discussed herein, instructional messages, and the like may be used to minimize hazards. Administration (e.g. scheduling) may also be useful in minimizing hazards.

In embodiments, the worker safety system may determine, based on the identified hazard and task, an appropriate PPE or other protective technology (e.g. foam protection, hearing protection, fall, etc.) to use to minimize a hazard. The worker safety system, through use of connected instruments and devices may determine if the correct subtype of PPE was ultimately selected by the worker, if the selected PPE has been maintained, if the selected PPE has been donned or is otherwise in use, if the selected PPE is being used properly, and the like. For example, a job may require use of an air purifying respirator that filters in a chemical or mechanical way to block dust, fumes or gases. The worker safety system may recommend a disposable versus a re-usable/refillable respirator based on the task, the worker safety system may determine if the re-usable respirator has been properly maintained, and based on a pressure reading from the respirator, the worker safety system may determine that the respirator is in proper use. Further, the air purifying respirator may be equipped with a sensor, such as an RFID. If the worker safety system detects that a worker is in an area requiring the PPE or has indicated that a task has begun requiring the PPE but the RFID is not detected by the worker's instrument, an alarm may sound.

In another example, the worker safety system may determine, based on the identified hazard and task, that a self-contained breathing apparatus is required (SCBA). Sensors on the supplied air tank may be used to determine quality, efficacy (e.g. filter-mounted sensor), pressure (e.g. hose- or mouthpiece-mounted sensor), operational status, and the like. The sensors may communicate with beacons, devices, instruments, gateways or directly to the cloud or other remote location. Based on the sensor readings, the worker safety system can anticipate or predict maintenance based on usage and operational status instead of on a schedule. The worker safety system can store pressure test results for annual certification. The worker safety system can help set up a replacement tank, if necessary.

In an embodiment, the worker safety system may determine, based on the identified hazard and task, that fall protection is required, such as a harness, a self-retracting lifeline, rails/guards, retrieval equipment, and the like. A sensor attached to a worker or integrated in an instrument that is with the user may be used to determine if the worker is in the air. Further, knowing that data, the worker safety system can determine if the appropriate fall protection equipment has been checked out by the worker, if that fall protection has been maintained if they do have it on, if the protective equipment is being worn, and if they are using it correctly.

Various gas monitors that may be used in the worker safety system may include gas sensors (e.g. IR, (LED), LEL, catalytic bead, electrochemical, redundant gas sensors), humidity sensor, temperature sensor (e.g. to determine heat stress), a wind sensor, a microphone, an accelerometer (e.g. to measure lack of motion in order to further determine man-down, acceleration/deceleration to determine a fall), particulate sensor, a barometer, biometric sensors, phase, time of flight, signal strength, GPS or other location-sensing technology, a panic button (e.g. to sound a loud alarm, to transmit a signal remotely), NFC, Bluetooth, radio module, WiFi, integrated cellular technology, and the like.

In one mode, alarms may be triggered based on set thresholds, such as detection of one or more particular gases or detection of a threshold amount of gas. In another mode, the gas detection instrument may include a dedicated panic button. For example, an alarm may be sounded when the panic button is pressed and held for 3 seconds. This may allow the user to alert others at the press of a button in the event of distress. In another mode, the gas detection instrument may be programmed with a man down alarm. For example, if the instrument does not detect motion via a built-in accelerometer for a predetermined number of seconds, an alarm may be triggered and teammates may be alerted. In yet another mode, alarms may provide an early warning below a low alarm set point. For example, when a gas concentration exceeds an Acknowledgeable Gas Alert set point, the instrument may activate the alarm indicators to alert the user that she may be approaching a dangerous condition. The user may need to take preliminary or mitigating action, but can acknowledge and silence the alert while she continues her work. If the condition persists beyond 30 minutes, the alert may be reactivated.

The portable environmental sensing device or gas detection instrument may include a rugged case design, featuring field replaceable external dust filters to prevent clogs, plastic edges to prevent overmold peeling, plastic rails to reduce overmold tearing, a plastic ridge to protect external sensor filters when facedown, and a recessed display to protect from scratches.

Gas monitors useful in the worker safety system may be portable, free-standing, fixed, battery-powered, wall-mounted with fixed line power, modular, and the like. In embodiments, each form factor may enable different functions or capabilities of the gas monitor. In embodiments, a modular gas monitor may take the form of a central sensing unit that can engage with various form factors. For example, the modular gas monitor may be able to engage with a free-standing base, a slot in a wall to engage with line power, a robotic unit, a piece of heavy equipment such as a bulldozer, crane, etc., and the like.

In engaging with a free-standing base, the central sensing unit may be disposed in the base in a downward facing manner which protects it from the environment and allows substantially 360 degree access to environment. The free standing base may have a speaker to sound alarms in an area. The speaker may be a piezo-based speaker that may be electronically designed for intrinsic safety. The central sensing unit may be designed with bumps or other engagement features on the surface of the modules to prevent them from sliding out of the base. The receiving portion of the base may be designed to interact with the engagement features.

In embodiments, the central sensing unit may emit a loud sound during calibration and during setup (e.g. 108 dB). There may not be an electronic way to control the sound by operation or by regulation. An accessory component may be provided for placement over the audio output to dampen the sound. The geometric shapes inside the accessory component may provide additional surface area to absorb the sound.

In embodiments, monitors useful in the worker safety system may be area monitors, such as perimeter monitor (e.g. at the edge of refinery), dust/particulates monitoring, noise/sound level, gases/fugitive emissions, chemicals/toxins, fence line monitoring (e.g. cordon off an area), and the like. In an embodiment, mere placement of the area monitors and establishment of a peer network, as described herein, may cause the auto-establishment of fence lines and perimeters.

While area monitors 110 themselves may sense an environmental parameter that may trigger an alarm, sending of a communication, controlling another device or system, and the like, area monitors 110 may receive a report from a device 108, such as through the wireless network 104, and sound an alarm that may be audible widely. Area monitors 110 may receive a report from a device 108 or other network node, such as through the wireless network 104, and send out a communication to other devices 108 and monitors 110. Area monitors 110 may receive a report from a device 108, such as through the wireless network 104, and control another device or system in response to the report.

Turning now to describing particular instruments that may be used in the worker safety system, one such instrument is a portable electrochemical gas sensing apparatus 108, or badge reader.

Toxic and combustible gas sensing instruments are important devices for many industrial and other applications, such as for safety, environmental and emissions monitoring, quality and process control, clinical diagnostic applications, and the like. In general, such instruments are portable and include sensors that are sensitive and accurate.

An instrument with an electrochemical sensor may be used to measure the concentration of a specific gas. The basic components of an electrochemical sensor include a working (sensing) electrode, a counter electrode, and optionally a reference electrode. These electrodes are typically enclosed in a housing and are in contact with a liquid or solid electrolyte. The working electrode is typically on the inner face of a membrane, such as Teflon, which is porous to gas, but impermeable to the electrolyte.

The gas to be detected diffuses into the sensor and through the membrane to the working electrode and electrolyte. The electrolyte may be an aqueous solution of an acid, an alkali, an ionic liquid, or a mineral salt; examples are sulfuric acid, phosphoric acid, potassium hydroxide, lithium chloride, and lithium perchlorate. The electrolyte may also be of an organic type such as tetraethyl ammonium perchlorate (TEAP) in a low vapor pressure organic solvent. When the gas reaches the working electrode and electrolyte, an electrochemical reaction occurs; either an oxidation or reduction depending on the type of gas. For example, carbon monoxide may be oxidized to carbon dioxide, or oxygen may be reduced to water. An oxidation reaction results in the flow of electrons from the working electrode to the counter electrode through an electronic circuit, such as a potentiostat circuit, and conversely a reduction reaction results in flow of electrons from the counter electrode to the working electrode through the electronic circuit. This flow of electrons constitutes an electric current, which is proportional to the gas concentration. The potentiostat circuit may be a part of an electronic processing unit in the instrument, which detects and amplifies the current and scales the output according to the calibration. The instrument may then display the gas concentration in, for example, parts per million (PPM) for toxic gas sensors or percent volume for oxygen sensors. Because the volume of the electrolyte can change with time and with environmental conditions, a reservoir chamber is usually incorporated into the sensor to provide additional amounts of electrolyte and/or to allow for expansion of the electrolyte in certain environments.

An LEL (lower explosive limit) sensing instrument detects that one or more combustible gases are in the atmosphere. For flammable substances, there is a limit concentration of gas necessary for ignition. Below this limit, a mixture of the substance in air cannot be ignited. This limit is called the LEL. One type of LEL sensor is a catalytic bead sensor, which is designed to protect against the combustion of gases in the atmosphere, rather than specifically detect a single combustible gas. The LEL of a substance is established by standardized methods, and typically lies between 0.5 and 15% by volume. A catalytic bead sensor may include two measuring beads (called pellistors), each made of porous ceramic material embedding a small platinum wire coil. The active (sensing) bead contains catalytic material, while the other one is a reference bead and does not contain catalytic material. The beads may be matched and built into a balanced, resistive circuit, such as a Wheatstone bridge. When a combustible gas comes in contact with the sensor, the active bead begins to burn the gas causing it to increase in temperature, with a resulting increase in the bead's resistance that is proportional to the gas concentration. The reference bead does not react to the combustible gas so its temperature and resistance does not increase. The imbalance in the circuit is then converted into a gas reading. Once calibrated with a particular gas, an LEL sensor will display values assuming all gases in the environment are that one particular gas. If a sensor calibrated to methane detects another gas, the instrument will display LEL values assuming it is truly methane. Correlation factors are therefore used to translate a reading from the units of the calibration gas to the units of a second gas.

A catalytic bead sensor instrument may also include a processing unit. The processing unit and sensor are typically enclosed within a rigid casing or housing.

Figure 17:
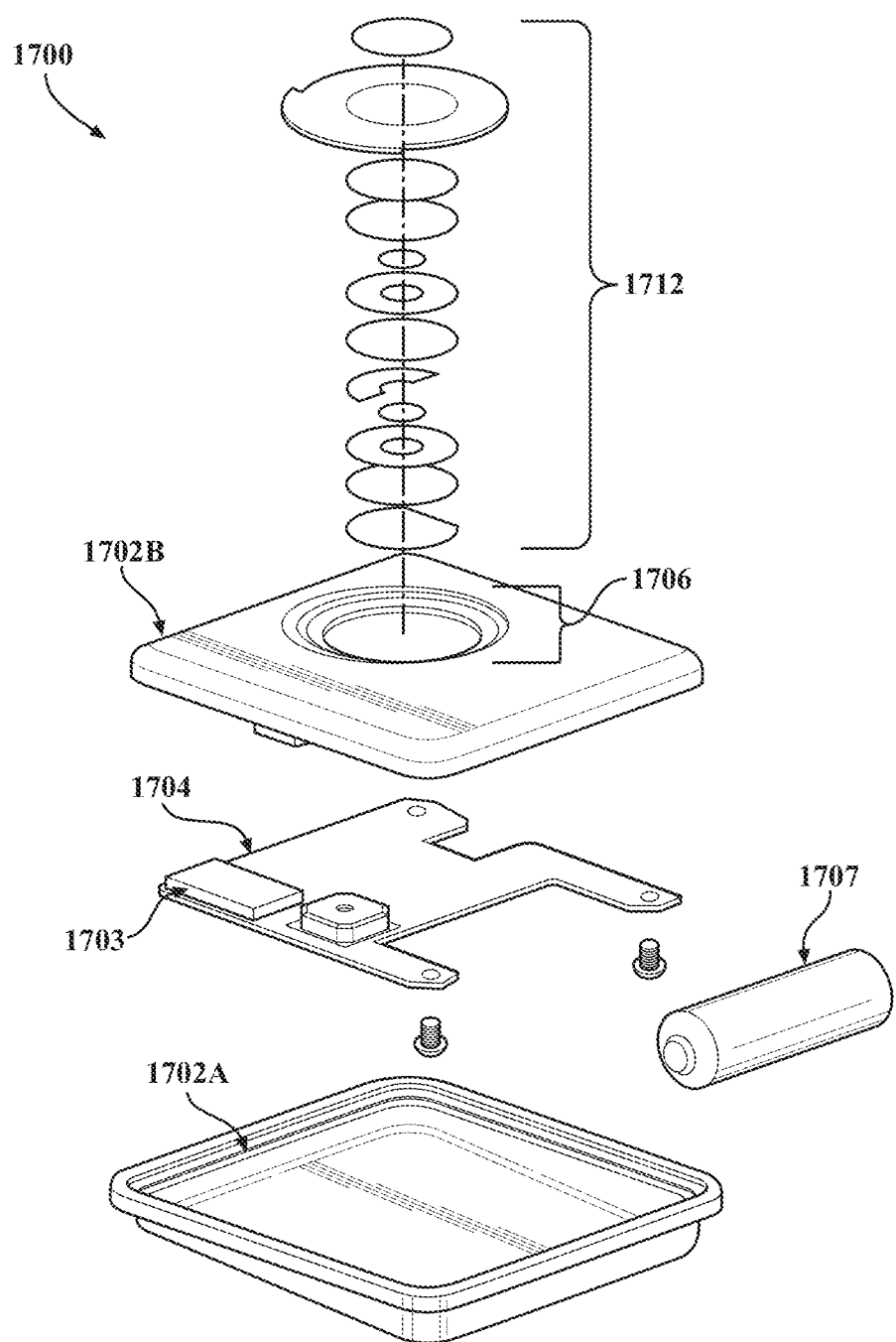
FIG. 17 is an exploded view of various components of an exemplary gas sensing apparatus.
Figure 18:
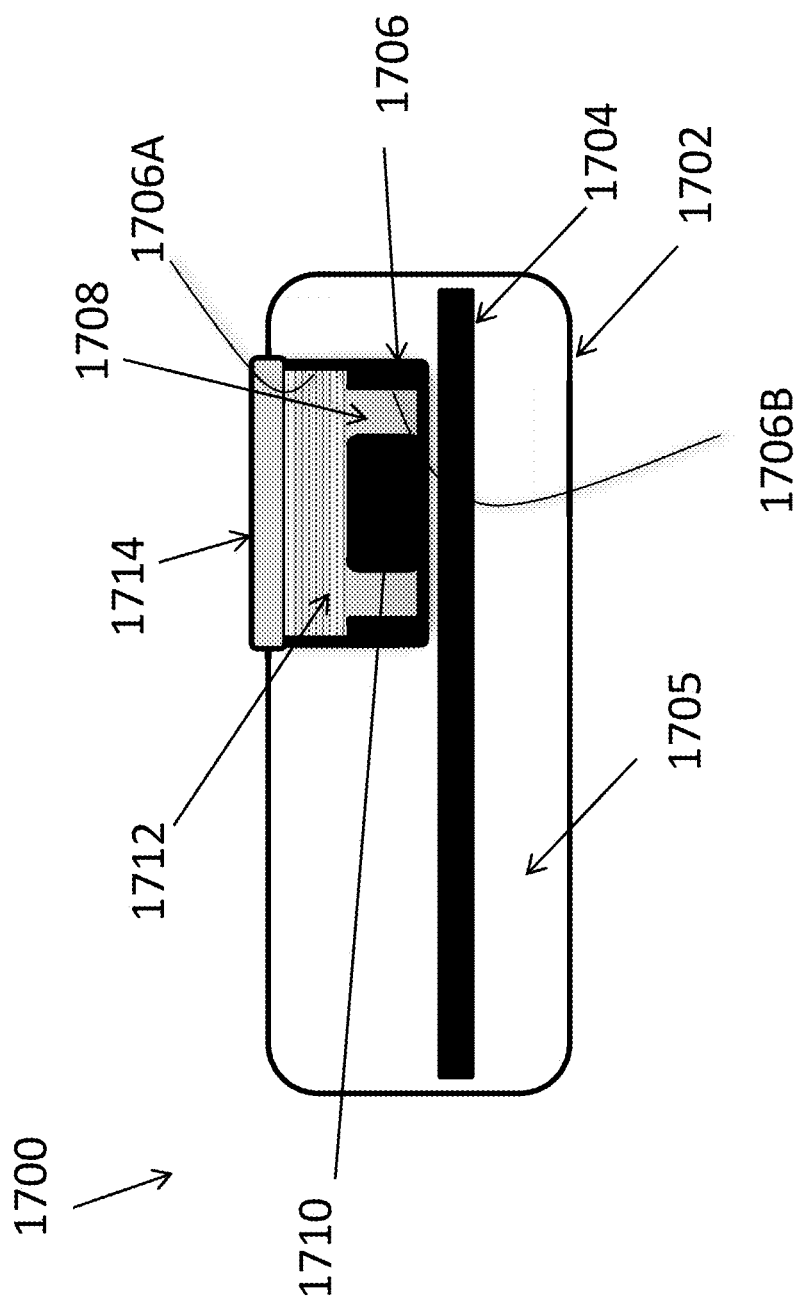
FIG. 18 is a cross-sectional view of an exemplary electrochemical gas sensing apparatus.
Figure 19:
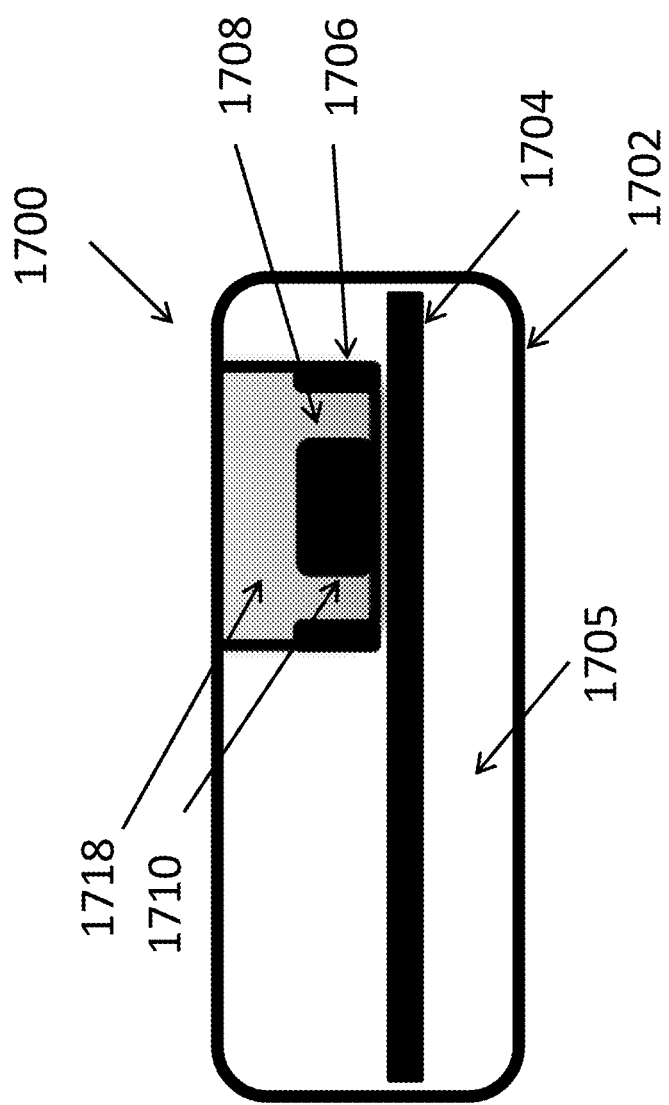
FIG. 19 depicts the electrochemical sensing apparatus of FIG. 18 without an electrode stack.

FIGS. 17-19 illustrate an exemplary gas sensing apparatus 1700 with a housing 1702 and an electrochemical sensor embedded in the housing 1702, and which is configured to detect one or more gases such as oxygen, carbon monoxide, methane, and hydrogen sulfide, along with others. In particular, housing 1702 may comprise one or more portions 1702A, 1702B that may be formed by molded plastic or the like. When the apparatus 1700 is assembled, the housing may be sealed. As shown, a depression 1706 is formed on an exterior surface of the housing 1702A, with a centrally disposed raised platform 1710 (shown in FIGS. 18 and 19) in the depression 1706 formed on the exterior surface of the housing. Depression 1706 is integral with portion 1702B and, in embodiments, results from the molding process giving rise to portion 1702B. The depression comprises perimeter sidewalls defining the boundary of the depression. In embodiments where the depression 1706 is circular, the depression comprises a circumferential perimeter side wall 1706A, 1706B (FIG. 18). The perimeter sidewall has two portions 1706A, 1706B in FIG. 18, as FIG. 18 is depicting an embodiment with a stepped-out upper portion.

The raised platform 1710 may support an electrode stack 1712 of the electrochemical sensor within the depression 1706. The depression 1706 also forms a second reservoir 1708 (bounded by the outer diameter or perimeter of the raised platform and the bottom portion of the perimeter side wall 1706B in the embodiment shown in FIG. 18) for electrolyte of the electrochemical sensor. As best seen in FIG. 17, the depression 1706 my be cylindrical in shape to support a generally cylindrical sensor, although other shapes may also be used to accommodate sensors of various shapes. The sensor may include the electrode stack 1712 as well as the electrolyte solution in the second reservoir 1708.

As seen in FIGS. 18 and 19, the depression 1706 may include a first reservoir 1718 and a second reservoir 1708, which may aid in support of the electrode stack 1712. The second reservoir is adapted to hold an electrolyte solution that is in fluid communication with the electrode stack 1712. A sensor top cap 1714 is sized to fit over the depression 1706, where the cap may include a capillary hole that provides access for gas to enter into the electrode stack 1712.

The electrode stack 1712 may include at least one measuring electrode, at least one counter electrode, and optionally, at least one reference electrode, along with a gas permeable membrane for allowing gas to flow to the measuring electrode. The stack 1712 may include one or more electrolyte absorption pads between the electrodes to ensure that the electrolyte remains in contact with the electrodes. The electrode stack 1712 may also include various other components, such as separators for the electrodes. For example, an exemplary electrode stack is shown and described in U.S. Pat. No. 8,771,490.

Housing 1702 defines an interior space 1705. Depression 1706 extends into interior space 1705, 2005 but is separated therefrom by the interior-space facing surface of the sidewall and interior-space facing surface base. A printed circuit board assembly 1704 may be disposed in the interior space 1705, along with a battery 1707 or other power source for providing power to circuitry of the apparatus 1700. For example, the assembly 1704 may include circuitry such as a processing unit 1703 with a potentiostat circuit in order to convert signals from the sensor into a gas concentration reading or other parameter related to gas concentration exposure. Although not specifically shown, the electrode stack 1712 may be in electrical communication with processing unit 1703, such as being connected via wires. In embodiments, the gas sensing apparatus 1700 does not have a user display for display of gas concentration readings. Instead, the gas sensing apparatus 1700 may include an interface to enable communication of such readings to an external device, via Bluetooth protocol or the like, such as to an application on a mobile phone or other computing device.

The electrode stack 1712 may be in electrical communication with an alarm, such as an audible alarm, a visual alarm, a vibrating alarm or the like, wherein the alarm may be located in the interior space of the housing, or may be wirelessly connected to the processing unit 1703. An alarm modality may be automatically triggered, such as through detection of one or more particular gases, detection of a threshold amount of gas, or the like. An alarm or message may be provided when determinations are made regarding various detected conditions, such as gas present (alert, low alarm, and high alarm), STEL (short-term exposure limit) reached, and TWA (time-weighted average) above a threshold. In embodiments, an alarm modality may feature audible, visual, and/or vibrating alarm indicators that may be used in multiple modes. For example, an audible indicator may be capable of delivering a 95 dB tone at a distance of 10 centimeters. In another example, the flashing action of four ultra-bright LEDs, two red and two blue, may attract the attention of the user and others nearby. In yet another example, a vibrating alarm may provide a sensory alert to a user in a high noise environment.

Figure 20:
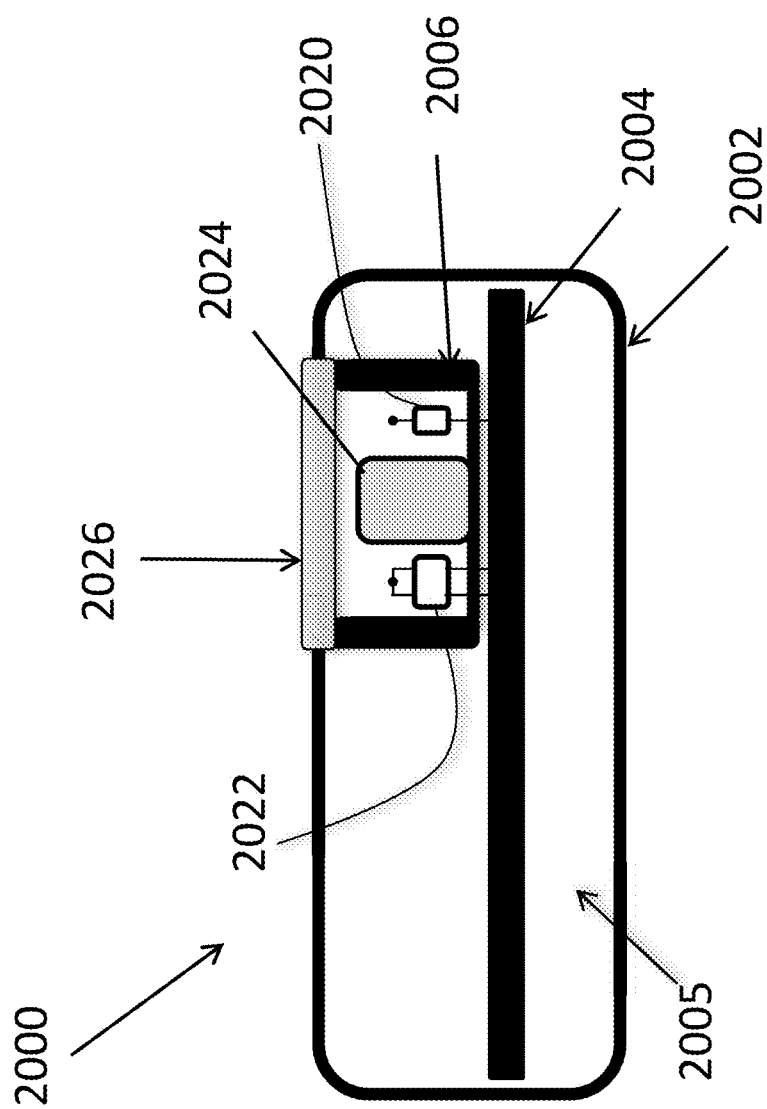
FIG. 20 illustrates a cross-sectional view of an exemplary combustible lower explosive limit sensing apparatus.

FIG. 20 illustrates an exemplary portable combustible lower explosive limit (LEL) gas sensing apparatus 2000 with a housing 2002 and a combustible LEL sensor formed within the housing 2002. In particular, housing 2002 may comprise one or more portions that are assembled together. When the apparatus 2000 is assembled, the housing may be sealed. As shown, a sensor depression 2006 is formed on an exterior surface of the housing 2002, with a chamber separator 2024 integrally formed in the exterior surface to separate an active sensing bead 2022 in one chamber and a reference sensing bead 2020 in another chamber of the depression 2006. Depression 2006 is integral with housing 2002 and, in embodiments, results from the molding process giving rise to housing 2002. Similar to the embodiments shown in connection with FIGS. 17-19, the depression comprises perimeter sidewalls defining the boundary of the depression. In embodiments where the depression is circular, the depression comprises a circumferential perimeter side wall.

The depression 2006 may be cylindrical in shape. A sensor flame arrestor 2026 may be sized to fit over the depression 2006.

An exemplary combustible gas sensor that may be integrated with housing 2002 may include a gas sensing element including an electric heating element, a first layer coated on the electric heating element and comprising a precious metal catalyst supported on a porous oxide, the precious metal catalyst catalyzing combustion of a combustible gas to be detected by the sensing element, and a second layer overlaying the first layer, and comprising a catalytic compound capable of trapping gases which poison the precious metal catalyst. The sensor may also include a compensating element comprising an electric heating element lacking a catalyst. The sensing element and the compensating element may be connected to a processing unit, not shown, that may be constructed and arranged to detect changes in resistance of the sensing element and compensating element and to provide a reading of the changes. For example, an exemplary LEL sensor with gas sensing element and compensating element is shown and described in U.S. Pat. No. 7,007,542. Appropriate catalytic materials for the first and second layers may include one or more of oxide-supported metal oxides supported on porous oxide supports; solid acids, preferably solid superacids; solid bases, preferable solid superbases; and metal-loaded zeolites and clays.

Housing 2002 defines an interior space 2005. Similar to the embodiments shown in FIGS. 17-19, depression 2006 extends into interior space 2005 but is separated therefrom by the interior-space facing surface of the sidewall and base. A printed circuit board (PCB) assembly 2004 may be disposed in the interior space 2005, along with a battery (not shown) for providing power to circuitry of the apparatus 2000, and containing a processing unit. For example, circuitry may include the processing unit, such as with a Wheatstone bridge circuit in order to convert signals from the sensor into an LEL sensor reading or other parameter related to potential gas explosion. Each of the beads may be in electrical communication with the processing unit, such as being connected via wires. In embodiments, the gas sensing apparatus 2000 does not have a user display for display of gas concentration readings. Instead, the gas sensing apparatus 2000 may include an interface to enable communication of such readings to an external device, via Bluetooth protocol or the like, such as to an application on a mobile phone or other computing device.

The sensor may be in electrical communication with an alarm, such as an audible alarm, a visual alarm, a vibrating alarm or the like, wherein the alarm may be located in the interior space of the housing, or may be wirelessly connected to the processing unit. An alarm modality may be automatically triggered according to detection of various conditions. In embodiments, an alarm modality may feature audible, visual, and/or vibrating alarm indicators that may be used in multiple modes. For example, an audible indicator may be capable of delivering a 95 dB tone at a distance of 10 centimeters. In another example, the flashing action of four ultra-bright LEDs, two red and two blue, may attract the attention of the user and others nearby. In yet another example, a vibrating alarm may provide a sensory alert to a user in a high noise environment.

The gas sensing apparatus 1700 or 2000 with housing 1702 forming part of the sensor and its construction provides several advantages, in that the overall packaging size is reduced, the component count is reduced, and potential failure modes are reduced, as compared to prior gas sensing instruments. In embodiments, the apparatus 1700 or 2000 may not need a user display, in that communication such as Bluetooth may provide display capability to an external device. A battery for the apparatus may have a year or more of battery life. The manufacturing costs for the device may be reduced such that the apparatus may be customer disposable.

Other gas monitors may include gas sensors (e.g. IR, (LED), LEL, catalytic bead, electrochemical, redundant gas sensors), humidity sensor, temperature sensor (e.g. to determine heat stress), a wind sensor, a microphone, an accelerometer (e.g. to measure lack of motion in order to further determine man-down, acceleration/deceleration to determine a fall), particulate sensor, a barometer, biometric sensors, phase, time of flight, signal strength, GPS or other location-sensing technology, a panic button (e.g. to sound a loud alarm, to transmit a signal remotely), NFC, Bluetooth, radio module, WiFi, integrated cellular technology, and the like.

Gas monitors useful in the worker safety system may be portable, free-standing, fixed, battery-powered, wall-mounted with fixed line power, modular, and the like. In embodiments, each form factor may enable different functions or capabilities of the gas monitor. In embodiments, a modular gas monitor may take the form of a central sensing unit that can engage with various form factors. For example, the modular gas monitor may be able to engage with a free-standing base, a slot in a wall to engage with line power, a robotic unit, a piece of heavy equipment such as a bulldozer, crane, etc., and the like.

In engaging with a free-standing base, the central sensing unit may be disposed in the base in a downward facing manner which protects it from the environment and allows substantially 360 degree access to environment. The free standing base may have a speaker to sound alarms in an area. The speaker may be a piezo-based speaker that may be electronically designed for intrinsic safety. The central sensing unit may be designed with bumps or other engagement features on the surface of the modules to prevent them from sliding out of the base. The receiving portion of the base may be designed to interact with the engagement features.

In embodiments, the central sensing unit may emit a loud sound during calibration and during setup (e.g. 108 db). Regulatorily and operationally, there may not be an electronic way to control the sound. An accessory component may be provided for placement over the audio output to dampen the sound. The geometric shapes inside the accessory component may provide additional surface area to absorb the sound.

In embodiments, monitors useful in the worker safety system may be area monitors, such as perimeter monitor (e.g. at the edge of refinery), dust/particulates monitoring, noise/sound level, gases/fugitive emissions, chemicals/toxins, fenceline monitoring (e.g. cordon off an area), and the like. In an embodiment, mere placement of the area monitors and establishment of a peer network, as described herein, may cause the auto-establishment of fencelines and perimeters.

In an embodiment, portable, compact systems for estimating heat index may include a temperature sensor, a humidity sensor, and one or more microphones. Portable detection equipment 108 and area detection equipment 110, such as equipment useful in the worker safety system, may be used in environments where heat may negatively affect the equipment, the equipment's user(s), or both. For detection equipment, it may be advisable to monitor the environment to assure proper operation of the equipment and user safety. While a temperature sensor will provide some information, an estimate of the heat index may provide more insight into potential heat-related impact on equipment and users.

Historically, combined data from temperature and humidity sensors have been used to calculate a heat index. In some systems, a vane anemometer may be used to calculate wind speed and the calculated wind speed may be factored into the calculation of heat index. However, vane anemometers may be large, making it difficult to incorporate into pieces of detection equipment, potentially necessitating the need for a user to carry multiple pieces of detection equipment.

Figure 21:
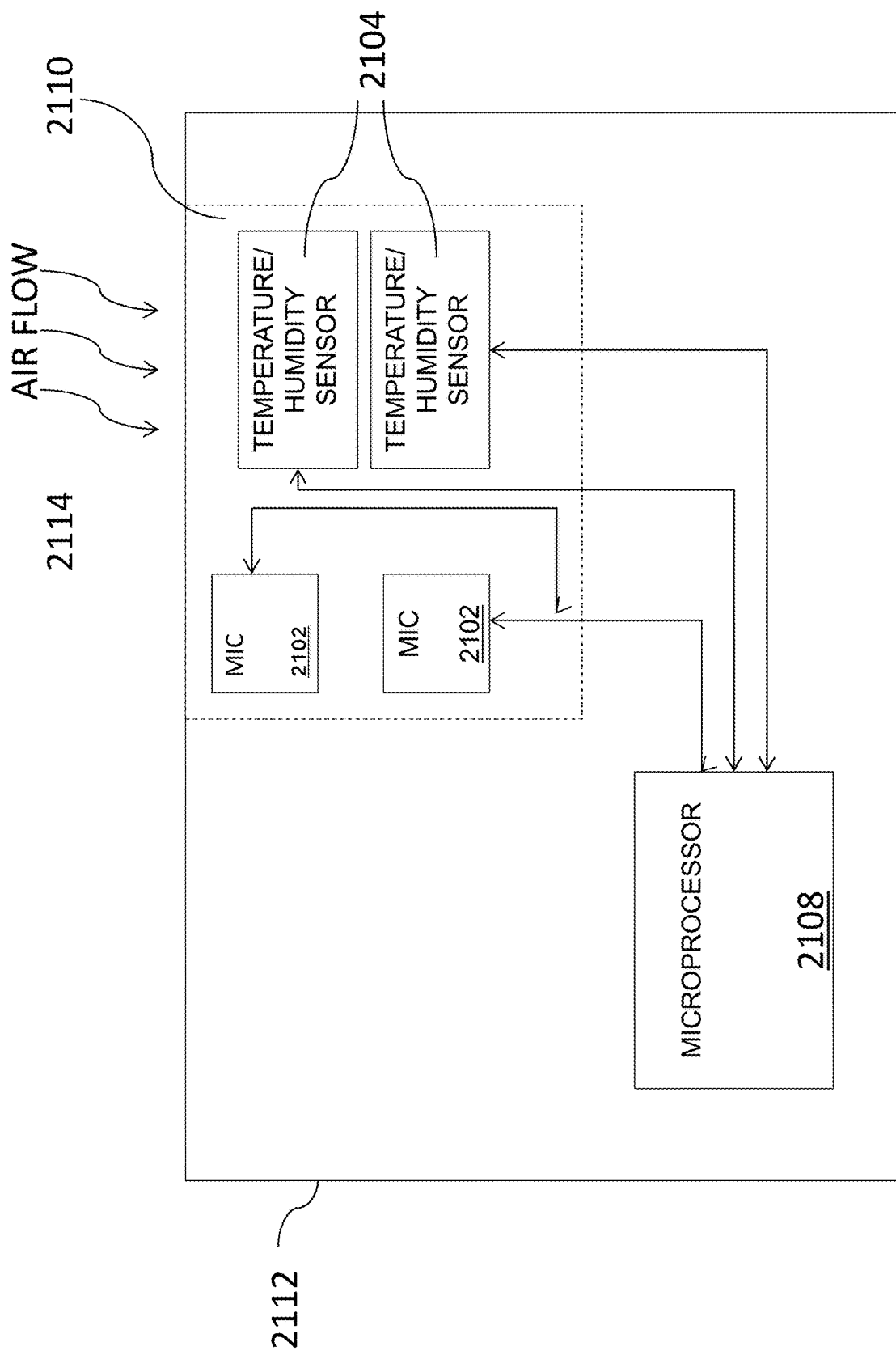
FIG. 21 depicts a system for estimating heat index incorporated into existing detection equipment.

FIG. 21 depicts a heat index estimation system 2110 which may include at least two microphones 2102 and temperature and humidity sensors 2104 in electrical communication with a microprocessor 2108 for calculating a heat index from the data provided by the microphones 2102 and temperature and humidity sensors 2104. The components of the heat estimation system 2110, such as the microphones 2102 and temperature and humidity sensors 2104, may be solid-state components for inclusion in detection equipment 2112. In embodiments, the microprocessor 2108 is a component of the equipment 2112, however, it should be understood that the system 2110 may also or instead include its own microprocessor and/or networking capability.

The heat index estimation system 2110 may be modular with respect to the detection equipment 2112 for ease of incorporation, insertion and/or removal without disassembly of the equipment 2112. Further, the system 2110 may be modularly interchangeable with other modules of the equipment. The heat index estimation system 2110 may be integrally incorporated into the detection equipment 2112. In embodiments, the ability to utilize solid-state temperature and humidity sensors with solid state microphones for estimating wind speed renders the combination, embodied in the system 2110, capable of fitting inside the detection equipment 2112 and capable of modularity with respect to the detection equipment 2112.

In embodiments, the components of the heat estimation system 2110 may be thermally isolated from one another.

The detection equipment 2112 may include at least one of a portable or area environmental sensing device, a portable or area gas sensor, a portable or area multi-gas detection instrument, a respirator, a lighting device, a fall arrest device, a thermal detector, a flame detector, and a chemical, biological, radiological, nuclear, and explosives (CBRNE) detector.

Figure 22:
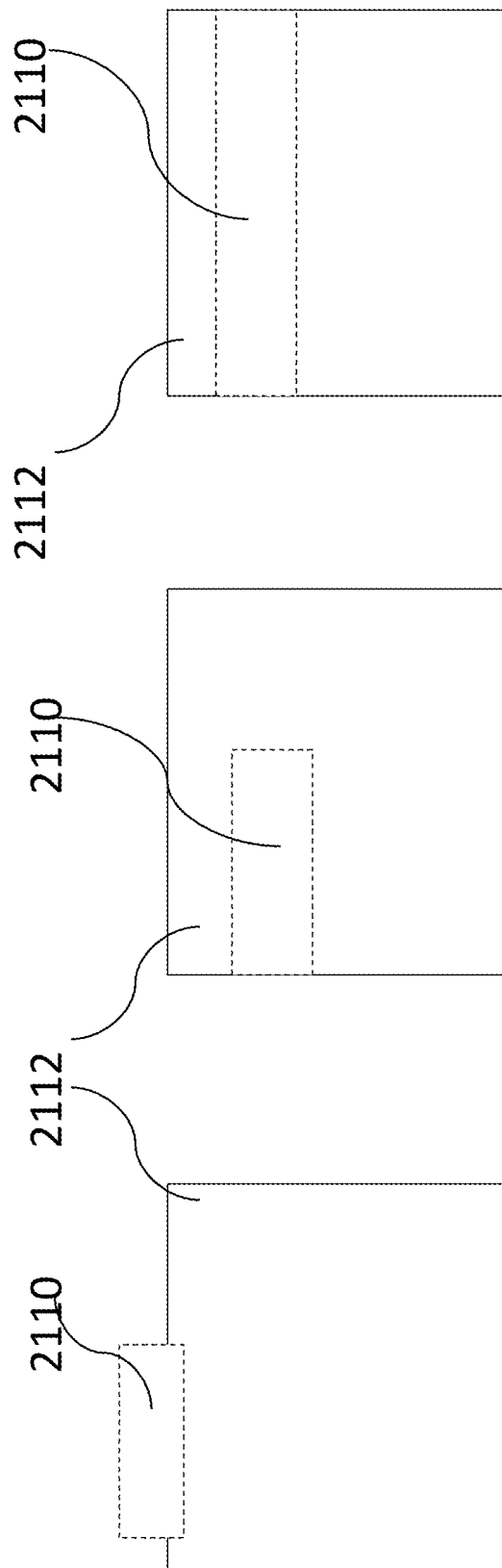
FIGS. 22A-22C depict various configurations of a heat index estimation system connected to or incorporated into detection equipment.

The heat index estimation system 2110 may be located on a surface of the piece of detection equipment 2112 (FIG. 22A) or located in a cavity of the piece of equipment that is open to airflow 2114 (FIG. 22B).

Figure 23:
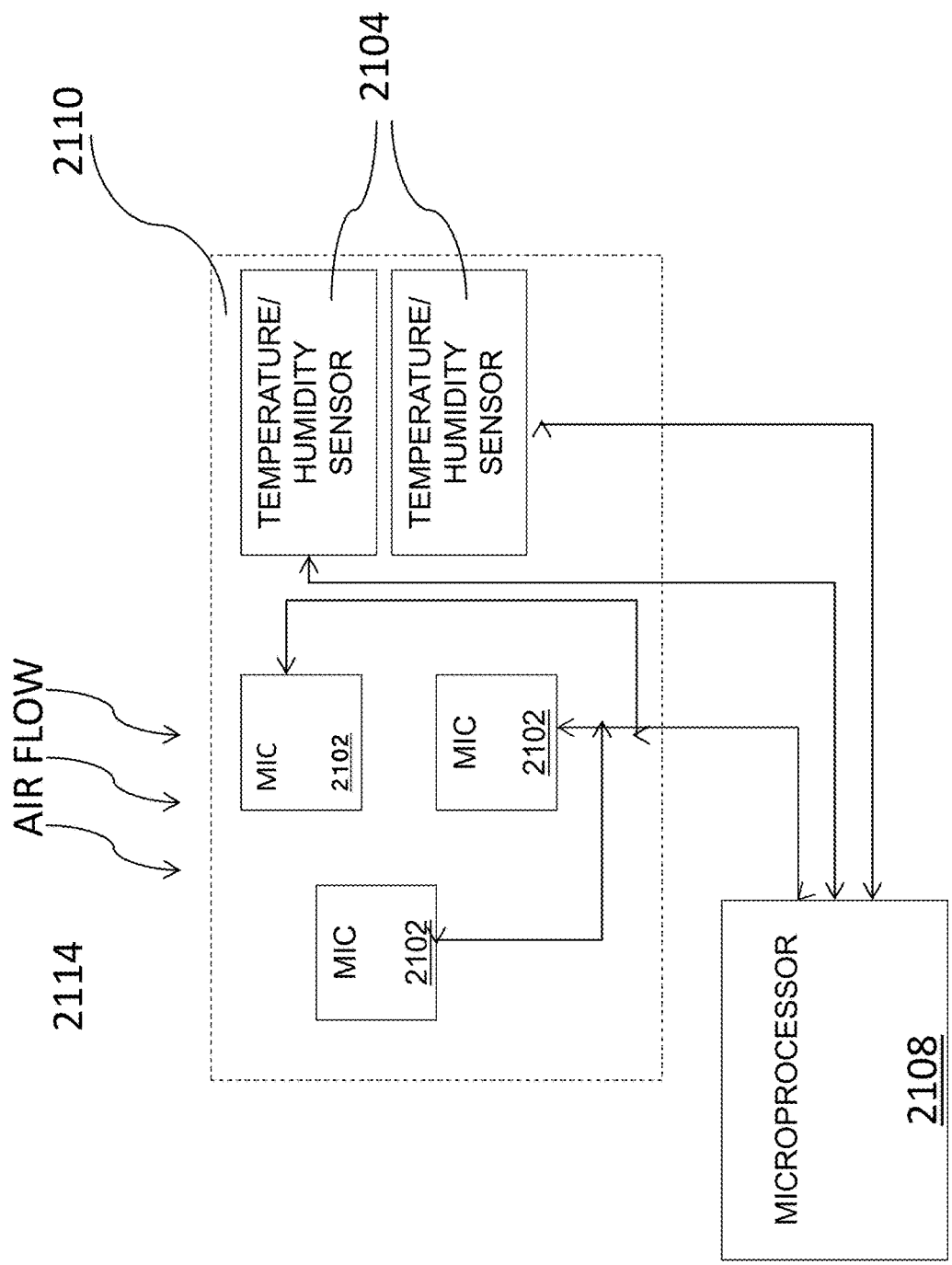
FIG. 23 depicts a system for estimating heat index incorporating three microphones.

The two microphones 2102 may be located linearly in a direction of the airflow 2114. In embodiments, there may be at least one additional microphone 2102 located non-linearly with respect to a line formed by the placement of the other microphones 2102 (FIG. 23). The microphone(s) may be directly subjected to wind or may be at the bottom of a recess that is subjected to wind.

The microprocessor 2108 may be electrically coupled to the microphones 2102 and sensors 2104. The microprocessor 2108 may analyze signals from the microphones 2102 for temporal, amplitude, and frequency differences to make a wind speed approximation, such as a maximum wind speed, an instantaneous wind speed, an average wind speed, and the like. For example, the microprocessor 2108 may analyze differences between sounds that arrive at each microphone to calculate the speed of wind across one or both of the microphones. In embodiments, one microphone may be shielded. Algorithms may be used to analyze the noise from a microphone exposed to the wind and compare it to the noise from a shielded microphone and to estimate wind speed. In embodiments, the algorithm may subtract the signal of the non-shielded microphone to obtain a wind component without ambient noise. In embodiments, a time delay between one microphone and a second microphone is used to determine a directional component of sound as a proxy for wind direction. In certain embodiments, a single microphone may be used and the wind velocity may be estimated from the volume of the wind.

A heat index may be calculated using a polynomial equation with sensed temperature and sensed absolute or relative humidity. The coefficients in the common equations known to one skilled in the art are typically based on a variety of assumptions, including a wind speed of approximately 5 mph. Knowing if the wind speed was more or less than 5 mph would enable the device to alert the user appropriately.

In some embodiments, a version of the system 2110 may not have microphones, and so would not use wind speed but could still provide heat index based on temperature and humidity data. This version of the system 2110 may also be modular with respect to the equipment 2112 and sized to be able to fit inside the equipment 2112. In embodiments, data from the humidity sensor, which may include relative and absolute humidity, may be used for sensor compensation.

In embodiments, the heat index information may be provided to a user of the detection equipment 2112, optionally along with guidelines for self-protection based on the calculated heat index. For example, if a calculated heat index reaches a threshold, the equipment 2112 may trigger an alarm on the equipment 2112 and any other nearby devices or networked devices or systems. The alarm may be audible, visual, haptic or any combination thereof. Self-protection guidelines may be displayed on the equipment or transmitted through a speaker of the equipment or other devices or system. Optionally, the calculated heat index may trigger a communication to the user and/or other interested party, such as a communication, call, message, and/or email. The communication may include a warning and/or self-protection guidelines.

Turning now to describing particular improvements to environmental sensing devices 108, 110, such as those that may be useful in the worker safety system, one such improvement relates to the use of a baseline auto-matching circuit for an LEL sensor.

Combustible gas detectors have been widely used in industry to detect and monitor the presence of combustible gases or vapors for safety and environmental purposes. They can provide an early warning of potentially explosive conditions to protect life and property before onset of a hazardous situation.

Multiple gas sensing technologies may be used in such gas detectors such as thermal conductivity sensors, infrared (IR) sensors, semiconductor (MOS) sensors and catalytic bead (or pellistor) sensors. Among these, catalytic bead sensors are most commonly used due to their low cost, high performance and wide coverage of target gases. A catalytic bead sensor typically contains two ceramic beads coated onto metal, such as platinum, wire coils, a sensing bead and a compensating bead. The sensing bead may be impregnated with a noble metal catalyst, which promotes combustion of the combustible gases or vapors, while the compensating bead may not contain a catalyst, but compensates for environmental effects such as humidity and ambient temperature changes.

Figure 24:
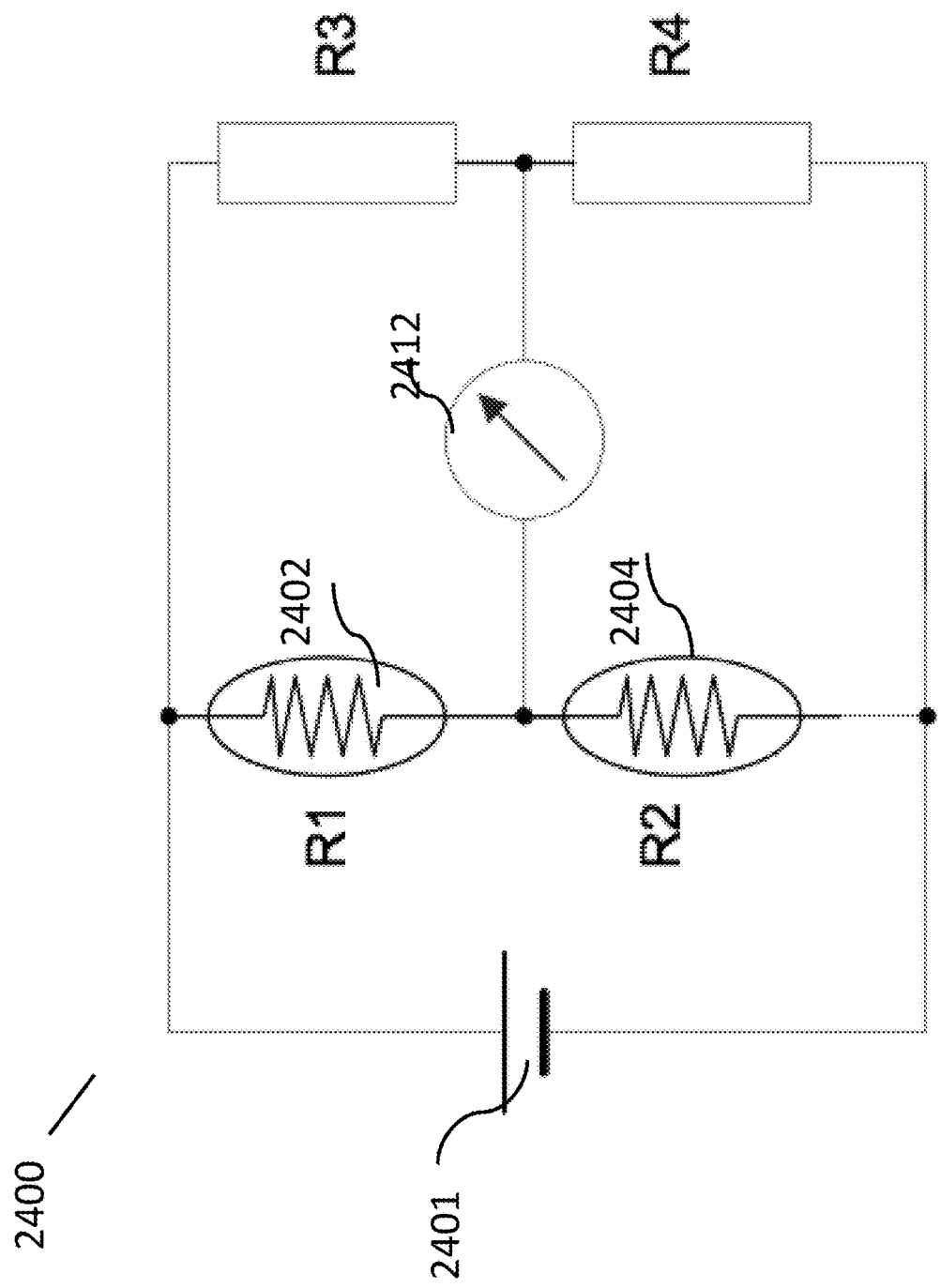
FIG. 24 depicts a Wheatstone bridge circuit.

There are multiple ways to configure the circuit of the two beads. Many commercial combustible gas detectors are based on a Wheatstone bridge 2400, an example of which is shown in FIG. 24 and described in U.S. Pat. No. 4,313,907. When an input voltage 2401 is applied across the bridge, resistive heating of the platinum wire coils and hence the beads 2402, 2404 takes place. In the presence of a combustible gas or vapor, catalytic combustion takes place on the sensing bead 2402 and generates combustion heat, causing an increase in the sensing bead 2402 temperature relative to the temperature of the compensating bead 2404 and, thus, the sensing bead 2402 wire resistance is increased relative to that of the compensating bead 2404. The increased resistance of the sensing bead 2402 generates the differential output signal 2412 between the two circuit branches, which is proportional to the gas concentration in a given measurement range.

When a gas detector is manufactured, the combustible gas sensor baseline (differential voltage output when there is no combustible gas present) is typically tuned to be close to zero by selecting two matched beads with close impedance.

Figure 25:
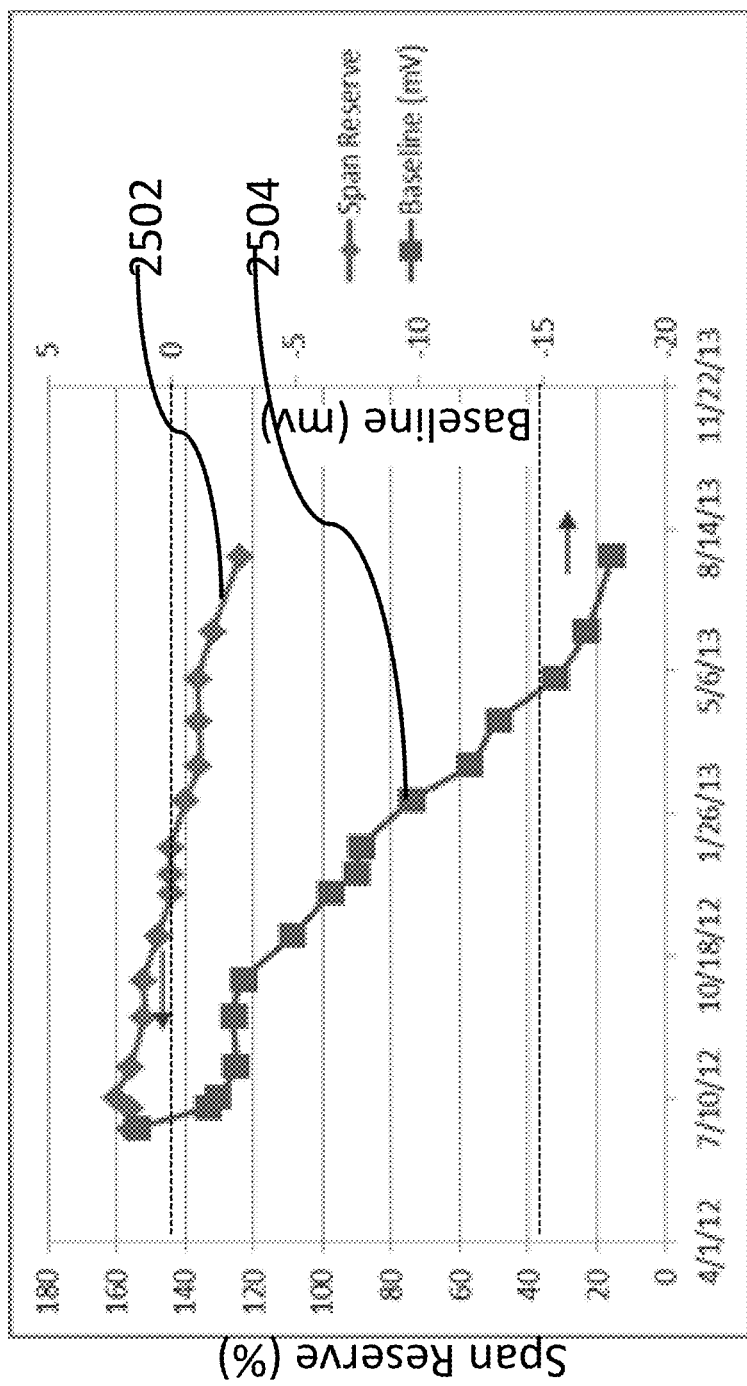
FIG. 25 depicts a gas sensor's span reserve and its baseline change over time.

When the detector is deployed for field use, the baseline may drift over the lifetime due to aging effects of the sensing bead 2402 and compensating bead 2404. FIG. 25 shows a graphic example of a typical combustible catalytic bead gas sensor's span reserve 2502 (or sensitivity) and its baseline (mV) 2504 change over a period of time.

The term Span Reserve harkens back to the days when gas monitoring instruments were driven by analog circuits and calibration was performed by adjusting the Zero and Span potentiometers. In that era, gas was applied to the instrument and the "span pot" was adjusted until the reading on the display matched the concentration of the gas being used. If you wanted to see how much life was in your sensor, you would turn the span potentiometer up all the way and the subsequent reading would show you how much reserve sensitivity was in the sensor or how much room for adjustment there was before the sensor could no longer be calibrated.

FIG. 25 depicts the baseline voltage slightly above zero mV at the beginning of the depicted time period and decreasing over the measured time to approximately negative 18 mV at the latest stage of life depicted. Prior art approaches to address this issue include auto-zeroing with software in gas detectors. However, this approach results in a corresponding loss in the span reserve 2502 (sensitivity) as shown by the reduction of span reserve shown in FIG. 25 from approximately 155% down to 120% over the same time period. Thus, auto-zeroing obscures the issue and does not resolve it, allowing the Wheatstone bridge to continue becoming more unbalanced over time.

Thus, there remains a need for balanced bridge circuit configurations for combustible gas detectors that can maintain span reserve (sensitivity) over time.

Figure 26A:
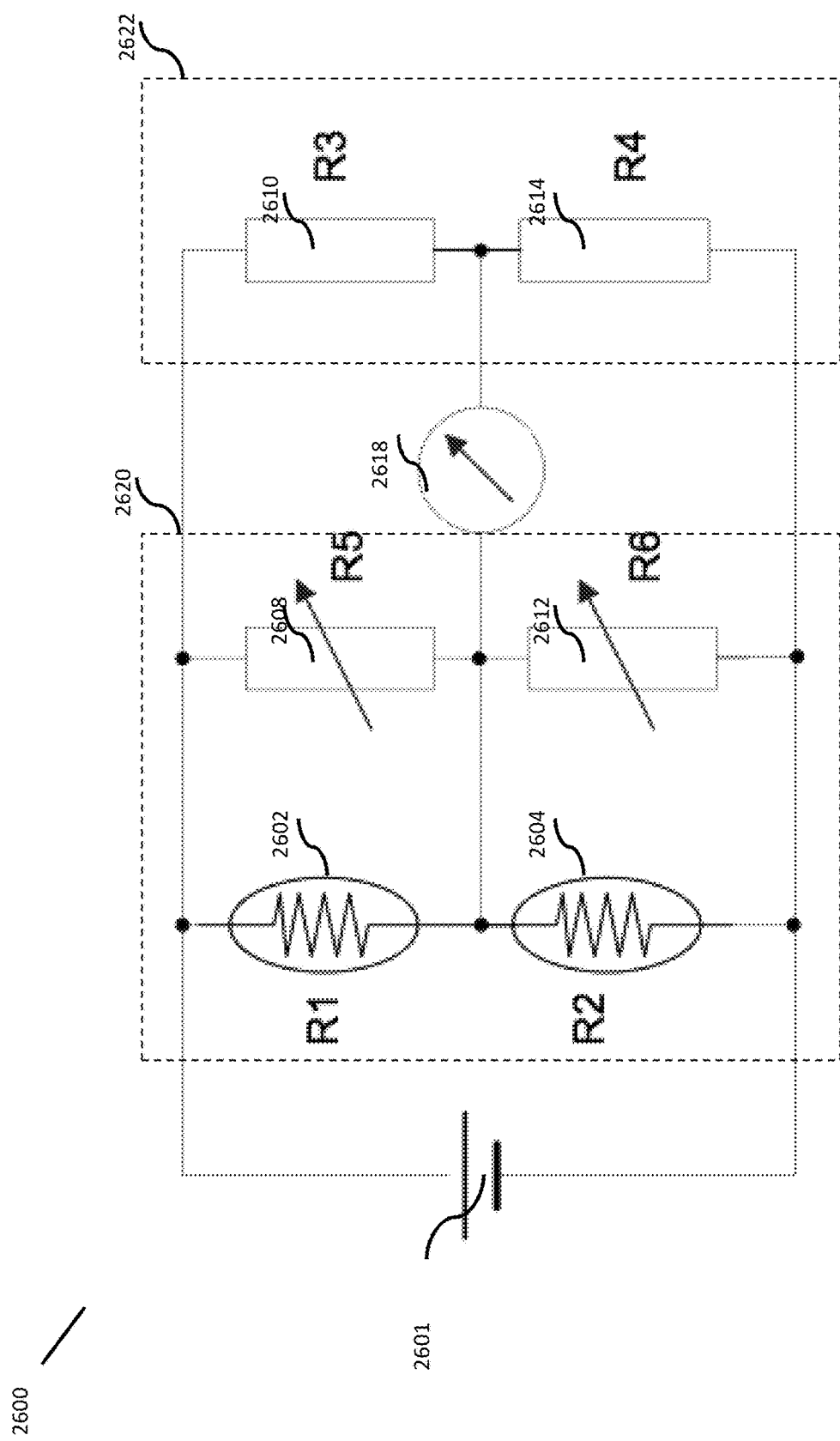
FIGS. 26A-26C depict balanced bridge circuits.

FIG. 26A depicts a balanced bridge circuit 2600 having two branches, each connected in parallel with a power source 2601. The first branch 2620 has a sensing bead R1 2602 and a compensating bead R2 2604 connected in series. Sensing bead R1 2602 is further connected in parallel with a variable resistor R5 2608 and compensating bead R2 2604 is further connected in parallel with a variable resistor R6 2612. The second branch 2622 has a standard resistor R3 2610 and a standard resistor R4 2614 connected in series. A differential output meter 2618 measures the baseline voltage and is disposed between the first branch 2620 and the second branch 2622 with one side connected between the sensing bead 2602 and the compensating bead 2604 and the other side connected between the standard resistors 2610, 2614. This configuration may enable any unbalance of the circuit due to changes, such as aging or other deterioration, of the sensing bead R1 2602 or compensating bead R2 2604 to be adjusted by varying one of the variable resistors R5 2608 or R6 2612 where the variable resistor adjusted may be selected based on the degree of drift in bead R1 2602 relative to drift in bead R2 2604 so as to maintain the baseline as indicated by differential output meter 2618 reading close to zero mV. In this and the following circuits, it is understood that the location in the circuit of the sensing bead R1 2602 and the compensating bead R2 2604 may be switched.

Figure 26B:
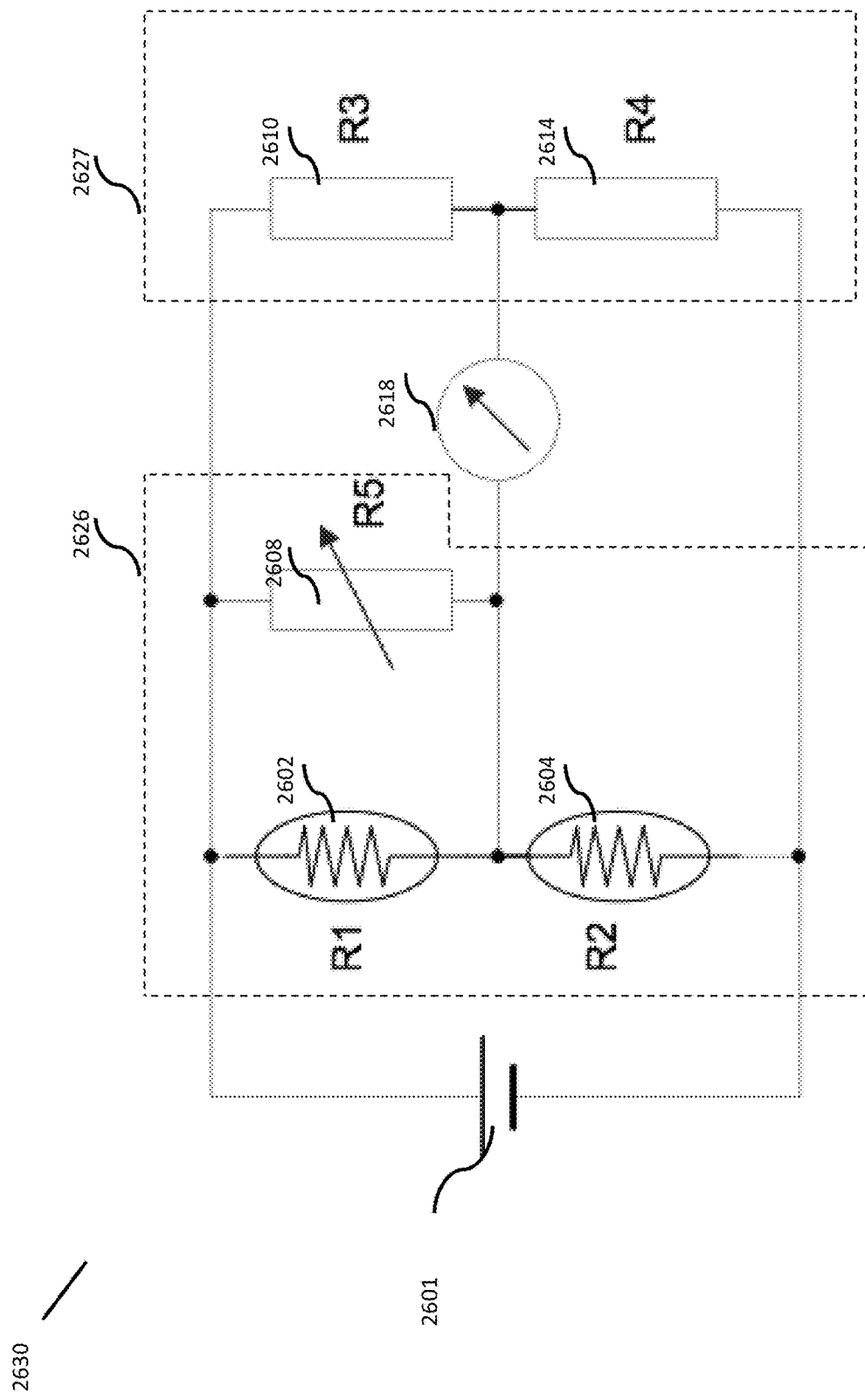
Figure 26C:
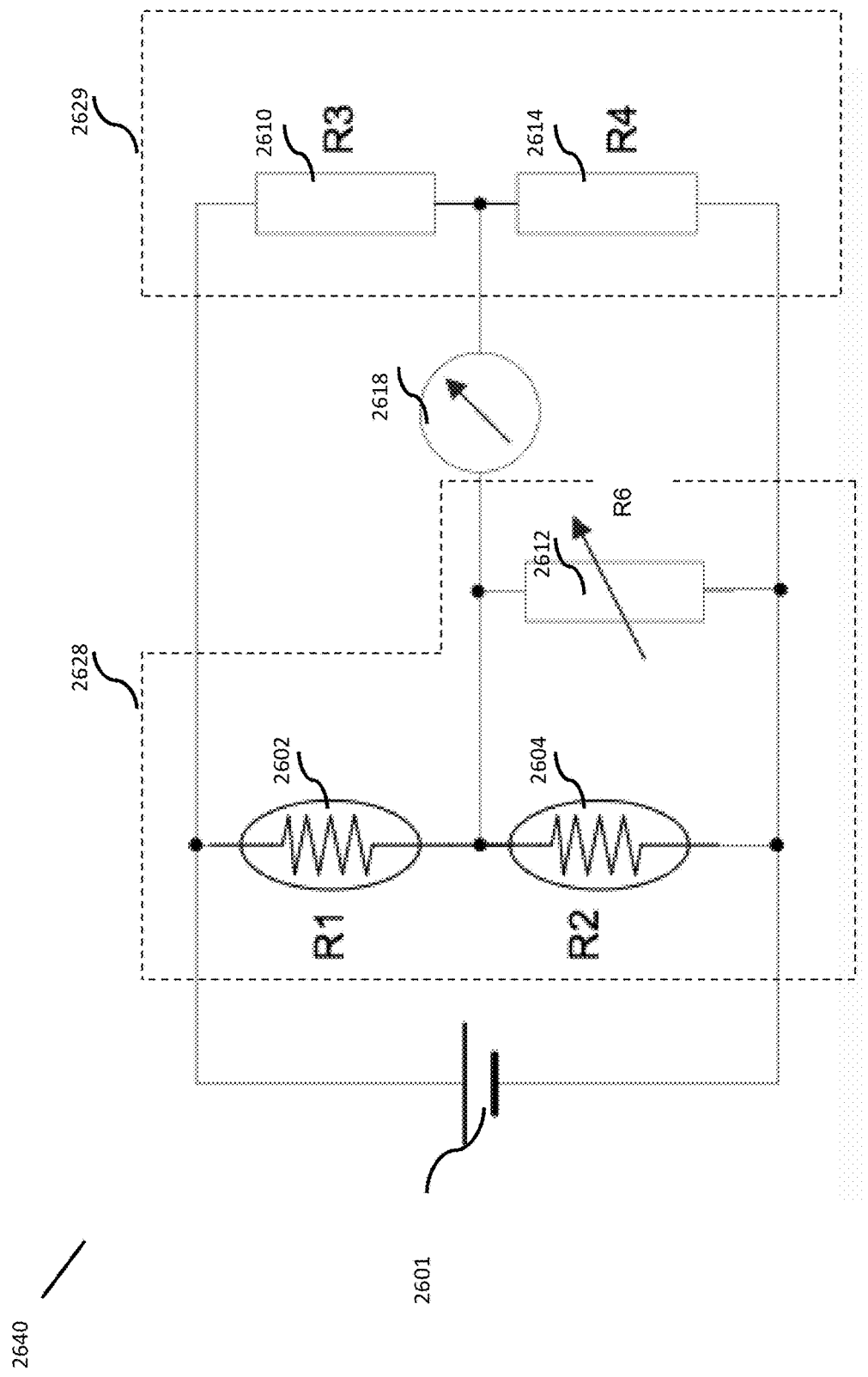

In other embodiments, a single variable resistor may be used as shown in FIGS. 26B-26C. Referring to FIG. 26B, a balanced bridge circuit 2630 is depicted having two branches connected in parallel with a power source 2601. The first branch 2626 has a sensing bead R1 2602 in series with a compensating bead R2 2604. Sensing bead R1 2602 is further connected in parallel with a variable resistor R5 2608. The second branch 2627 has a standard resistor R3 2610 connected in series with resistor R4 2614. A differential output meter 2618 measures the baseline voltage and is disposed between the first branch 2626 and the second branch 2627 with one side connected between the sensing bead 2602 and the compensating bead 2604 and the other side connected between standard resistors R3 2610 and R4 2614. The value of variable resistor R5 2608 may be adjusted to compensate for changes in the resistance of sensing bead R1 2602. This solution works if the value of sensing bead R1 2602 is higher than that of compensating bead R2 2604. Otherwise, the circuit may not be able to adjust the balance point given that the parallel connection will only reduce the total resistance.

Referring to FIG. 26C, a balanced bridge circuit 2640 is depicted having two branches connected in parallel with a power source 2601. The first branch 2628 has a sensing bead R1 2602 and a compensating bead R2 2604 connected in series. Compensating bead R2 2604 is further connected in parallel with a variable resistor R6 2612. The second branch 2629 has two standard resistors R3 2610 and R4 2614 connected in series. Although two resistors are shown more than two may be used. A differential output meter 2618 measures the baseline voltage and is disposed between the first branch 2628 and the second branch 2629 with one side connected between the sensing bead 2602 and the compensating bead 2604 and the other side connected between the standard resistors 2610, 2614. The value of variable resistor R6 2612 may be adjusted to compensate for changes in the resistance of compensating bead R2 2604. The use of a single variable resistor may save cost on hardware relative to the two variable resistor embodiment of FIG. 26A. This solution works if the value of sensing bead R1 2602 is lower than that of compensating bead R2 2604.

Figure 27A:
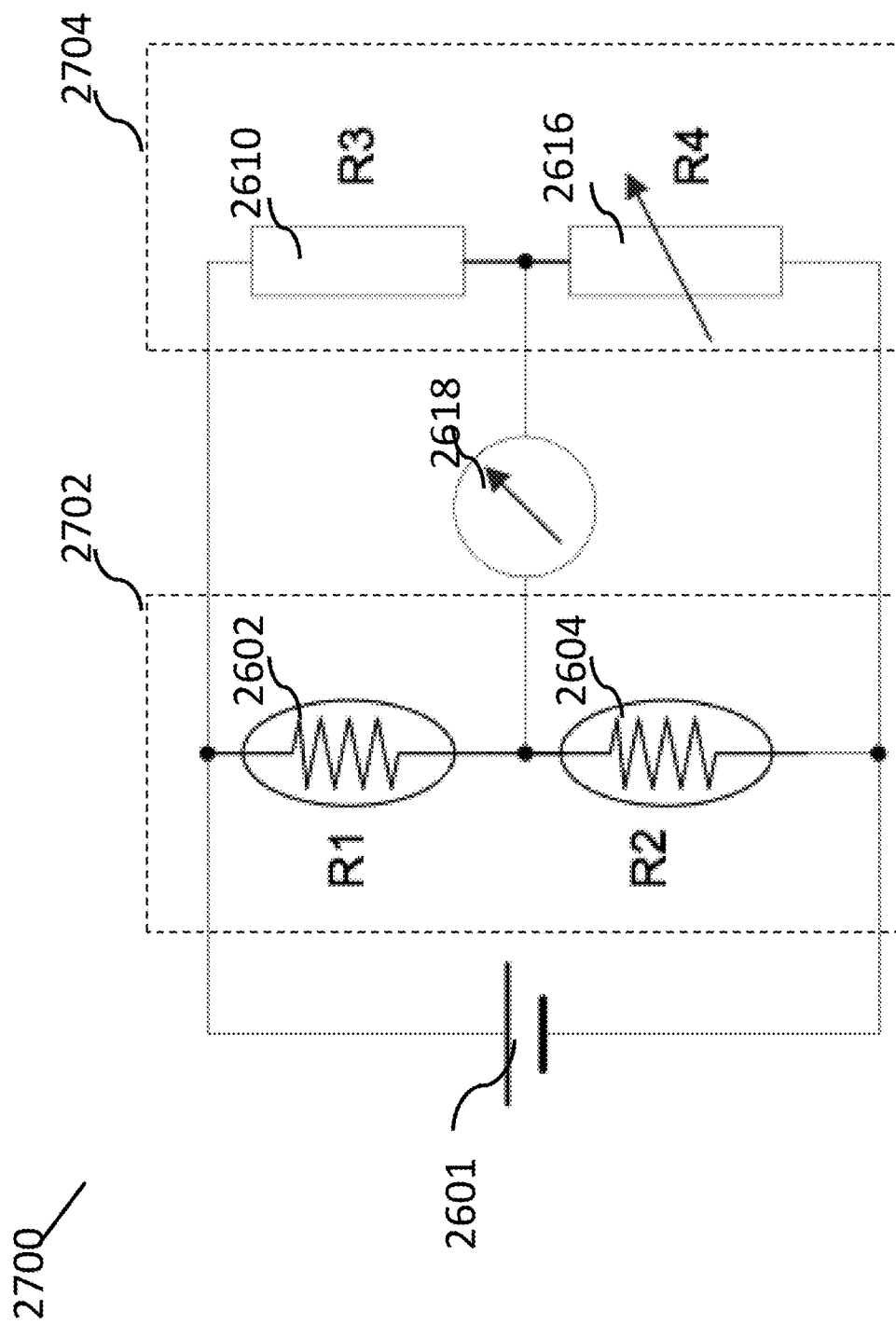
FIG. 27A depicts a balanced bridge circuit.
Figure 27B:
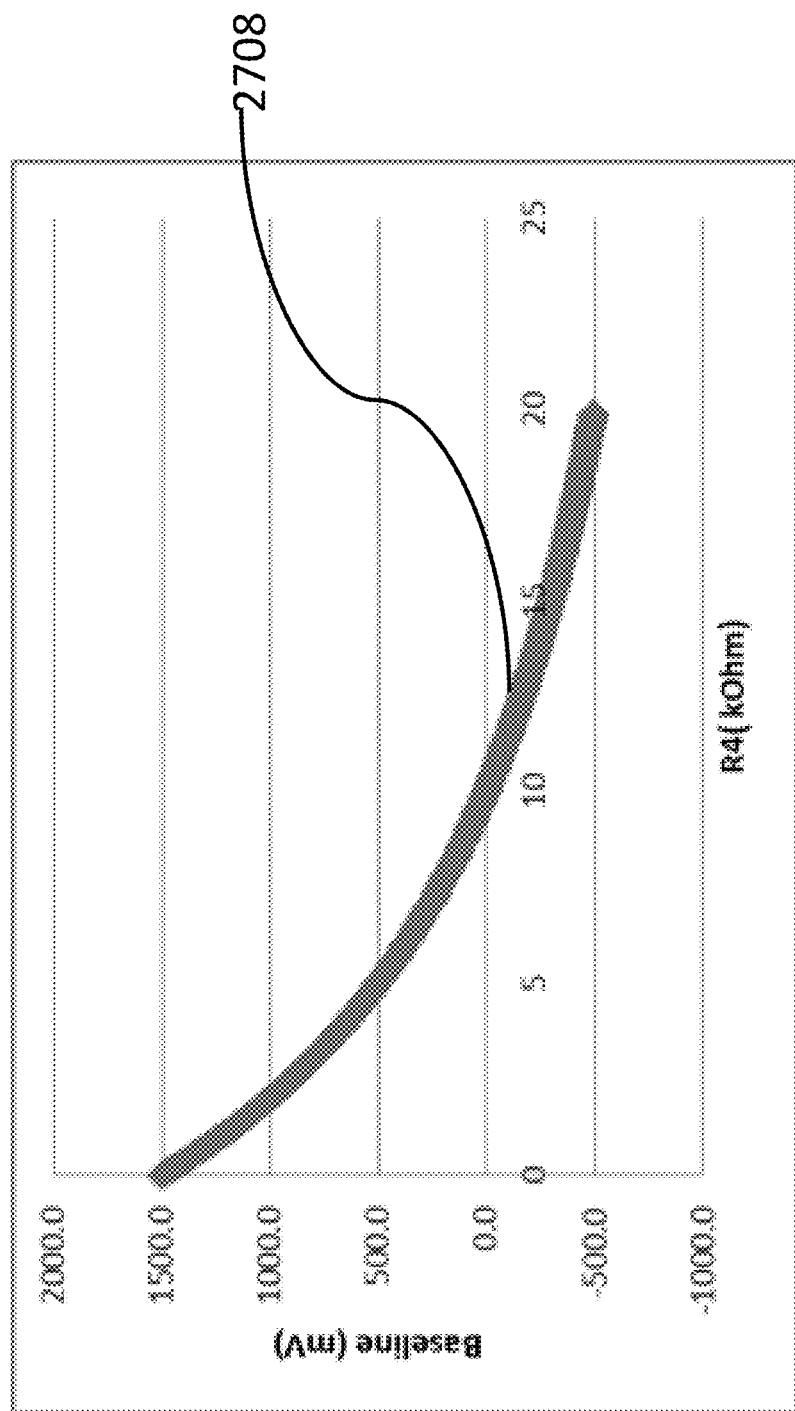
FIG. 27B depicts the relationship between component value and baseline

Another embodiment of a balanced bridge circuit 2700 is depicted in FIG. 230A. There are two branches connected in parallel with each other and a power source 2601. The first branch 2702 has a sensor bead 2602 and a compensating bead 2604 connected in series. The second branch 2704 has two resistors, R3 2610 and R4 2616 connected in series. As the resistances of the beads 2602, 2604 in the first branch 2702 change with age, the ratio of the resistors in the second branch 2704 may be adjusted to achieve the desired baseline. To achieve this, either R3 2610 or R4 2616 (as shown in FIG. 27A) may be a variable resistor. A differential output meter 2618 disposed between the two branches measures a baseline voltage with one side of the meter 2618 connected to the first branch 2702 between the sensor bead 2602 and the compensating bead 2604 and the other side of the meter being connected to the second branch 2704 between the two resistors 2610, 2616. Whenever there is a need to balance the bridge circuit, the variable resistor (R3 2610 or R4 2616) will be adjusted or "tuned" to compensate for the relative changes of the beads R1 2602 and R2 2604 branch. For example, if R3 2610 equals 10K ohms and the power applied to the bridge is 3V, the simulated baseline resulting from tuning R4 2616 is shown in FIG. 27B. Referring to FIG. 27B, the baseline voltage 2708 is shown as a function of the value of variable resistor R4 2616. This configuration facilitates adjusting the baseline voltage 2708 over a wide range by adjusting the value of the variable resistor R4 2616, enabling tuning the circuit to adjust for changes to the baseline by adjusting the value of variable resistor R4. However, this tuning circuit results in large changes in baseline voltage 2708 for relatively small changes in the value of variable resistor R4 2616.

Figure 28A:
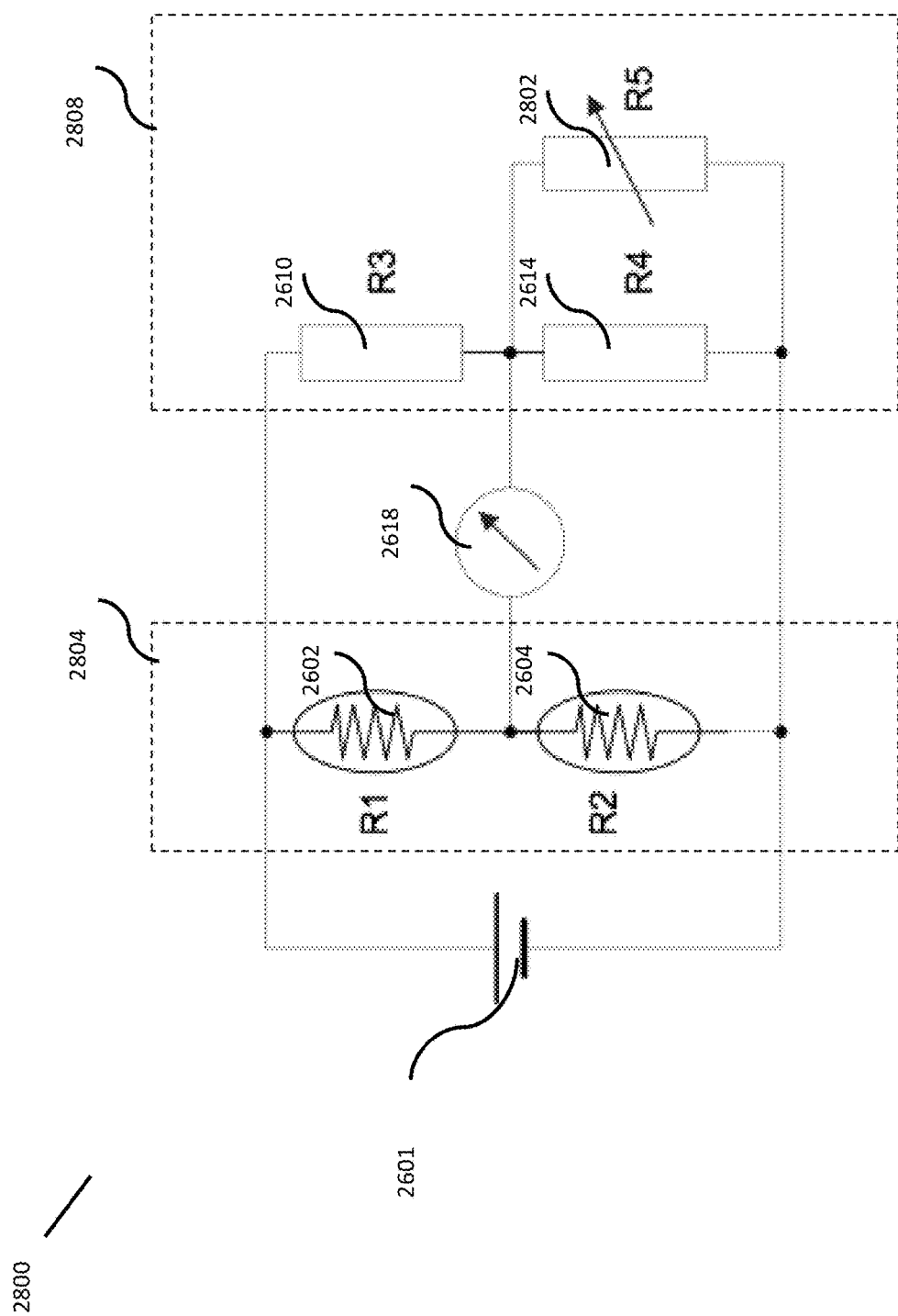
FIG. 28A depicts a balanced bridge circuit.
Figure 28B:
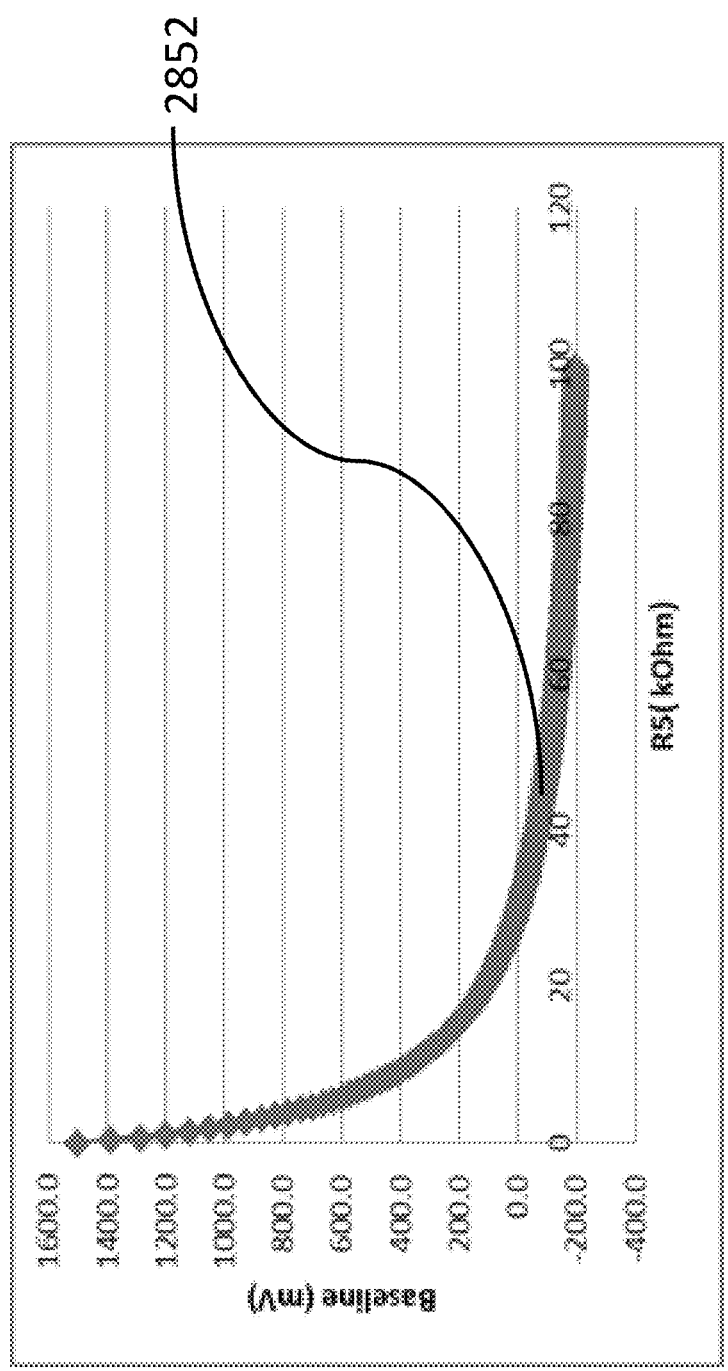
FIG. 28B depicts the relationship between component value and baseline.

FIG. 28A illustrates another embodiment of a balanced bridge circuit 2800. There are two branches connected in parallel with each other and a power source 2601. The first branch 2804 has a sensor bead 2602 and a compensating bead 2604 connected in series. The second branch 2808 has two standard resistors, R3 2610 and R4 2614. The second branch 2808 also includes a variable resistor R5 2802, which may be connected in parallel with either resistor R3 2610 or R4 2614 (shown). A differential output meter 2618 disposed between the two branches measures a baseline voltage with one side of the meter 2618 connected to the first branch 2804 between the sensor bead 2602 and the compensating bead 2604 and the other side of the meter being connected to the second branch 2808 between the two resistors 2610, 2614. FIG. 28B shows a simulation of the baseline voltage 2852 as a function of the value of variable resistor R5 2802 when it is in parallel with resistor R4 2614. This circuit may enable fine-tuning of the baseline voltage over a portion of the range of the variable resistor R5 2802. The range over which the circuit may be finely tuned varies depending on whether the variable resistor R5 2802 is in parallel with R3 2610 or R4 2614.

Figure 29A:
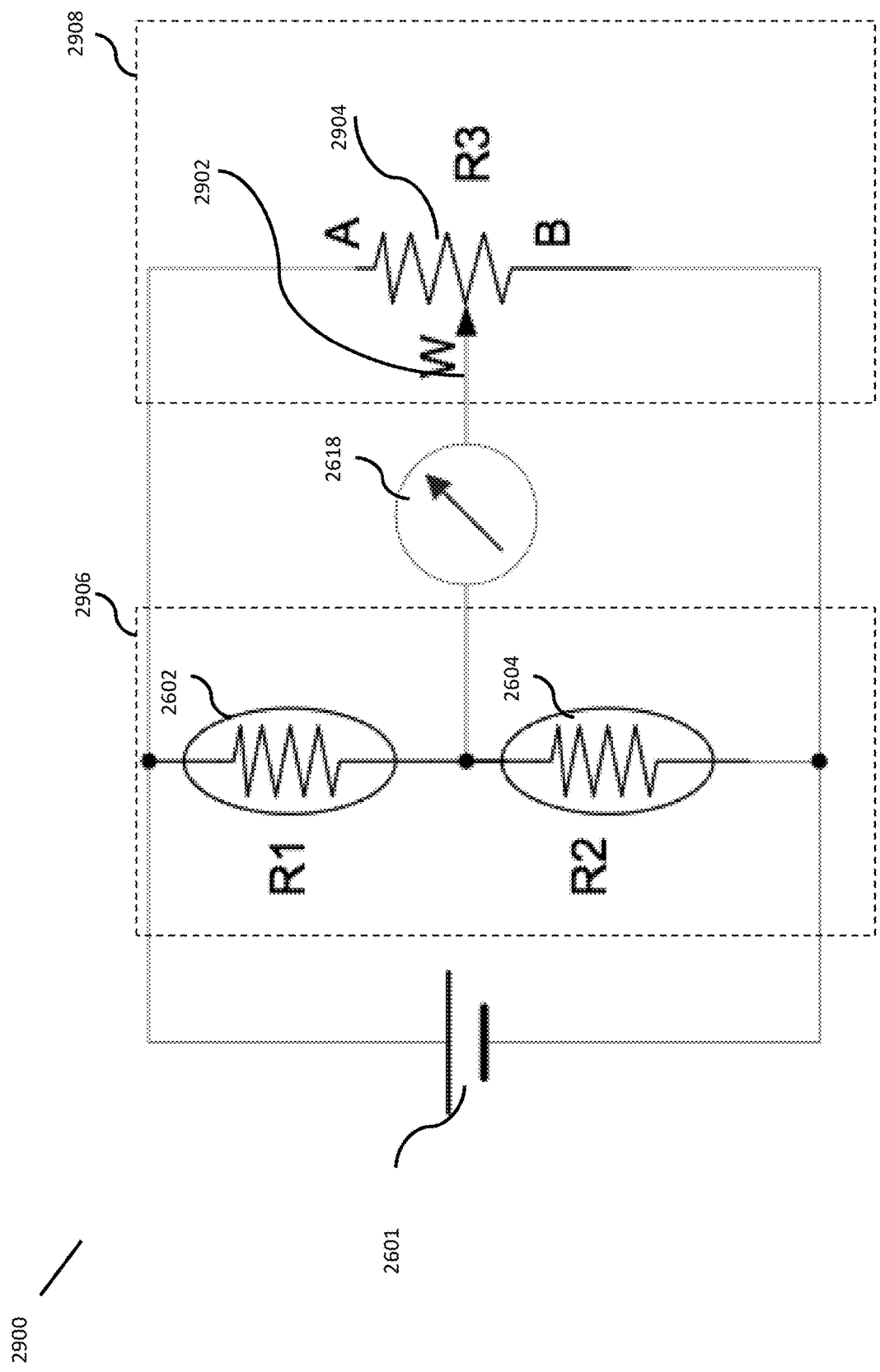
FIG. 29A depicts a balanced bridge circuit.
Figure 29B:
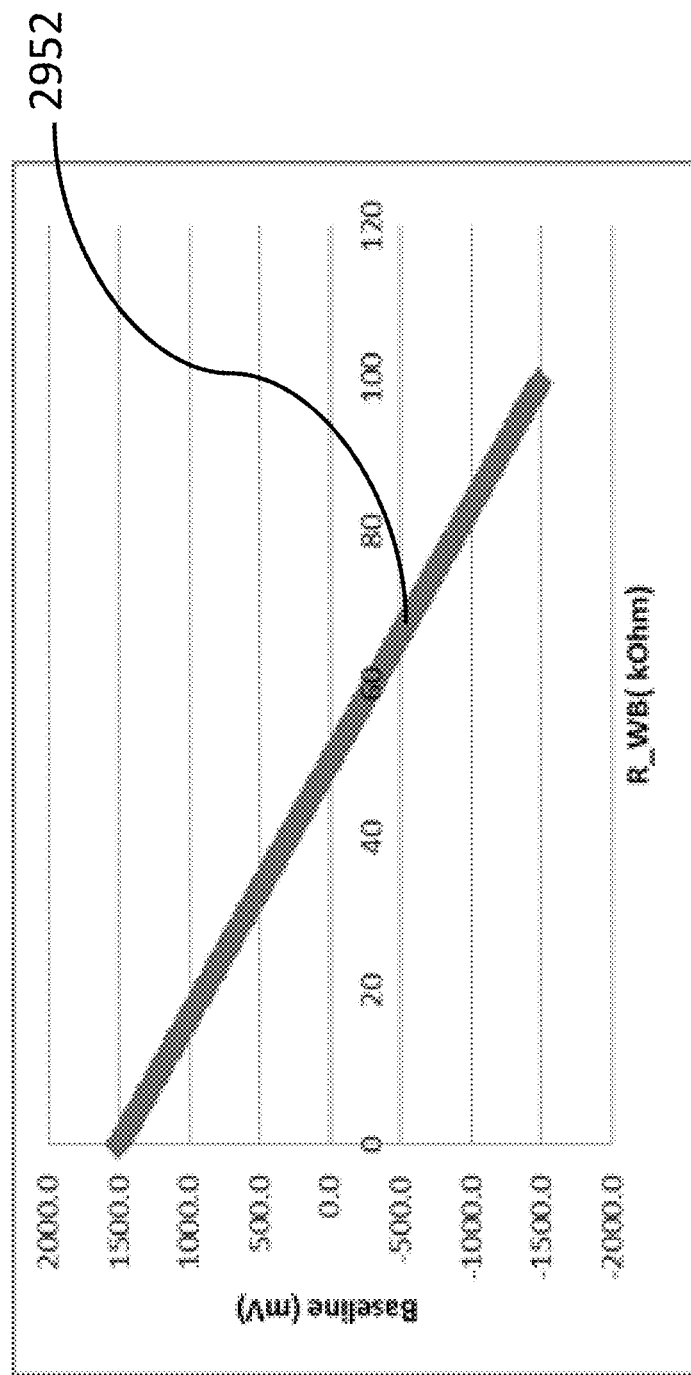
FIG. 29B depicts the relationship between component values and baseline.

Instead of tuning on one side, FIG. 29A shows an embodiment of a balanced bridge circuit 2900 that may enable tuning on both sides. There are two branches connected in parallel with each other and a power source 2601. The first branch 2906 has a sensor bead 2602 and a compensating bead 2604 connected in series. The second branch 2908 comprises two terminals of a three-terminal variable resistor (potentiometer) R3 2904 forming the second branch. A differential output meter 2618 disposed between the two branches measures a baseline voltage with one side of the meter 2618 connected to the first branch 2906 between the sensor bead 2602 and the compensating bead 2604 and the other side of the meter being connected to the wiper 2902 terminal of the three-terminal variable resistor R3 2904 forming the second branch 2908. In this way, by adjusting the wiper 2902 up and down, the second branch 2908 may be adjusted to match changes to the beads, R1 2602 and R2 2604. FIG. 29B depicts a simulation of the resulting change in baseline differential output 2952 as the wiper 2902 is adjusted. This embodiment results in a linear tuning curve where the baseline differential output varies linearly with the adjustment of the wiper 2902.

Figure 30A:
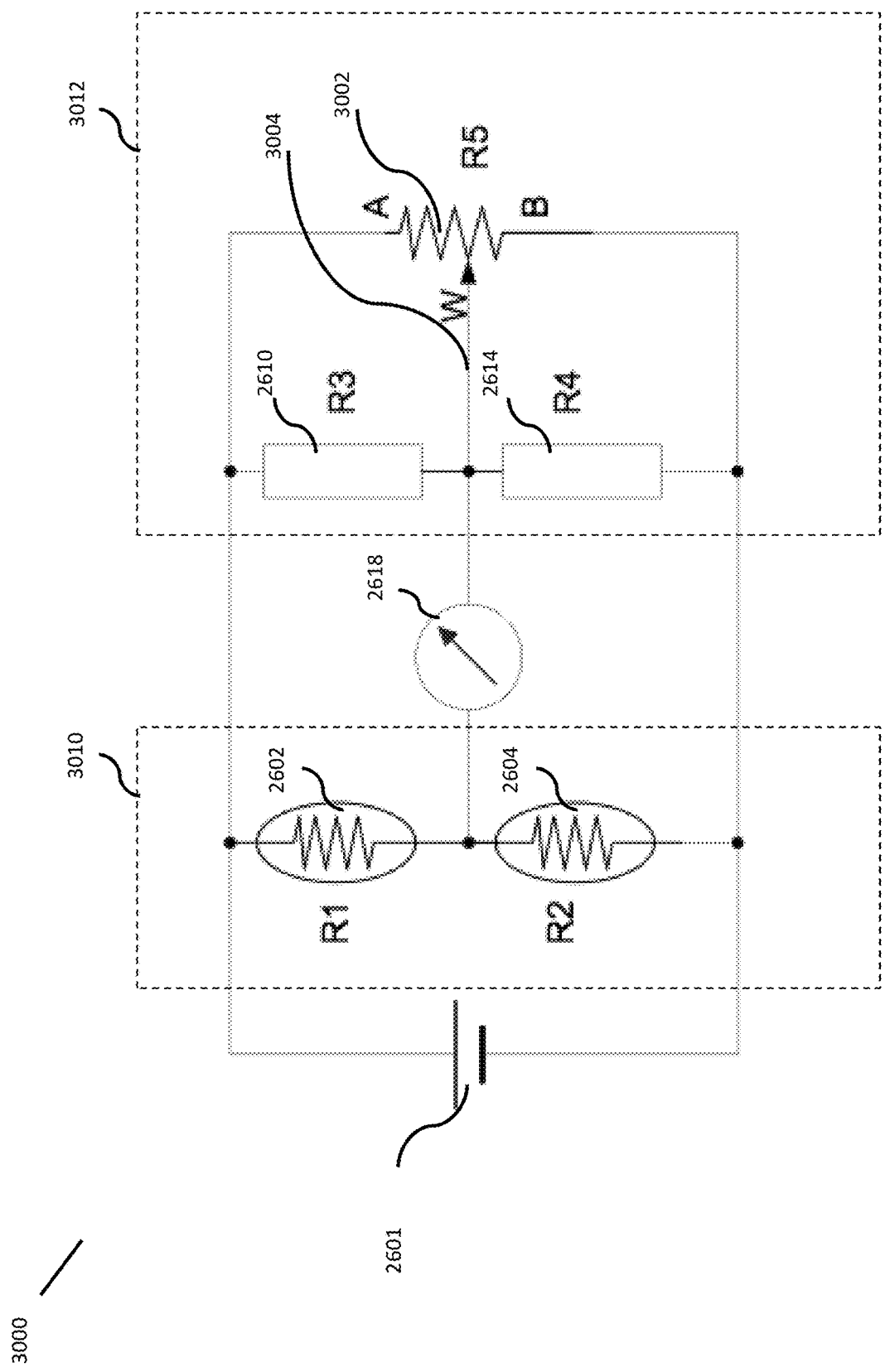
FIG. 30A depicts a balanced bridge circuit.
Figure 30B:
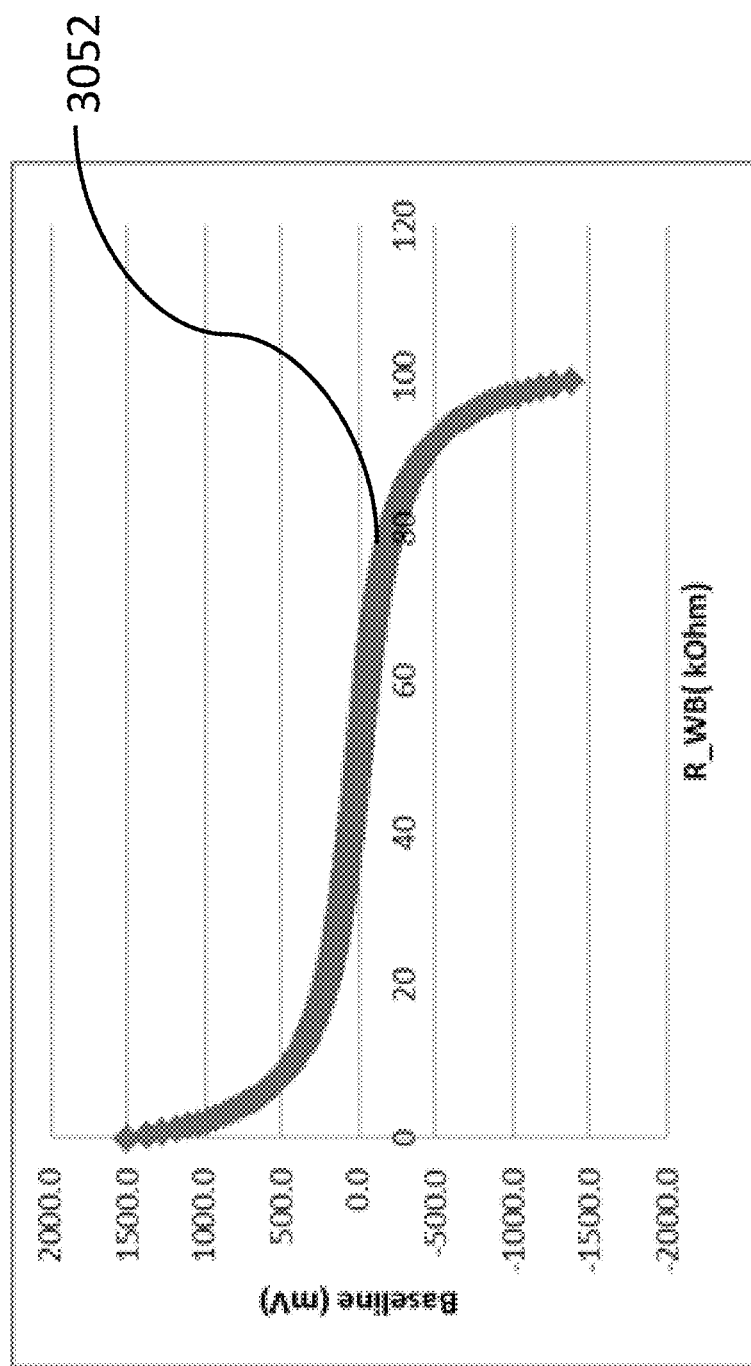
FIG. 30B depicts the relationship between component value and baseline.

FIG. 30A shows another embodiment of a balanced bridge circuit 3000 which is a variant of the embodiment of FIG. 29A. There are two branches connected in parallel with each other and a power source 2601. The first branch 3010 has a sensor bead 2602 and a compensating bead 2604 connected in series. The second branch 3012 has a three-terminal variable resistor 3002, which may be a digital potentiometer, connected in parallel to standard resistors R3 2610 and R4 2614. The wiper 3004 of the three-terminal variable resistor 3002 may be connected between the two standard resistors R3 2610 and R4 2614. A differential output meter 2618 disposed between the two branches measures a baseline voltage with one side of the meter 2618 connected to the first branch 3010 between the sensor bead 2602 and the compensating bead 2604 and the other side of the meter being connected between to the wiper 3004 of the three-terminal variable resistor R3 3002 and between the two standard resistors R3 2610 and R4 2614. In this way, by moving the wiper 3004 up and down, the bridge may be adjusted to match the changes of beads R1 2602 and R2 2604. Considering the typical baseline drift of a catalytic sensor may be small, this circuit may enable accurate tuning. FIG. 30B depicts a simulation of the resulting change in baseline differential output 3052 as the wiper 3004 is adjusted. In the middle range of the matching point, the tuning step is very fine. For example, assuming R3 2610 and R4 2614 is 10K ohms, R5 3002 is 100K ohms, and the power supply 2601 is 3V, the adjustable baseline 3052 may be as small as 2 mV.

Figure 31:
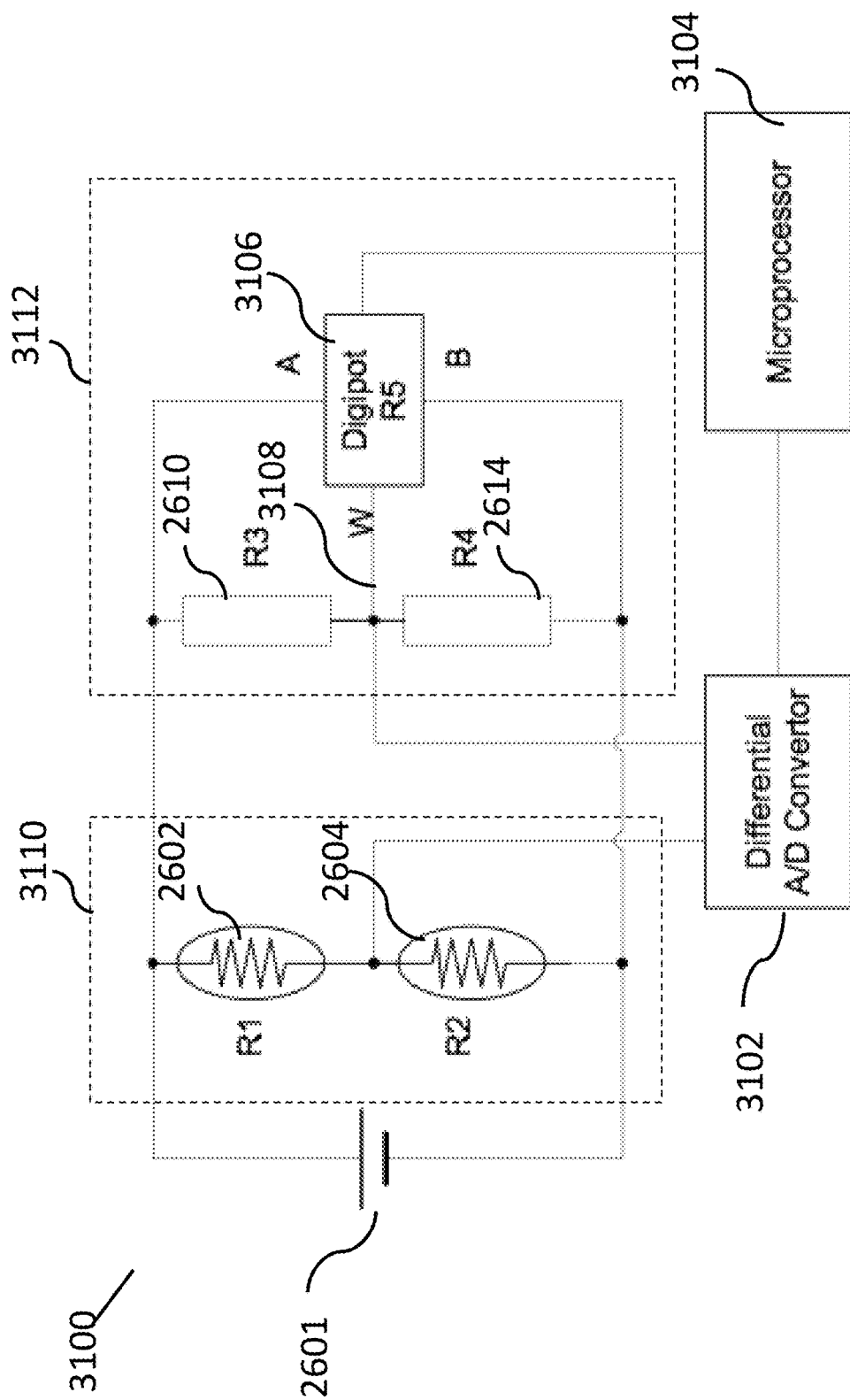
FIG. 31 depicts a balanced bridge circuit.

FIG. 31 shows an embodiment of a bridge circuit 3100 being balanced through a digital potentiometer and microprocessor in a gas detector. There are two branches connected in parallel with each other and a power source 2601. The first branch 3110 has a sensor bead 2602 and a compensating bead 2604 connected in series. The second branch 3112 has a three-terminal digital potentiometer 3106, connected in parallel to two standard resistors R3 2610 and R4 2614 connected in series. A differential A/D convertor is disposed between the two branches with the connection to the first branch 3110 located between the sensor bead 2602 and the compensating bead 2604. The connection to the second branch 3112 is connected between the two standard resistors R3 2610 and R4 2614 to the wiper 3108 of the digital potentiometer 3106. When the bridge circuit is balanced, the differential output voltage detected by microprocessor 3104 through A/D convertor 3102 stays close to zero if there is no combustible gas present. When a significant baseline drift happens, the differential output will become non-zero (above the tolerance range i.e. 10 mV) even if there is no combustible gas present. At this time, the instrument may send a command to digital potentiometer R5 3106 to change its position of wiper 3108 to match the new R1 2602/R2 2604 values until differential output voltage drops within a tolerance range (i.e. 10 mV).

Figure 32A:
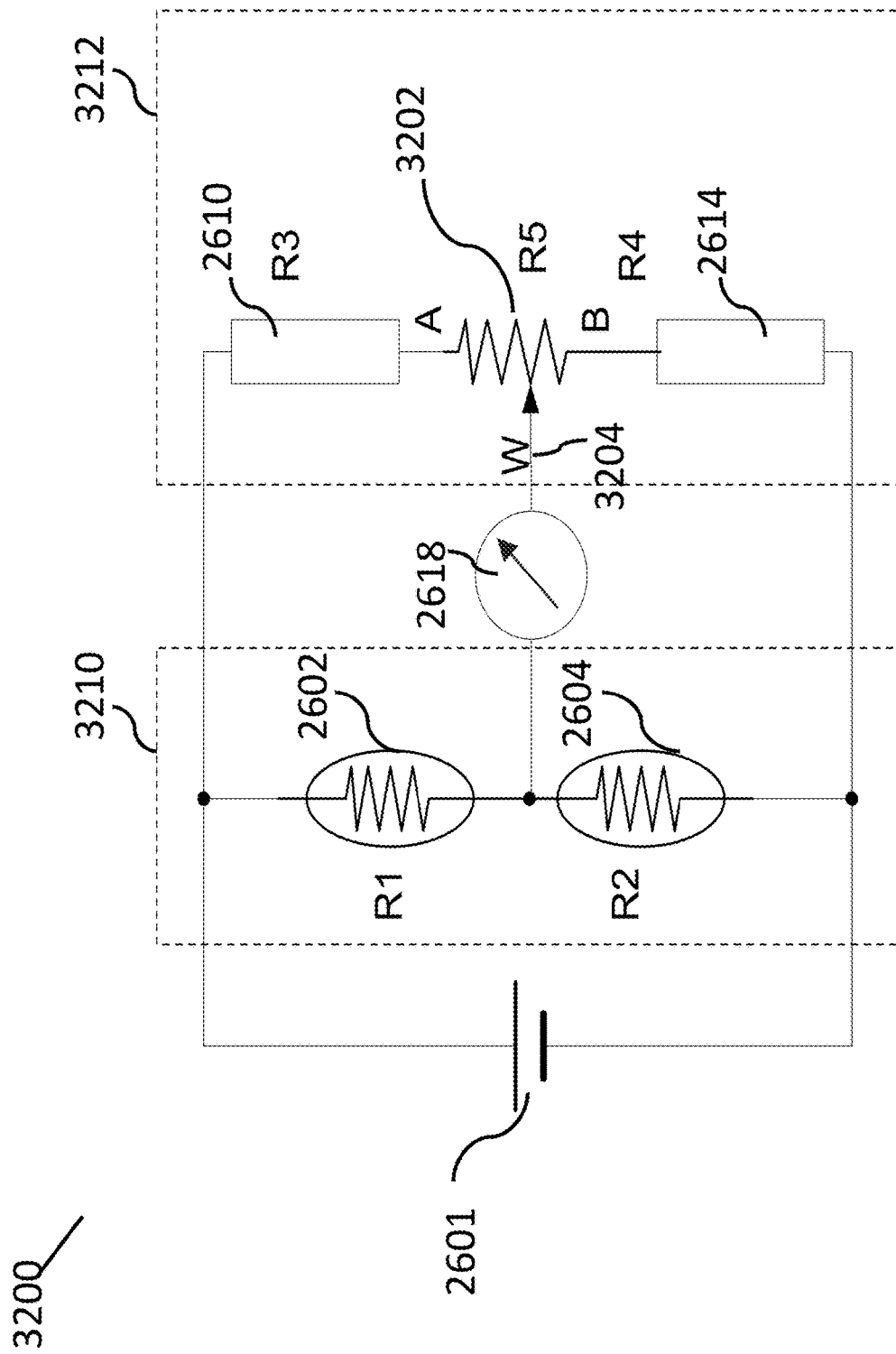
FIG. 32A depicts a balanced bridge circuit.
Figure 32B:
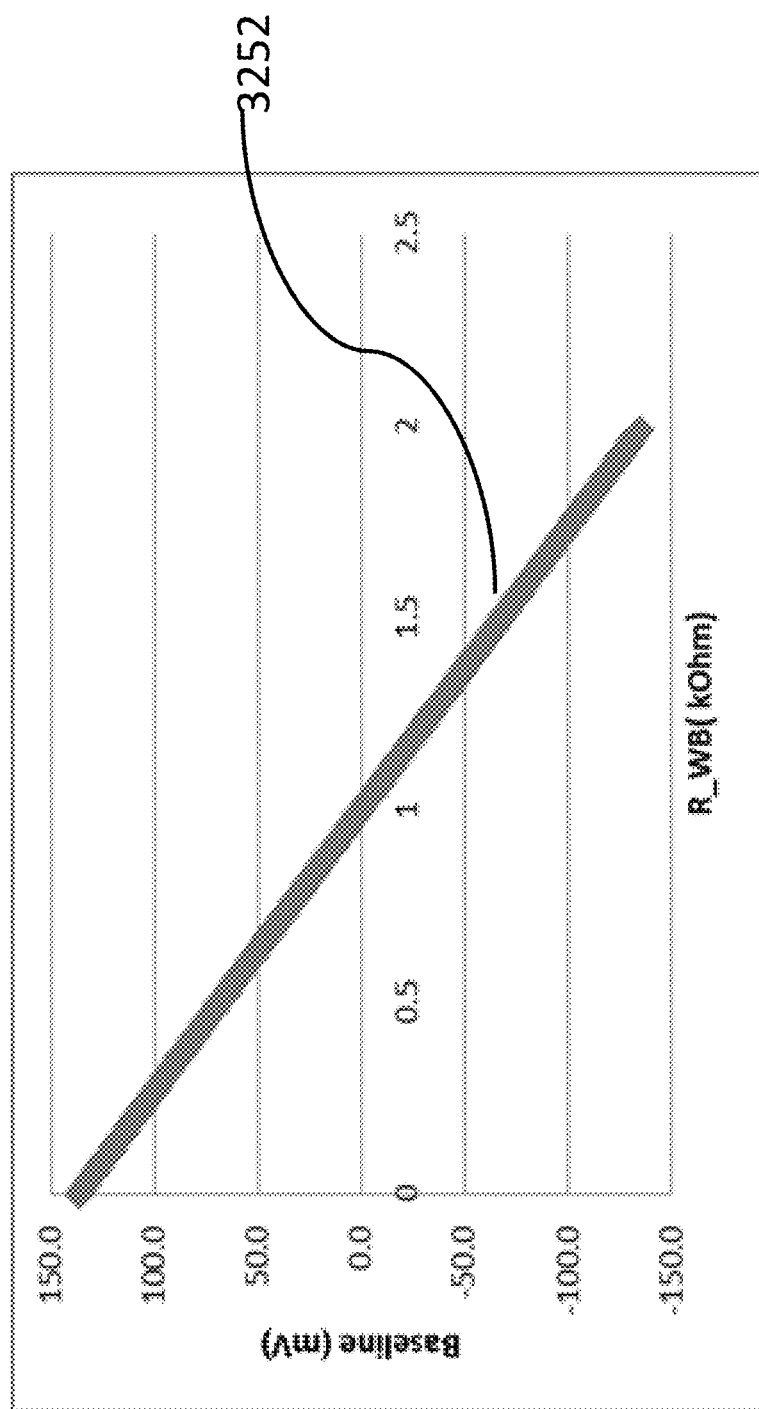
FIG. 32B depicts the relationship between component value and baseline.

FIG. 32A depicts another embodiment of a balanced bridge circuit 3200 which is a variant of the embodiment of FIG. 30A. There are two branches connected in parallel with each other and a power source 2601. The first branch 3210 has a sensor bead 2602 and a compensating bead 2604 connected in series. The second branch 3212 has a three-terminal variable resistor 3202, which may be a digital potentiometer, connected in series between standard resistors R3 2610 and R4 2614, while the wiper 3204 terminal is connected to one side of a differential output meter 2618. The other end of the differential output meter 2618 is connected to the first branch 3210 between the sensor bead 2602 and the compensating bead 2604. In this way, by moving the wiper 3204 up and down, the bridge may be adjusted to match the changes of beads R1 2602 and R2 2604. Considering the typical baseline drift of a catalytic sensor may be small, this circuit may enable accurate and linear tuning. FIG. 32B depicts a simulation of the resulting change in baseline differential output 3252 as the wiper 3204 is adjusted. As depicted, the tuning steps are fine and linear over most of the range of tuning. For example, assuming R3 2610 and R4 2614 are 10K ohms, R5 3202 is 2K ohms with 256 steps, and the power supply 2601 is 3V, the adjustable baseline 3252 may be as small as 1.1 mV.

Figure 33:
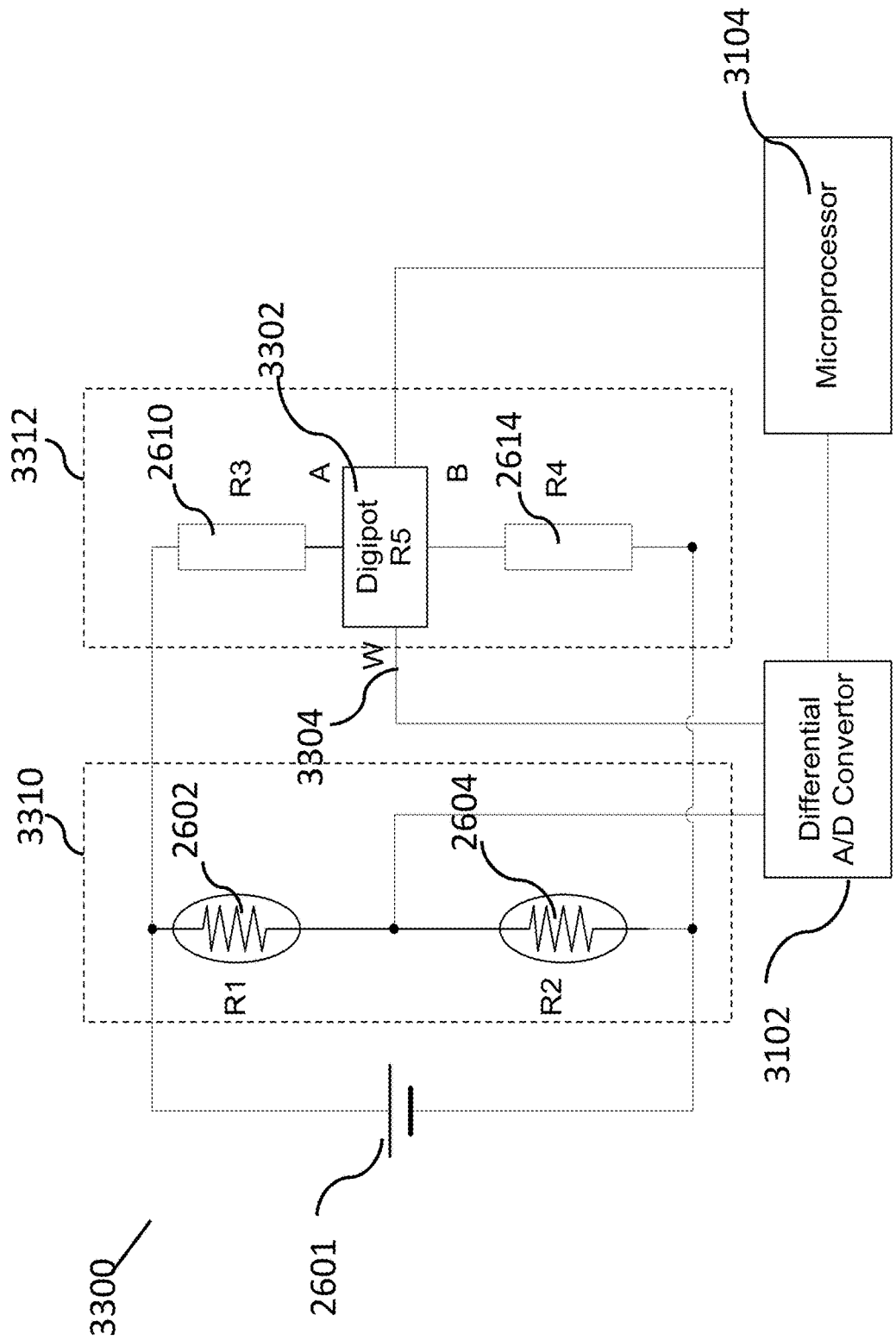
FIG. 33 depicts a balanced bridge circuit.

FIG. 33 depicts an embodiment of a balanced bridge circuit 3300 balanced through a digital potentiometer and microprocessor in a gas detector. There are two branches connected in parallel with each other and a power source 2601. The first branch 3310 has a sensor bead 2602 and a compensating bead 2604 connected in series. The second branch 3312 has a three-terminal digital potentiometer 3302, connected between two standard resistors R3 2610 and R4 2614. A differential A/D convertor is disposed between the two branches with the connection to the first branch 3310 located between the sensor bead 2602 and the compensating bead 2604. The connection to the second branch 3312 is connected to the wiper 3304 of the digital potentiometer 3302. When the bridge circuit is balanced, the differential output voltage detected by microprocessor 3104 through A/D convertor 3102 stays close to zero if there is no combustible gas present. When a significant baseline drift happens, the differential output will become non-zero (above the tolerance range i.e. 10 mV) even if there is no combustible gas present. At this time, the microprocessor 3104 may calculate how much tuning resistance may be needed to reduce the differential output and send a command to digital potentiometer R5 3302 to change its position of wiper 3304 to match the new R1 2602/R2 2604 values. This tuning may be done in one step and bring down the baseline close to zero.

Continuing with describing particular improvements to environmental sensing devices 108, 110, such as gas monitors, that may be used in the worker safety system, one such improvement relates to lead-free filters for catalytic bead sensors. Catalytic bead sensors used to detect combustible gases may exhibit reduced sensitivity to certain combustible gases such as methane, in the presence of catalyst poisons, such as hydrogen sulfide. The effect of hydrogen sulfide on the catalytic bead sensor may be ameliorated by the use of filters to remove the hydrogen sulfide from the gas passing over the sensor.

There remains an ongoing need for methods for the manufacture of highly efficient filters that do not contain lead.

The methods described herein produce metallic copper filters, wherein some embodiments of the methods disclosed herein produce nanometer-scale metallic copper particles. These may be in the range of 1-100 nanometers. Particles on the nanometer scale may be highly reactive with hydrogen sulfide and may have a high surface area for reacting with hydrogen sulfide. Filters prepared using the methods described herein have a high capacity preventing the transmission of hydrogen sulfide through the filter. While porous glass fiber filters will be used throughout this specification as an exemplary substrate in the embodiments, it should be understood that other substrates may also be useful in the embodiments of the disclosure, such as alumina, silica, zirconia, and titanium substrates. Indeed, in some embodiments, the metallic copper particles may themselves be used as the filter without any need for a supporting substrate.

Figure 34:
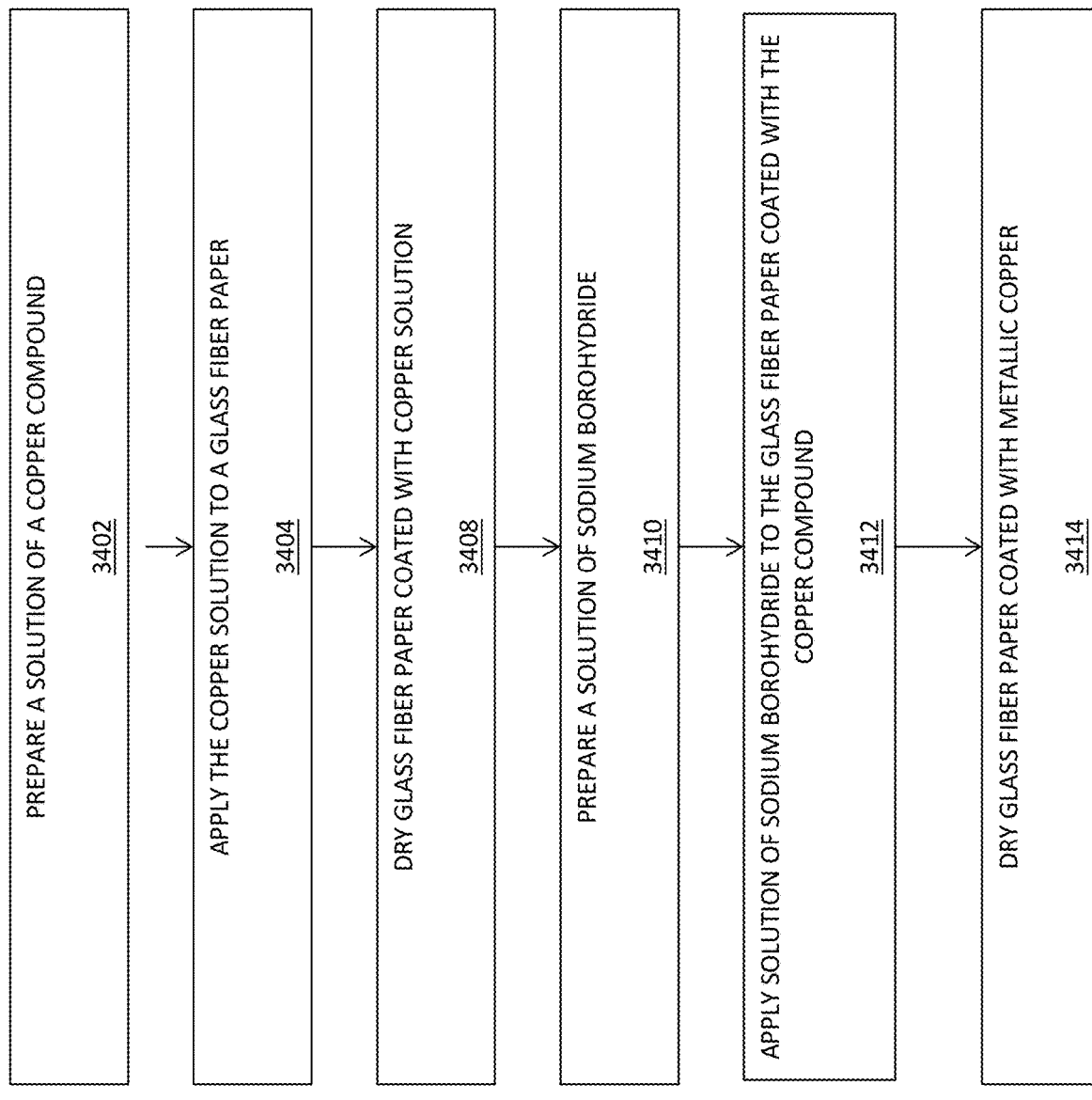
FIG. 34 depicts a method for the production of a metallic copper filter for hydrogen sulfide.

In one embodiment, referring to FIG. 34, a metallic copper particle filter may be made by preparing a solution of a copper compound (step 3402), such as copper sulfate, copper chloride and the like and applying the copper solution to a glass fiber paper (step 3404). The glass fiber paper coated with the copper compound may then be dried (step 3408) at room temperature or at an elevated temperature. A second solution of sodium borohydride may be prepared (step 3410) and applied to the glass fiber paper coated with the copper compound (step 3412) resulting in the copper compound being reduced to metallic copper. The glass fiber paper coated with the metallic copper is then dried (step 3414) at room temperature or at an elevated temperature for use in the sensor.

Figure 35:
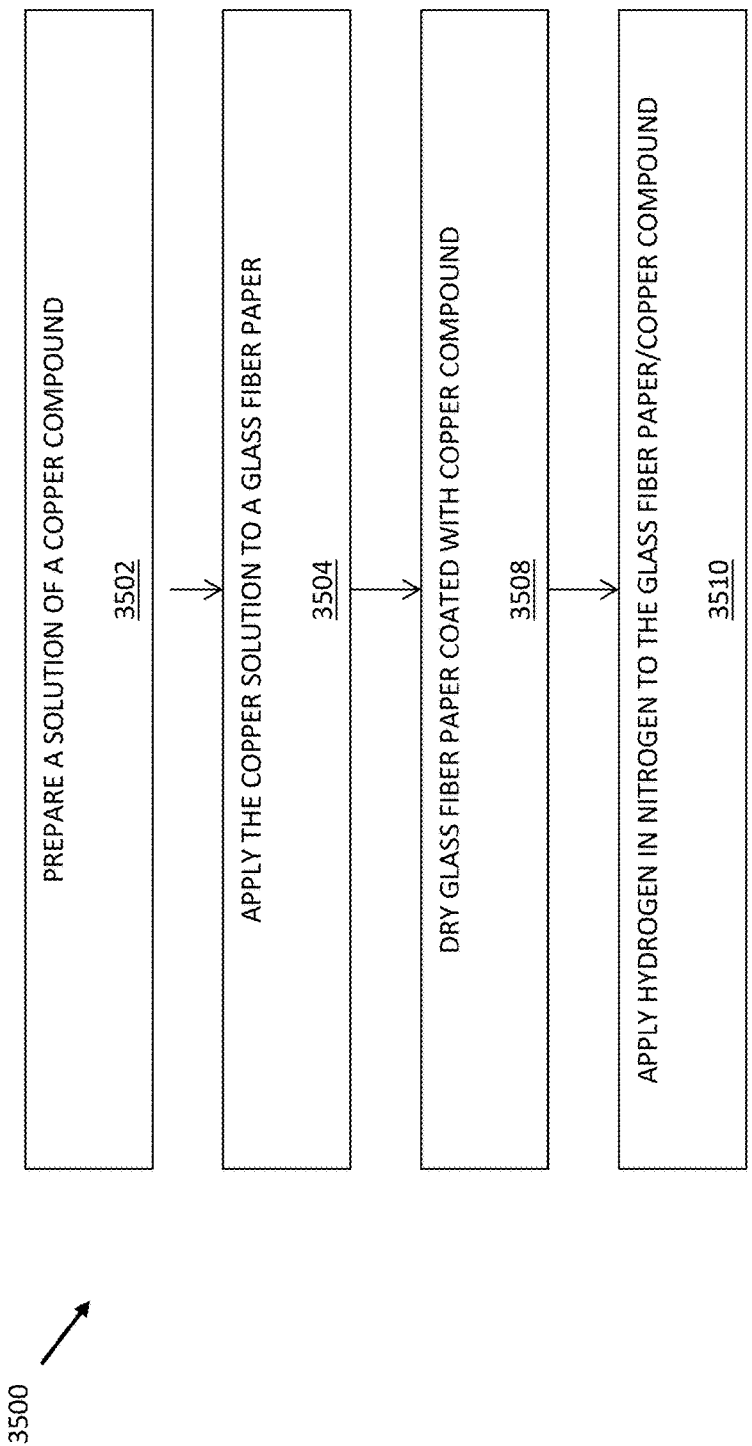
FIG. 35 depicts a method for the production of a metallic copper filter for hydrogen sulfide.

In another embodiment, and referring now to FIG. 35, a metallic copper particle filter may be made by preparing a solution of copper compound (step 3502) and applying the copper solution to a glass fiber paper (step 3504). The glass fiber paper coated with the copper solution may then be dried (step 3508) at room temperature or at an elevated temperature. Hydrogen in nitrogen may then be applied to the glass fiber paper coated with the copper compound (step 3510) resulting in the copper compound being reduced to metallic copper particles.

Figure 36:
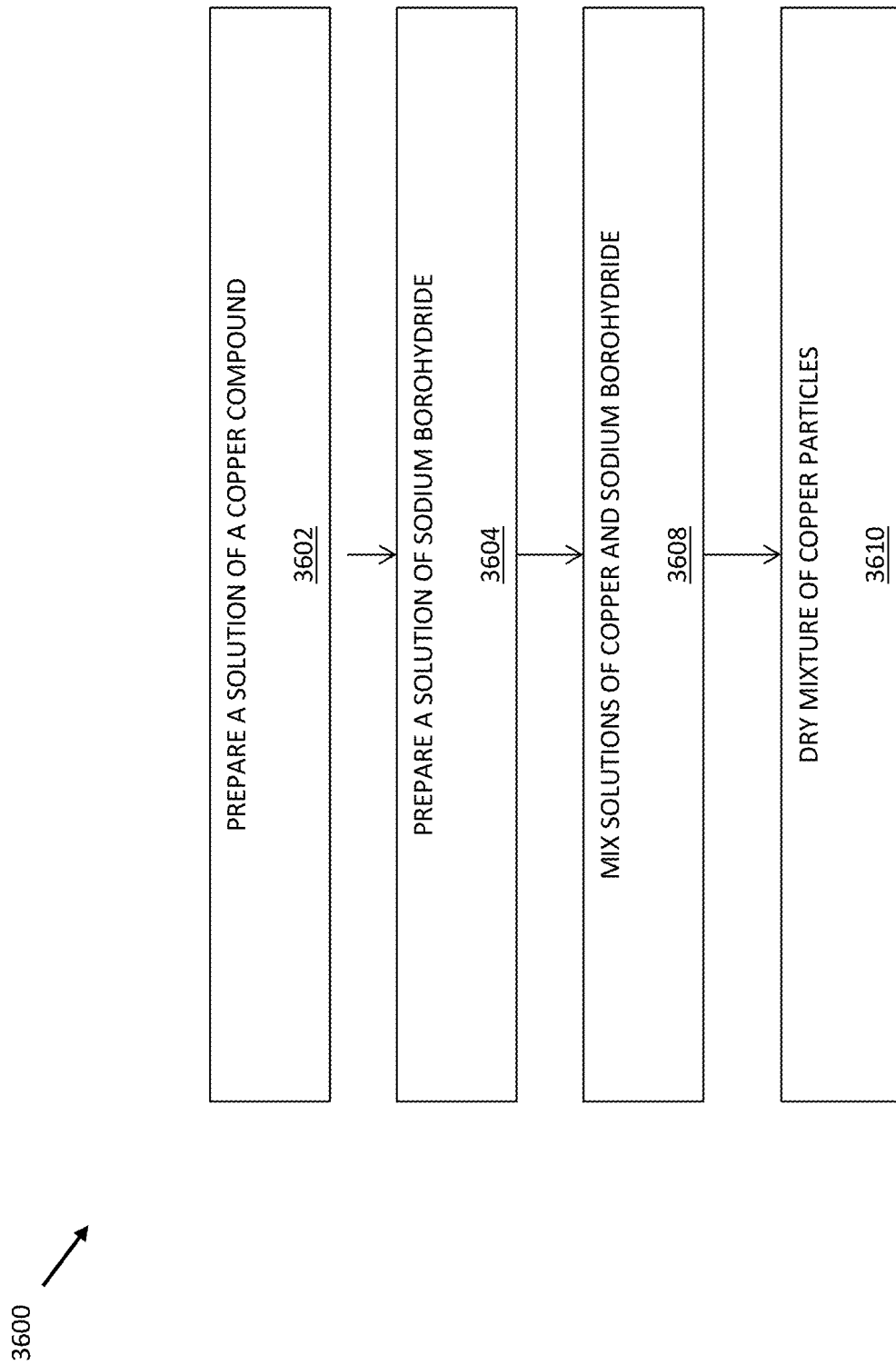
FIG. 36 depicts a method for the production of a metallic copper filter for hydrogen sulfide.

In another embodiment, and referring to FIG. 36, a metallic copper particle filter may be made by preparing a solution of a copper compound (step 3602), preparing a solution of sodium borohydride (step 3604), and mixing the two solutions (step 3608) resulting in the copper compound being reduced to metallic copper particles. The metallic copper particles may then be dried (step 3610) at room temperature or at an elevated temperature.

Since the copper particles are small in size, the filter color may be black instead of bronze (color of copper large particles or pieces). The copper particles may form a porous material to effectively block hydrogen sulfide.

Figure 37:
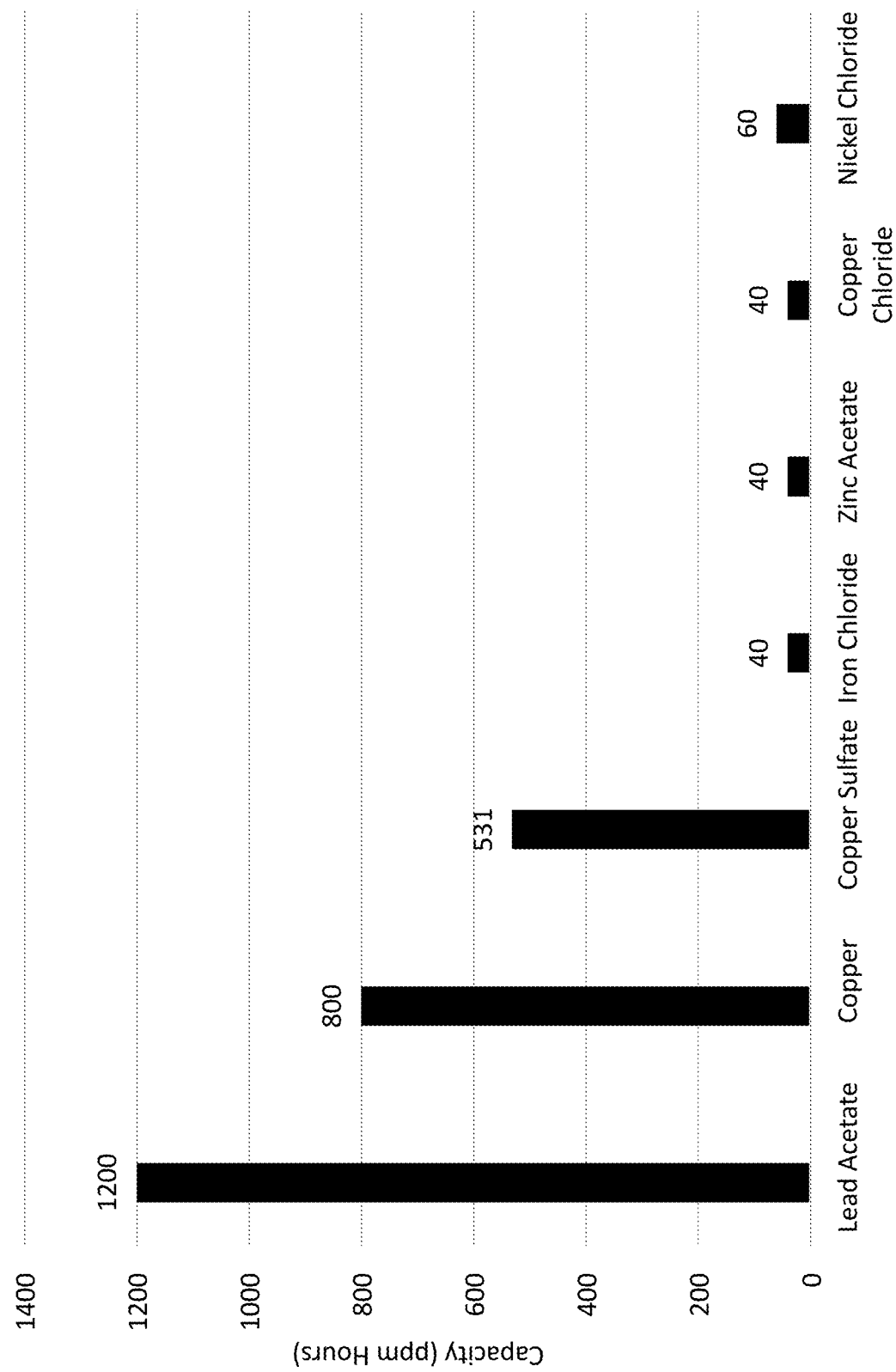
FIG. 37 shows a graph of the relative capacity of different filters.

As shown in FIG. 37, a graph comparing the capacity of different hydrogen sulfide filters, in parts per million (ppm) Hours (hrs), is shown. The graph charts the capacity of a disclosed metallic copper filter created using the method of FIG. 34 (800 ppm hrs) as well as a lead acetate filter (1200 ppm hrs), a copper sulfate filter (531 ppm hrs), an iron chloride filter (40 ppm hrs), a zinc acetate filter (40 ppm hrs), a copper chloride filter (40 ppm hrs), and a nickel chloride filter (60 ppm hrs). The data in this graph can be interpreted as demonstrating that the metallic copper particle filter and the copper sulfate filter, approach the capacity of the conventional lead acetate filter.

Figure 38:
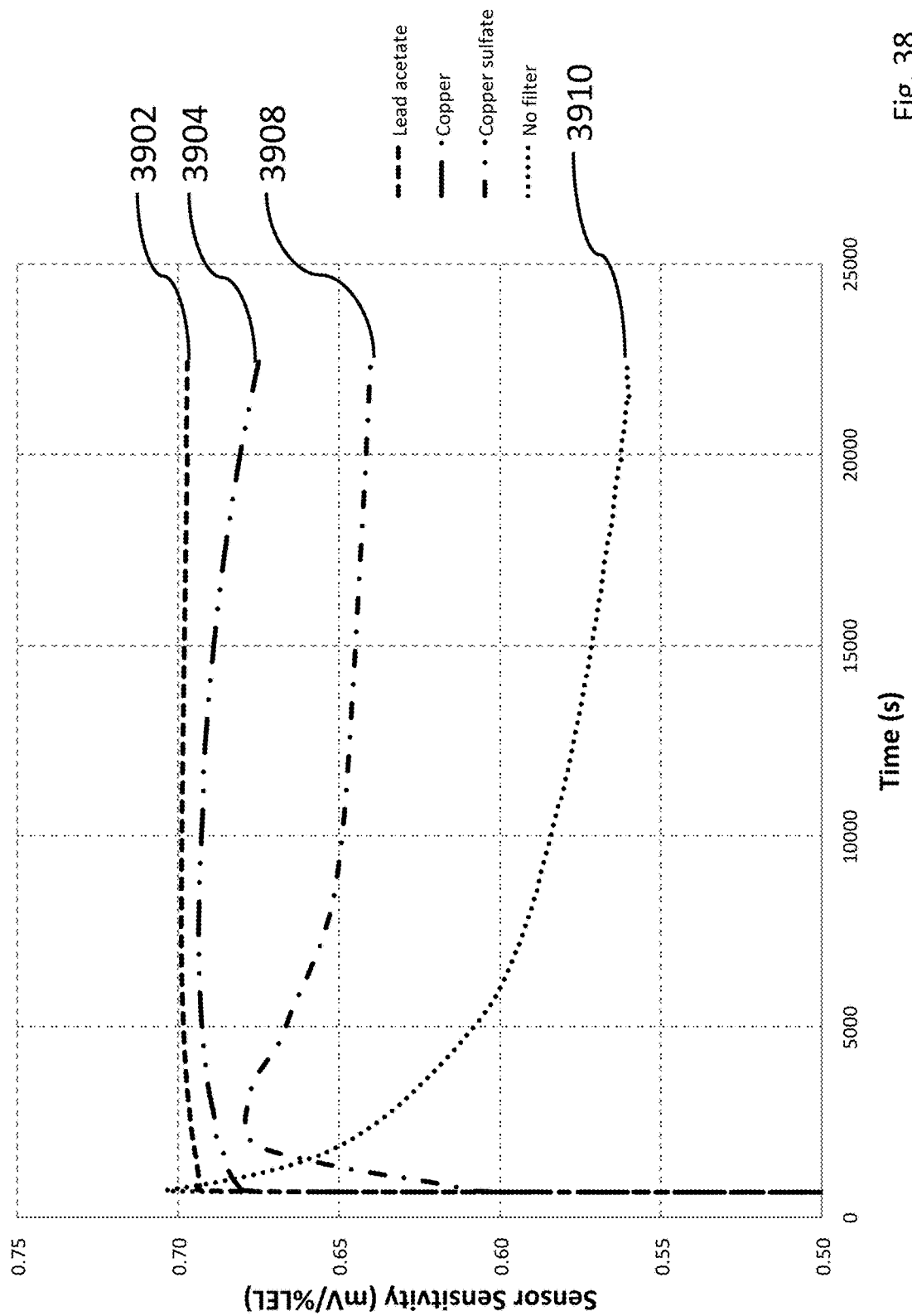
FIG. 38 shows a graph of sensor sensitivity over time in a hydrogen sulfide environment.

The effectiveness of filters made using the methods described herein may be seen in FIG. 38, a graph depicting the change in methane sensitivity (in mV/% LEL) of a sensor over time in an atmosphere having 25 parts per million (ppm) of hydrogen sulfide. In the absence of a filter 3910, the sensitivity falls off quickly. However, the presence of a filter of lead acetate 3902 or metallic copper 3904 show very little fall off in sensitivity over time spent in the presence of hydrogen sulfide. A filter of copper sulfate 3908 provides some protection but there is a noticeable decrease in sensitivity relative to the metallic copper filter 3904 and always remains below that of metallic copper.

Continuing with describing particular improvements to environmental sensing devices 108, 110, such as gas monitors, that may be used in the worker safety system, one such improvement relates to mechanical stability. Catalytic bead combustible gas sensors have been widely used in industry to detect the presence of combustible gases and vapors for safety purposes and to provide a warning of potentially hazardous conditions before these gases and vapors reach explosive levels. Commercial catalytic bead sensors detect gases through the use of electrically heated helical filaments typically embedded within a catalytic material. The mechanical stability of this assembly is compromised by the weight of the catalytic material itself. Thus, there remains a need for combustible gas sensors with improved mechanical stability.

Figure 39A:
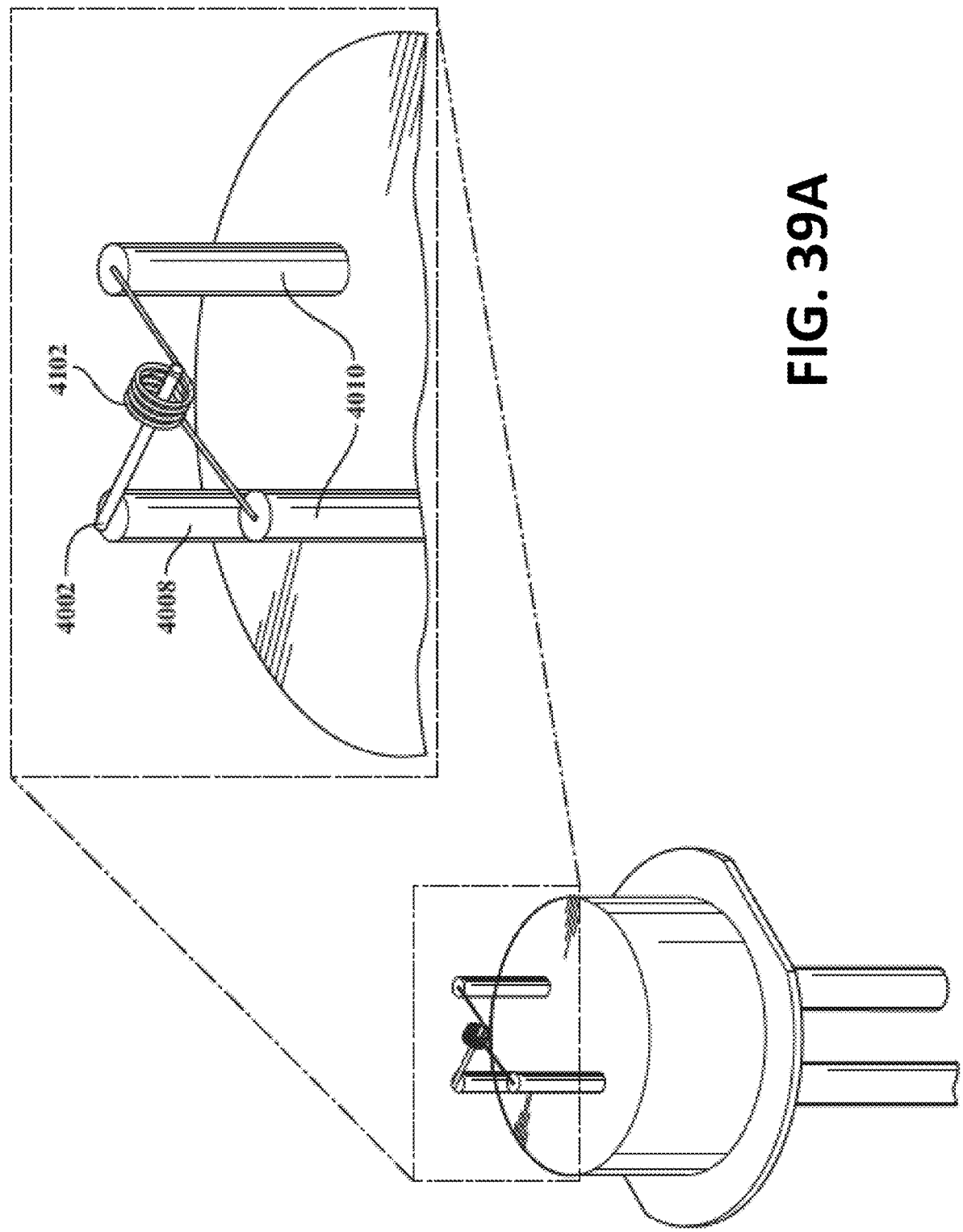
FIG. 39A depicts a three support post design of a gas sensing or compensating element of a gas sensor, before bead fabrication, with a cantilever placed through the center of a coated coil, and attached to the third support post.

Referring to FIGS. 39A & 39B, a gas sensing or compensating element of a combustible gas sensor is shown. A cantilever support 4002 is connected to a coated coil 4004 and attached to a third support post 4008. The coated coil 4004 is attached to two support posts 4010. The coated coils is coated via chemical vapor deposition (CVD) with an insulating material that keeps the winds of the coil from touching and creating hot spots and prevents the cantilever support 4002 from shorting the coil turns electronically. In embodiments, the cantilever support 4002 supports the wire that the coil 4004 is a part of, and may be connected to the coil by soldering, but it is understood that other attachment methods are contemplated as well. In some embodiments, the cantilever 4002 is disposed or threaded entirely through the coil 4004 and emerges on the other side of the coil, such as shown in FIG. 39A, while in other embodiments, the cantilever 4002 is only partially disposed or threaded through the coil. In some embodiments, the cantilever 4002 supports the coil 4004 from beneath, such as in FIG. 39B, or from above the coil. The coated coil 4004 is part of a resistance wire whose ends are attached to the support posts 4010. While in some embodiments, the cantilever does not touch the coil, it is possible for the cantilever to touch the coil since the coil is coated with an insulating material, such as in FIG. 39C.

Figure 40:
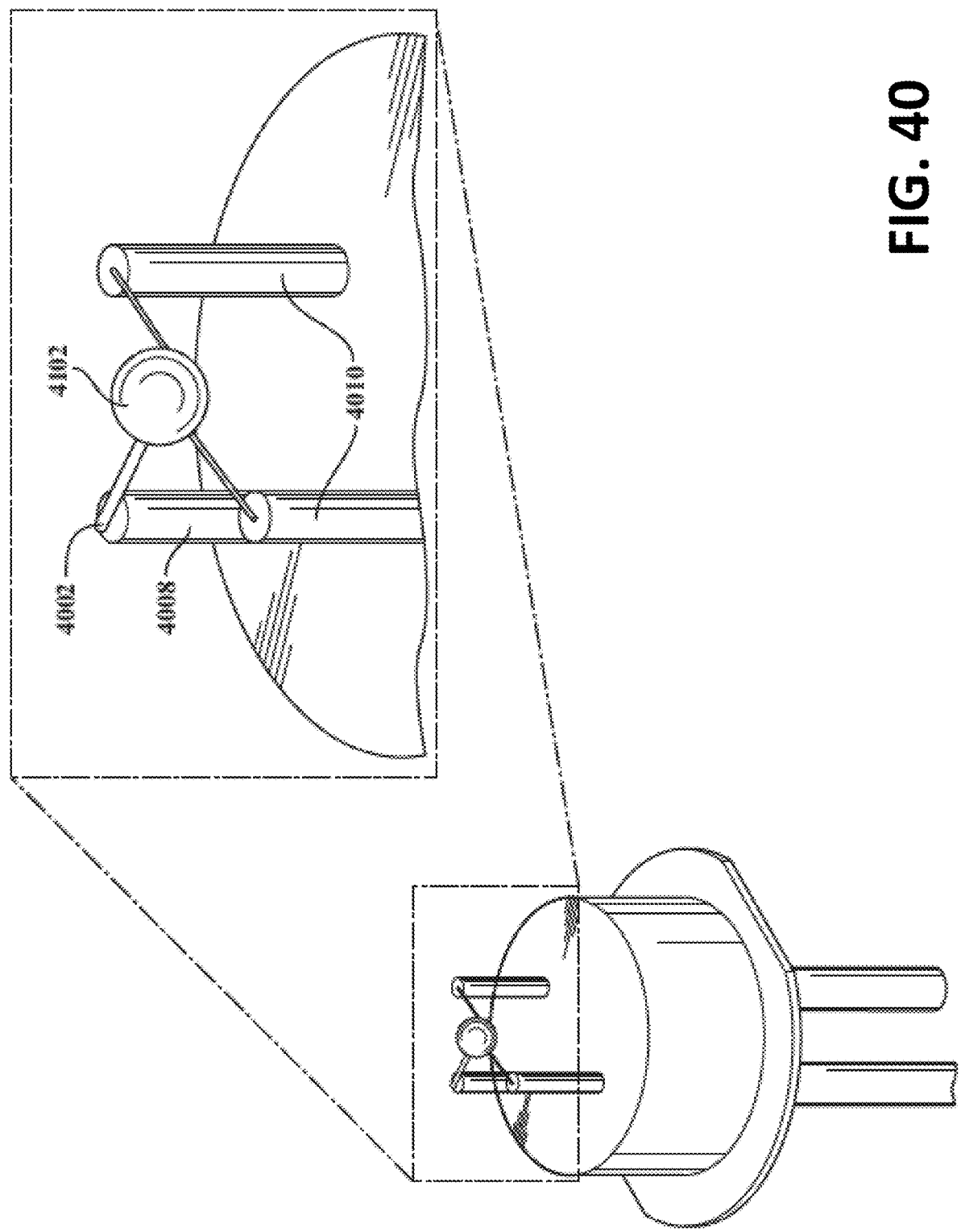
FIG. 40 depicts a three support post design of a gas sensing or compensating element of a gas sensor, after bead fabrication, the bead fabricated to coat both the cantilever support and the coil.

Referring to FIG. 40, a bead 4102 is fabricated to coat both the cantilever support 4002 and the coil 4004. The bead 4102 may be of a catalytic material or may be another material, such as ceramic, coated with or mixed with a catalytic material, such as platinum or palladium. In an embodiment, the bead 4102 may include an inner layer of a porous oxide-supported precious metal catalyst that catalyzes the combustion reaction, and an outer layer of a porous oxide-supported catalytic material that effectively traps catalyst poisons. Formation of the bead 4102 (either a sensing bead or a compensating bead) may occur by various processes, such as those described in U.S. Pat. No. 7,007,542, which is incorporated by reference herein.

In operation, electrical currents are passed through the coil 4004 causing it to become heated. Combustible gases that come in contact with the catalytic material of the bead 4102 coating the coil 4004 may combust at a lower than normal ignition temperature, causing further heating of the coil 4004 and a change in its electrical resistance which is detected by sensor-associated electronics.

Adding a third support post 4008 to the gas sensing element enables use of the cantilever 4002 to mechanically support the excess weight of the catalytic bead 4102 and also allow for a reduced coil wire size to reduce the power necessary to run the system. The cantilever 4002 may be threaded through the center of the coil 4004 and is subsequently coated together with the coil 4004 within the bead 4102 during bead fabrication, thus ensuring that the cantilever 4002 and the coil 4004 are mechanically joined for more stable support.

By using only three support posts, fabricating the bead 4102 is more convenient with access to the entire open side (opposite the cantilever 4002) of the coil 4004. Further, less power loss is observed when only requiring one additional support as less additional operational power is required to overcome associated heat loss with three supports over designs that incorporate more than three supports. Mechanical stability of the assembly is greatly improved with the cantilever 4002 as exhibited by the results of durability testing, which may involve dropping an instrument containing the gas sensing element from one meter onto concrete. Without the cantilever 4002, the sensor withstands fewer drops (e.g. eight) before malfunction or breakage, but with the cantilever 4002, the sensor can withstand numerous drops (e.g. greater than fifty-two). The cantilever 4002 also enables the use of very thin coil wire, such as 0.5 mil, to reduce the power necessary to run the system. Decreased wire diameter may result in higher resistance, and concomitantly, a reduction in the sensor's overall electrical requirements (power and current) in achieving a particular operating temperature. Such a reduction in power requirement may result in extending the life of the power supply or in enabling the further reduction of the size of the power supply.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable transitory and/or non-transitory media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A catalytically activated combustible gas sensing element, comprising:
    a filament of resistance wire forming a coil, wherein a first end of the resistance wire is attached to a first support post and a second end of the resistance wire is attached to a second support post;
    a cantilever support supporting the coil, wherein the cantilever support is attached to a third support post, and wherein the cantilever support is disposed either above the resistance wire or below the resistance wire; and
    a catalytic bead substantially surrounding the coil and cantilever.

2. The gas sensing element of claim 1, wherein the filament of resistance wire is coated via chemical vapor deposition with an insulating material preventing winds of the coil from electrically conducting through an exterior surface of the filament of resistance wire.

3. The gas sensing element of claim 1, wherein the cantilever support is attached to the filament of resistance wire.

4. The gas sensing element of claim 3, wherein the cantilever support is attached to the filament of resistance wire by soldering.

5. The gas sensing element of claim 3, wherein the cantilever support is attached to a single coil of the filament of resistance wire.

6. The gas sensing element of claim 3, wherein the cantilever support is attached to more than one, but not all coils of the filament of resistance wire.

7. The gas sensing element of claim 3, wherein the cantilever support is attached to all coils of the filament of resistance wire.

8. A catalytically activated combustible gas sensing element, comprising:
    a filament of resistance wire forming a coil, wherein a first end of the filament of resistance wire is attached to a first support post and a second end of the filament of resistance wire is attached to a second support post; and
    a cantilever support supporting the coil, wherein the cantilever support is attached to a third support post, wherein the cantilever support is disposed within a catalytic bead, but does not contact the filament of resistance wire, the catalytic bead substantially surrounding the coil.

9. The gas sensing element of claim 8, wherein the catalytic bead comprises one or both of platinum or palladium.

10. The gas sensing element of claim 1, wherein the catalytic bead comprises a catalytic material.

11. The gas sensing element of claim 10, wherein the catalytic material comprises one or both of platinum or palladium.

12. The gas sensing element of claim 1, wherein the catalytic bead comprises a ceramic material.

13. The gas sensing element of claim 1, wherein the catalytic bead comprises an inner layer of a porous oxide-supported precious metal catalyst and an outer layer of a porous oxide-supported catalytic material.

14. A catalytically activated combustible gas sensing element comprising:
    a filament of resistance wire forming a coil, wherein the resistance wire is of a diameter equal to or less than 0.5 millimeters, wherein a first end of the resistance wire is attached to a first support post and a second end of the resistance wire is attached to a second support post; and
    a cantilever support adapted to support the coil, wherein the cantilever support is attached to a third support post, and wherein the cantilever support is disposed either above the resistance wire or below the resistance wire;
    wherein the resistance wire can withstand more than eight drops of one meter onto concrete without breakage.

15. The gas sensing element of claim 14, wherein the cantilever support is attached to the resistance wire.

16. The gas sensing element of claim 15, wherein the cantilever support is attached to a single coil of the resistance wire.

17. The gas sensing element of claim 15, wherein the cantilever support is attached to more than one, but not all coils of the resistance wire.

18. The gas sensing element of claim 15, wherein the cantilever support is attached to all coils of the resistance wire.

19. A catalytically activated combustible gas sensing element comprising:

- a filament of resistance wire forming a coil, wherein the resistance wire is of a diameter equal to or less than 0.5 millimeters, wherein a first end of the resistance wire is attached to a first support post and a second end of the resistance wire is attached to a second support post; and
- a cantilever support adapted to support the coil, wherein the cantilever support is attached to a third support post, wherein the cantilever support is disposed within a catalytic bead, but does not contact the filament of resistance wire, and wherein the resistance wire can withstand more than eight drops of one meter onto concrete without breakage.

20. The gas sensing element of claim 19, enveloping the cantilever support and the resistance wire wherein the catalytic bead comprises one or both of platinum or palladium.

21. The gas sensing element of claim 14, further comprising a catalytic bead enveloping the filament of resistance wire, wherein the catalytic bead comprises a catalytic material.

22. The gas sensing element of claim 21, wherein the catalytic material comprises one or both of platinum or palladium.

23. The gas sensing element of claim 20, wherein the catalytic bead comprises a ceramic material.

24. The gas sensing element of claim 20, wherein the catalytic bead comprises an inner layer of a porous oxide-supported precious metal catalyst and an outer layer of a porous oxide-supported catalytic material.

25. The gas sensing element of claim 8, wherein the catalytic bead comprises a ceramic material.

26. The gas sensing element of claim 8, wherein the catalytic bead comprises an inner layer of a porous oxide-supported precious metal catalyst and an outer layer of a porous oxide-supported catalytic material.

27. The gas sensing element of claim 19, wherein the catalytic bead comprises a ceramic material.

28. The gas sensing element of claim 19, wherein the catalytic bead comprises an inner layer of a porous oxide-supported precious metal catalyst and an outer layer of a porous oxide-supported catalytic material.

\* \* \* \* \*

UNITED STATES PATENT AND TRADEMARK OFFICE
CERTIFICATE OF CORRECTION

PATENT NO. : 10,533,965 B2  
APPLICATION NO. : 15/665034  
DATED : January 14, 2020  
INVENTOR(S) : Chuan-Bao Wang et al.

Page 1 of 2

It is certified that error appears in the above-identified patent and that said Letters Patent is hereby corrected as shown below:

On the Title Page

On the Page 3, in Column 1, under "Other Publications", Line 5, delete "MUL Tigas" and insert -- Multigas --, therefor.

On the Page 3, in Column 2, under "Other Publications", Line 6, delete "Pricipal" and insert -- Principal --, therefor.

On the Page 3, in Column 2, under "Other Publications", Line 15, delete "Intrinisically" and insert -- Intrinsically --, therefor.

In the Drawings

On Sheet 11 of 49, in Figure 10, Line 8, delete "sync()," and insert -- sync() --, therefor.

On Sheet 13 of 49, in Figure 12, reference numeral 1214, Line 6, delete "etc.," and insert -- etc. --, therefor.

On Sheet 13 of 49, in Figure 12, reference numeral 1214, Line 7, delete "etc.," and insert -- etc. --, therefor.

On Sheet 13 of 49, in Figure 12, reference numeral 1220, Line 5, delete "etc.," and insert -- etc. --, therefor.

On Sheet 14 of 49, in Figure 13, Line 3, delete "etc.)" and insert -- etc. --, therefor.

In the Specification

In Column 3, Line 43, delete "A" and insert -- a --, therefor.

Signed and Sealed this  
Nineteenth Day of May, 2020

Andrei Iancu  
*Director of the United States Patent and Trademark Office*

CERTIFICATE OF CORRECTION (continued)
U.S. Pat. No. 10,533,965 B2

In Column 17, Lines 21-22, delete "environmental." and insert -- environmental attribute. --, therefor.

In Column 22, Line 58, delete "mV/% LEL" and insert -- mV/%LEL --, therefor.

In Column 25, Line 20, after "baseline" insert -- . --.

In Column 29, Line 32, after "destination" insert -- . --.

In Column 39, Line 14, after "boPeep( )" insert -- ; --.

In Column 48, Line 41, delete "and or" and insert -- and/or --, therefor.

In Column 52, Line 20, after "nodes" insert -- . --.

In Column 56, Line 48, below "condition." insert -- Table 2 depicts how various physiological markers are associated with particular root causes or symptoms. --.

In Column 59, Line 9, after "like" insert -- . --.

In Column 65, Line 25, delete "my" and insert -- may --, therefor.

In Column 76, Line 25, delete "mV/% LEL)" and insert -- mV/%LEL) --, therefor.

In the Claims

In Column 83, Lines 23-24, in Claim 20, after "claim 19," delete "enveloping the cantilever support and the resistance wire".